US010703823B2

(12) United States Patent
Spiegel et al.

(10) Patent No.: US 10,703,823 B2
(45) Date of Patent: *Jul. 7, 2020

(54) CHIMERIC SMALL MOLECULES FOR THE RECRUITMENT OF ANTIBODIES TO CANCER CELLS

(71) Applicant: YALE UNIVERSITY, New Haven, CT (US)

(72) Inventors: David Spiegel, New Haven, CT (US); Ryan Murelli, Belleville, NJ (US); Andrew Zhang, Waltham, MA (US)

(73) Assignee: YALE UNIVERSITY, New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/045,855

(22) Filed: Jul. 26, 2018

(65) Prior Publication Data

US 2019/0127487 A1 May 2, 2019

Related U.S. Application Data

(60) Continuation of application No. 15/083,025, filed on Mar. 28, 2016, now Pat. No. 10,066,026, which is a continuation of application No. 14/480,204, filed on Sep. 8, 2014, now Pat. No. 9,296,708, which is a division of application No. 13/173,480, filed on Jun. 30, 2011, now Pat. No. 8,852,630, which is a continuation-in-part of application No. 12/991,926, filed as application No. PCT/US2009/002957 on May 13, 2009, now Pat. No. 8,859,509.

(60) Provisional application No. 61/127,539, filed on May 13, 2008, provisional application No. 61/360,732, filed on Jul. 1, 2010.

(51) Int. Cl.
| | |
|---|---|
| *C07K 16/44* | (2006.01) |
| *C07K 16/30* | (2006.01) |
| *A61K 9/00* | (2006.01) |
| *A61K 47/68* | (2017.01) |
| *A61K 45/06* | (2006.01) |
| *A61K 31/4192* | (2006.01) |
| *A61K 47/54* | (2017.01) |
| *C07D 249/04* | (2006.01) |
| *A61K 47/64* | (2017.01) |
| *A61K 47/55* | (2017.01) |

(52) U.S. Cl.
CPC ............ *C07K 16/44* (2013.01); *A61K 9/0019* (2013.01); *A61K 31/4192* (2013.01); *A61K 45/06* (2013.01); *A61K 47/54* (2017.08); *A61K 47/549* (2017.08); *A61K 47/55* (2017.08); *A61K 47/646* (2017.08); *A61K 47/68* (2017.08); *A61K 47/6803* (2017.08); *A61K 47/6869* (2017.08); *A61K 47/6873* (2017.08); *A61K 47/6891* (2017.08); *C07D 249/04* (2013.01); *C07K 16/3069* (2013.01); *C07K 2317/31* (2013.01)

(58) Field of Classification Search
CPC C07K 16/3069; C07K 16/44; C07K 2317/31; C07D 249/04; A61K 31/4192; A61K 45/06; A61K 9/0019; A61K 47/6869; A61K 47/68; A61K 47/646; A61K 47/6873; A61K 47/6803; A61K 47/54; A61K 47/549

USPC ........... 514/54, 93, 19.3; 536/17.9; 548/255; 530/389.1; 424/450

See application file for complete search history.

(56) References Cited

U.S. PATENT DOCUMENTS

| | | | |
|---|---|---|---|
| 4,522,811 A | 6/1985 | Eppstein et al. | |
| 6,780,884 B2 | 8/2004 | Zisapel et al. | |
| 8,852,630 B2 * | 10/2014 | Spiegel ............... | C07K 16/3069 424/450 |
| 8,859,509 B2 * | 10/2014 | Spiegel .................. | C07K 16/44 514/114 |
| 9,296,708 B2 * | 3/2016 | Spiegel .............. | C07K 16/3069 |
| 10,066,026 B2 * | 9/2018 | Spiegel .............. | C07K 16/3069 |
| 2004/0029778 A1 | 2/2004 | Isaacs et al. | |
| 2005/0256030 A1 | 11/2005 | Feng | |
| 2007/0248988 A1 | 10/2007 | Cuervo et al. | |
| 2008/0171040 A1 | 7/2008 | Ebens et al. | |
| 2008/0267865 A1 | 10/2008 | Sandberg et al. | |
| 2010/0324008 A1 | 12/2010 | Low et al. | |

FOREIGN PATENT DOCUMENTS

| | | | | |
|---|---|---|---|---|
| WO | 0174382 | A1 | 10/2001 | |
| WO | 0306523 | A1 | 7/2003 | |
| WO | 03064606 | A2 | 8/2003 | |
| WO | 2007002222 | A2 | 1/2007 | |
| WO | 2009026177 | A1 | 2/2009 | |
| WO | WO 2009/026177 | A1 * | 2/2009 | ........... A61K 39/395 |

OTHER PUBLICATIONS

Baird et al, Biochemistry, 2003, 12739-74.*
Zhang et al, J. Am. Chem. Soc., 2010, 132, 12711-716.*

(Continued)

*Primary Examiner* — Ganapathy Krishnan
(74) *Attorney, Agent, or Firm* — Henry D. Coleman; R. Neil Sudol

(57) ABSTRACT

The present invention relates to chimeric chemical compounds which are used to recruit antibodies to cancer cells, in particular, prostate cancer cells or metastasized prostate cancer cells. The compounds according to the present invention comprise an antibody binding terminus (ABT) moiety covalently bonded to a cell binding terminus (CBT) through a linker and optionally, a connector molecule.

26 Claims, 19 Drawing Sheets

(56) References Cited

OTHER PUBLICATIONS

Dubrovska A, et al. A Chemically Induced Vaccine Strategy for Prostate Cancer. ACS Chem Biol, 2011;6:1223-1231.
Xia W, Low PS. Folate-Targeted Therapies for Cancer. J Med Chem, 2010;53:6811-6824.
Shokat KM, Schultz PG. Redirecting the Immune Response: Ligand-Mediated Immunogenicity. J Am Chem Soc, 1991;113:1861-1862.
Hagins DM, et al. A Comparison of the Amino Terminal Acids Sequences of Early and Late Pool of Anti D1 Nitro Phenol and Anti Dinitro Phenol P Amino Benzoyl Glutamate Antibody Light Chains. Immunology, 1978;34:352-362.
Niculescu-Duvaz D, et al. Long functionalized poly(ethylene glycols)s of defined molecular weight: Synthesis and application in solid-phase synthesis of conjugates. Bioconjugate Chemistry, 2008;19:973-981.
Sibrian-Vazquez M, et al. Synthesis and properties of cell-targeted Zn(II)-phthalocyanine-peptide conjugates. Bioconjugate Chemistry, 2007;18"410-420.
Popkov M, et al. Instant Immunity through chemically programmable vaccination and covalent self-assembly. Proc Natl Acad Sci USA, 2009;106:4378-4383.
American Cancer Society, Cancer Facts and Figures 2008. Atlanta: American Cancer Society: 2008.
Ortega E, et al. Natural DNP-Binding Immunoglobulins and Antibody Multispecificity. Mol Immun, 1984;21:883.
Lu, et al. Folate receptor-targeted immunotherapy of cancer: mechanism and therapeutic potential. Adv Drug Deliv Rev, 2004;56:1161.
Lu, et al. Folate-Targeted Dinitrophenyl Hapten Immunotherapy: Effect of Linker Chemistry on Antitumor Activity and Allergic Potential. Mol Pharmaceut, 2007;4:695.
Carlson, et al. Selective Tumor Cell Targeting Using Low-Affinity, Multivalent Interactions. ACS Chem Bio, 2007;2:119.
Popkov M, et al. Instant immunity through chemically programmable vaccination and covalent self-assembly. Proc Nat Acad Sci, 2009;1.
Slusher, et al. Selective inhibition of NAALADase, which converts NAAG to glutamate, reduces ischemic brain injury Nature Medicine, 1999;5:1396.
Kozikowski. Synthesis of Urea-based Inhibitors as Active Site Probes of Glutamate Carboxypeptidase II: Efficacy as Analgesic Agents. J Med Chem, 2004;47:1729.

Link, et al. Presentation and Detection of Azide Functionality in Bacterial Cell Surface Proteins. J Am Chem Soc, 2004;126:10598.
Natarajan, et al. Construction of di-scFv through a trivalent alkyne-azide 1,3-dipolar cycloaddition. J Chem Comm, 2007;7:695.
Bouillon, et al. Microwave Assisted "Click" Chemistry for the Synthesis of Multiple Labeled-Carbohydrate Oligonucleotides on Solid Support. J Org Chem, 2006;71:4700.
Shaprless, Manetsch. In Situ click chemistry: a powerful means for lead discovery. Expert Opinion on Drug Discovery, 2006;1:525:538.
Jackson, et al. Design and Pharmacological Activity of Phosphinic Acid Based NAALADase Inhibitors. J Med Chem, 2001;44:4170-4175.
Liu, Stahl. Two-faced Reactivity of Alkenes. cis—versus trans—Aminopalladation in Aerobic Pd-Catalyzed Intramolecular Aza-Wacker Reactions. J Am Chem Soc, 2007;129:6328-6335.
Luo, et al. Poly(Vinyl alcohol)—graft-poly(ethylene glycol) resins and their use in solid-phase synthesis and supported TEMPO catalysis. Chem Comm, 2007;2136-2138.
Baird, et al. Highly Effective Poly(Ethylene Glycol) Architectures for Specific Inhibition of Immune Receptor Activation. Biochemistry, 2003;42:12739-12748.
Demko, et al. Preparation og 5-Substituted 1H-Tetrazoles from Nitriles in Water. J Org Chem, 2001;66:7945-7950.
Kale, et al. Synthesis of soluble multivalent glycoconjugates that target the Hc region of botulinum neurotoxin A. Bioorg Med Chem Lett, 2007;17:2459-2464.
Shami PJ, et al. Antitumor Activity of JS-K 902-(2,4-Dinitrophenylo) 1-[(4-Ethoxy-carbonyl)piperazine-1-yl] diazenium-1,2-diolate and related O2-Aryl Diazeniumdiolates in vitro and in vivo. Journal of Medicial Chemistry, 2006;49(14):4356-4366.
Baird EJ, et al. Highly Effective Poly(Ethylene Glycol) Architectures for Specific Inhibition of Immune Receptor Activation. Biochemistry, 2003;42:12739-12748.
Gura T. Cancer Models: Systems for Identifying New Drugs Are Often Faulty. Science, 1997;7:278(5340):1041-1042.
Berkow R, et al (editors). The Merch Manual of Diagnosis and Therapy. 1992, pp. 1270-1274 and 1750.
Baird et al, Biotechnology 2003, pp. 12739-12774.
Trisha Gura, Science 1997 Nov., pp. 1041-1042.
The Merck Manual, 1992, pp. 1270-1274 and 1750.
Andrew X. Zhang et al, Journal of the American Chemical Society 2010, vol. 130, pp. 12711-12716.

* cited by examiner

PSMA-binding small molecule

*Scheme 2*

(a) *i.* (Cl$_3$CO)$_2$CO, Et$_3$N, CH$_2$Cl$_2$, -78°C to rt; H-Lys(Cbz)-O*t*-Bu, Et$_3$N, CH$_2$Cl$_2$, rt, (86%); (b) 10% Pd/C, H$_2$ (1 atm), MeOH, rt; (c) TfN$_3$, CuSO$_4$,K$_2$CO$_3$, H$_2$O: MeOH: CH$_2$Cl$_2$, rt, (66% , 2 steps)

(d) 1 chloro 2,4 dinitrobenzene, Et$_3$N, EtOH, reflux (>98%).

*Scheme 3*

(a) Cu(II)SO$_3$, Sodium Ascorbate, *t*-BuOH: H$_2$O (1:1), μwave, 110°C, ;
(b) TFA: CH$_2$Cl$_2$ (2:1), μwave, 60°C (58% yield following HPLC purification).

Exemplary Compounds According to the Invention

Scheme 1a

Scheme 2a

Scheme 3a

Scheme 4a

Scheme 5a

CHIMERIC SMALL MOLECULES FOR THE RECRUITMENT OF ANTIBODIES TO CANCER CELLS

RELATED APPLICATIONS

This application is a continuation application of U.S. patent application Ser. No. 15/083,025 filed on Mar. 28, 2016, which is a continuation application of U.S. patent application Ser. No. 14/480,204 filed on Sep. 8, 2014, which is a division of U.S. patent application Ser. No. 13/173,480 filed Jun. 20, 2011, now U.S. Pat. No. 8,852,630, which is a continuation in part application of U.S. patent application Ser. No. 12/991,926 of identical title, having a 371 filing date of Apr. 12, 2011, which is a United States national phase application of PCT/US2009/002957 (published as WO2009/139863, filed 13 May 2009, now U.S. Pat. No. 8,859,509), which claims priority from U.S. provisional application No. 61/127,539 of identical title filed May 13, 2008. Application Ser. No. 13/173,480 also claims the benefit of priority of U.S. provisional application No. 61/360,732, filed Jul. 1, 2010 of identical title. Each of the foregoing applications in incorporated by reference in its entirety hereof.

GRANT SUPPORT

This invention was supported by a grant from the National Institutes of Health, grant no. 1DP2OD002913-01. Consequently, the government retains certain rights in the invention.

FIELD OF THE INVENTION

The present invention relates to chemical compounds which are used to recruit antibodies to cancer cells, in particular, prostate cancer cells or metastasized prostate cancer cells. The compounds according to the present invention comprise an antibody binding terminus (ABT) moiety covalently bonded to a cell binding terminus (CBT) through a linker and optionally and preferably, a connector molecule. In addition, given that the protein target is found on the neovasculature of most non-prostatic cancer cells, the compounds in the present invention also serves as an antiangiogenic therapy for other cancer types.

BACKGROUND OF THE INVENTION

It has been predicted that one out of every six American men will develop prostate cancer in their lifetime. See, American Cancer Society, *Cancer Facts and FIGS.* 2008. Atlanta: American Cancer Society; 2008. Despite recent advances in both prostate cancer detection and treatment, it remains one of the leading causes of cancer-related death among the American male population.

Anti-DNP antibodies are readily present in high concentrations of the human bloodstream. See Ortega, E.; Kostovetzky, M.; Larralde, C. Mol. Immun. 1984, 21, 883. A number of cancer-related, antibody directing small molecules having been synthesized. See, Lu, et al., *Adv. Drug Deliv. Rev.* 2004, 56, 1161; Lu, et al., *Mol. Pharmaceut.* 2007, 4, 695; Carlson, et al., *ACS Chem. Bio.* 2007, 2, 119; and Popkov, M.; Gonzalez, B.; Sinha, S. C.; Barbas, C. F., III. *Proc. Nat. Acad. Sci.,* 2009, 1.

The present invention is directed to the design and synthesis of a new small-molecule capable of redirecting endogenous anti-dinitrophenyl (DNP) antibodies selectively to prostate cancer cells, and inducing antibody-directed, cell-mediated cytotoxicity.

When prostate cancer is diagnosed prior to metastasis, the patient has a greater then 99% chance of survival. The most successful means for treating prostate cancer at this stage is a radical prostatectomy. Unfortunately, this surgery carries with it the risk of severing nerves and blood vessels associated with sexual organs and the bladder, and can potentially result in impotency or incontinency. Radiation therapy is yet another commonly used procedure that carries the risk of impotency. Half the patients who undergo radiation therapy for prostate cancer become impotent within 2 years of treatment. In addition to the adverse affects associated with these procedures, they are significantly less effective in patients whose cancer has already delocalized or metastasized on diagnosis. In these cases, patients generally undergo even more invasive procedures such as hormonal therapy or chemotherapy. Unfortunately, most patients eventually stop responding to hormonal therapy and the most successful chemotherapeutic, Taxotere, only prolongs the life of advanced prostate cancer patients by 2.5 months on average.

As another alternative therapeutic, monoclonal antibody (mAb)-based immunotherapy has proven clinically beneficial for cancer patients while allowing them to maintain a good quality of life. These antibodies can either regulate proliferation of cancer cells through the manipulation of signal transduction, or promote cytotoxicity. Two examples of FDA-approved mAb-based anticancer drugs are Herceptin and Rituxan (Rituximab), which are currently being used for the treatment of breast cancer and non-Hodgkin's lymphoma, respectively. While there are no mAb-based therapeutics currently available for prostate cancer patients, advanced clinical studies on mAb-based immunotherapy has shown promise for the treatment of prostate cancer including advanced prostate cancer. Despite the major advantages of mAb-based immunotherapy, there are significant pitfalls which may limit its potential. In general, mAb-based therapeutics are highly costly ($70,000 for full course of treatment of Herceptin), lack oral bioavailability, and can lead to severe and often fatal side-effects. For example, Herceptin is associated with heart problems and cannot be administered to approximately 10% of cancer patients because of heart-related complications. Rituxan can cause several side-effects which include renal failure, infections and immune and pulmonary toxicity.

Although still in its infancy, the concept of using small molecules to template the human immune response has shown realistic potential. Recent reports have surfaced in which small molecules have been used to direct antibodies to cancerous cells such as breast carcinoma cells, melanoma cells, and nasopharyngeal epidermal carcinoma cells. Animal studies have demonstrated that these molecules can promote tumor rejection and antitumor immunity in mice. Because this process allows for the direction of endogenous antibodies selectively to the cell of interest, it has the potential to harness the power of mAb-based therapeutics while limiting the costs and side effects associated with administering exogenous antibodies. By developing similar methods which recruit anti-DNP antibodies to prostate cancer cells, the proposed research will help broaden this field while creating a new therapy for all forms of prostate cancer.

OBJECTS OF THE INVENTION

Figure 1:
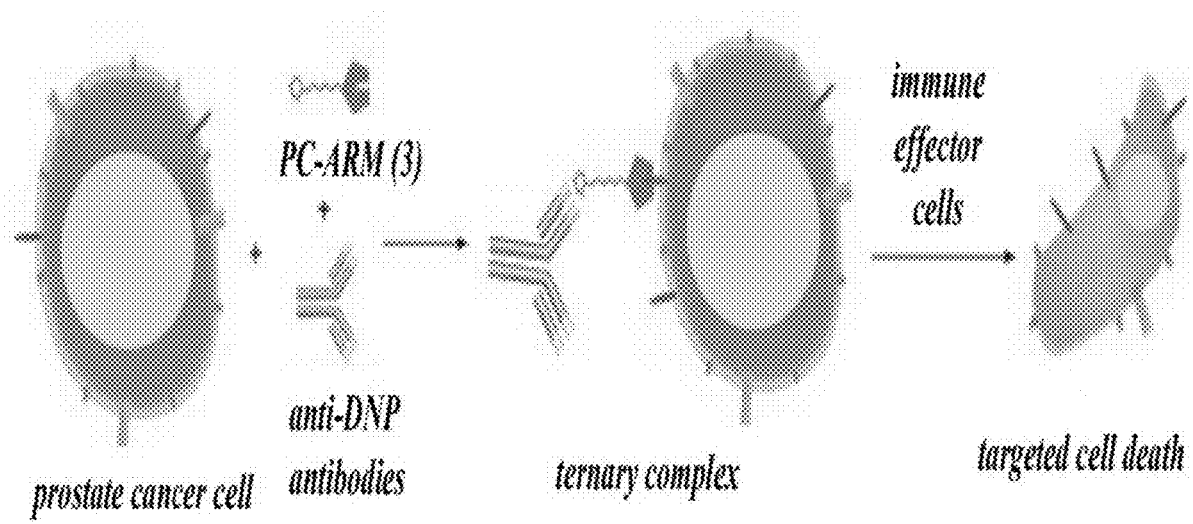
FIG. 1 shows scheme 1, which is a schematic depiction of small-molecule templated immunotherapy.

It is an object of the invention to provide chimeric compounds which can be used to treat virtually any cancer, especially including prostate cancer and metastatic prostate cancer.

It is an additional object of the invention to provide chimeric compounds which can be used to provide pharmaceutical compositions, including pharmaceutical compositions which include additional bioactive agents or agents which assist in the treatment of cancer, especially prostate cancer, including metastatic prostate cancer.

It is still another object of the invention to provide methods for treating cancer, including prostate cancer, including metastatic prostate cancer.

Yet a further object of the invention is to provide methods for inhibiting metastatis of cancer, especially including metastatic prostate cancer.

These and/or other objects of the invention may be readily gleaned from a review of the invention as described herein.

BRIEF DESCRIPTION OF THE INVENTION

It is an aspect of the invention to provide chimeric antibody recruiting molecules which bind to prostate specific membrane antigen (PMSA) and attract antibodies such that the chimeric molecules will assist in immunotherapy of a patient with virtually any cancer, especially including prostate cancer, and further including metastatic prostate cancer.

In this first aspect of the invention, chimeric antibody recruiting molecules are represented by the formula:

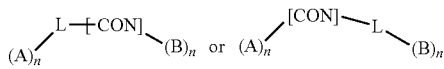

Wherein A is an antibody binding moiety comprising a hapten which is capable of binding to an antibody in a patient;
B is a cell binding moiety capable of binding to prostate specific membrane antigen on the cell surface of cells in said patient;
L is a linker molecule which links [CON] to A or B in a molecule;
[CON] is a bond or a connector molecule linking said linker molecule to A or B; and Each n in a molecule is independently an integer from 1 to 15, 1 to 10, 1 to 5, 1 to 3, 2 to 3, 2 to 5,
Or a pharmaceutically acceptable salt, solvate or polymorph thereof.

In an additional aspect of the invention, a pharmaceutical composition comprises an effective amount of a chimeric compound as described above, optionally and preferably in combination with a pharmaceutically acceptable carrier, additive or excipient. In alternative aspects, pharmaceutical combination compositions comprise an effective amount of a chimeric compound as described herein, in combination with at least one additional agent which is used to treat cancer, including prostate cancer, especially including metastatic prostate cancer or a secondary condition or effect of cancer, especially prostate cancer (e.g., bone pain, hyperplasia, osteoporosis, etc. as otherwise described herein).

In a further aspect of the invention, compounds according to the present invention are used to treat cancer in a patient, especially prostate cancer in male patients in need thereof. The method of treating cancer comprises administering to a patient in need an effective amount of a chimeric compound as otherwise described herein in combination with a pharmaceutically acceptable carrier, additive or excipient, optionally in further combination with at least one additional agent which is effective in treating cancer, especially including prostate cancer, metastatic cancer or one or more of its secondary conditions or effects.

The present invention also relates to a method for inhibiting prostate cancer to reduce or inhibit the spread or metastasis of the cancer into other tissues of the patients' body, especially including bones, the lymph (lymph nodes) system, bladder, vas deferens, kidneys, liver, lungs and brain, among others.

The present invention also relates to instances in which destruction of non-cancerous cells which possess PSMA can be of therapeutic use, especially in cancer therapy. For example, given that PSMA is found on the neovasculare of many non-prostatic cancer cells, but not on normal vasculature, the invention could be used for antiangiogenic therapy for other forms of cancer by targeting the neovasculature of those cancers.

DETAILED DESCRIPTION OF THE INVENTION

The following terms are used to describe the present invention. In instances where a term is not specifically defined herein, that term is given an art-recognized meaning by those of ordinary skill applying that term in context to its use in describing the present invention.

The term "compound", as used herein, unless otherwise indicated, refers to any specific chemical compound disclosed herein and includes tautomers, regioisomers, geometric isomers, and where applicable, optical isomers (enantiomers) thereof, as well as pharmaceutically acceptable salts and derivatives (including prodrug forms) thereof. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents, linkers and connector molecules and variables associated with same, among others, are described. It is understood by those of ordinary skill that molecules which are described herein are stable compounds as generally described hereunder.

The term "patient" or "subject" is used throughout the specification within context to describe an animal, generally a mammal and preferably a human, to whom treatment, including prophylactic treatment (prophylaxis), with the compositions according to the present invention is provided. For treatment of those infections, conditions or disease states which are specific for a specific animal such as a human patient or a patient of a particular gender, such as a human male patient, the term patient refers to that specific animal. Compounds according to the present invention are useful for the treatment of cancer, especially including prostate cancer and in particular, metastatic prostate cancer.

The term "effective" is used herein, unless otherwise indicated, to describe an amount of a compound or composition which, in context, is used to produce or effect an intended result, whether that result relates to the inhibition of the effects of a toxicant on a subject or the treatment of a subject for secondary conditions, disease states or manifestations of exposure to toxicants as otherwise described herein. This term subsumes all other effective amount or effective concentration terms (including the term "therapeutically effective") which are otherwise described in the present application.

The terms "treat", "treating", and "treatment", etc., as used herein, refer to any action providing a benefit to a patient at risk for prostate cancer or metastasis of prostate cancer, including improvement in the condition through lessening or suppression of at least one symptom, inhibition of cancer growth, reduction in cancer cells or tissue, prevention or delay in progression of metastasis of the cancer, prevention or delay in the onset of disease states or conditions which occur secondary to cancer or remission or cure of the cancer, among others. Treatment, as used herein, encompasses both prophylactic and therapeutic treatment.

The term "prophylactic" when used, means to reduce the likelihood of an occurrence or the severity of an occurrence within the context of the treatment of cancer, including cancer metastasis as otherwise described hereinabove.

The term "neoplasia" or "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors. Representative cancers include, for example, prostate cancer, metastatic prostate cancer, stomach, colon, rectal, liver, pancreatic, lung, breast, cervix uteri, corpus uteri, ovary, testis, bladder, renal, brain/CNS, head and neck, throat, Hodgkin's disease, non-Hodgkin's lymphoma, multiple myeloma, leukemia, melanoma, non-melanoma skin cancer, acute lymphocytic leukemia, acute myelogenous leukemia, Ewing's sarcoma, small cell lung cancer, choriocarcinoma, rhabdomyosarcoma, Wilms' tumor, neuroblastoma, hairy cell leukemia, mouth/pharynx, oesophagus, larynx, kidney cancer and lymphoma, among others, which may be treated by one or more compounds according to the present invention. Because of the activity of the present compounds as anti-angiogenic compounds, the present invention has general applicability treating virtually any cancer in any tissue, thus the compounds, compositions and methods of the present invention are generally applicable to the treatment of cancer. Given that the protein target is found on the neovasculature of most non-prostatic cancer cells, the compounds in the present invention may also serve as an antiangiogenic therapy for other cancer types.

In certain particular aspects of the present invention, the cancer which is treated is prostate cancer or metastatic prostate cancer. Separately, metastatic prostate cancer may be found in virtually all tissues of a cancer patient in late stages of the disease, typically metastatic prostate cancer is found in seminal vesicles, lymph system/nodes (lymphoma), in bones, in bladder tissue, in kidney tissue, liver tissue and in virtually any tissue, including brain (brain cancer/tumor). Thus, the present invention is generally applicable and may be used to treat any cancer in any tissue, regardless of etiology.

The term "prostate cancer" is used to describe a disease in which cancer develops in the prostate, a gland in the male reproductive system. It occurs when cells of the prostate mutate and begin to multiply uncontrollably. These cells may metastasize (metastatic prostate cancer) from the prostate to virtually any other part of the body, particularly the bones and lymph nodes, but the kidney, bladder and even the brain, among other tissues. Prostate cancer may cause pain, difficulty in urinating, problems during sexual intercourse, erectile dysfunction. Other symptoms can potentially develop during later stages of the disease.

Rates of detection of prostate cancers vary widely across the world, with South and East Asia detecting less frequently than in Europe, and especially the United States. Prostate cancer develops most frequently in men over the age of fifty and is one of the most prevalent types of cancer in men.

However, many men who develop prostate cancer never have symptoms, undergo no therapy, and eventually die of other causes. This is because cancer of the prostate is, in most cases, slow-growing, and because most of those affected are over the age of 60. Hence, they often die of causes unrelated to the prostate cancer. Many factors, including genetics and diet, have been implicated in the development of prostate cancer. The presence of prostate cancer may be indicated by symptoms, physical examination, prostate specific antigen (PSA), or biopsy. There is concern about the accuracy of the PSA test and its usefulness in screening. Suspected prostate cancer is typically confirmed by taking a biopsy of the prostate and examining it under a microscope. Further tests, such as CT scans and bone scans, may be performed to determine whether prostate cancer has spread.

Treatment options for prostate cancer with intent to cure are primarily surgery and radiation therapy. Other treatments such as hormonal therapy, chemotherapy, proton therapy, cryosurgery, high intensity focused ultrasound (HIFU) also exist depending on the clinical scenario and desired outcome.

The age and underlying health of the man, the extent of metastasis, appearance under the microscope, and response of the cancer to initial treatment are important in determining the outcome of the disease. The decision whether or not to treat localized prostate cancer (a tumor that is contained within the prostate) with curative intent is a patient trade-off between the expected beneficial and harmful effects in terms of patient survival and quality of life.

An important part of evaluating prostate cancer is determining the stage, or how far the cancer has spread. Knowing the stage helps define prognosis and is useful when selecting therapies. The most common system is the four-stage TNM system (abbreviated from Tumor/Nodes/Metastases). Its components include the size of the tumor, the number of involved lymph nodes, and the presence of any other metastases.

The most important distinction made by any staging system is whether or not the cancer is still confined to the prostate or is metastatic. In the TNM system, clinical T1 and T2 cancers are found only in the prostate, while T3 and T4 cancers have spread elsewhere and metastasized into other tissue. Several tests can be used to look for evidence of spread. These include computed tomography to evaluate spread within the pelvis, bone scans to look for spread to the bones, and endorectal coil magnetic resonance imaging to closely evaluate the prostatic capsule and the seminal vesicles. Bone scans often reveal osteoblastic appearance due to increased bone density in the areas of bone metastasis—opposite to what is found in many other cancers that metastasize. Computed tomography (CT) and magnetic resonance imaging (MRI) currently do not add any significant information in the assessment of possible lymph node metastases in patients with prostate cancer according to a meta-analysis.

Prostate cancer is relatively easy to treat if found early. After a prostate biopsy, a pathologist looks at the samples under a microscope. If cancer is present, the pathologist reports the grade of the tumor. The grade tells how much the tumor tissue differs from normal prostate tissue and suggests how fast the tumor is likely to grow. The Gleason system is used to grade prostate tumors from 2 to 10, where a Gleason score of 10 indicates the most abnormalities. The pathologist assigns a number from 1 to 5 for the most common pattern observed under the microscope, then does the same for the second most common pattern. The sum of these two numbers is the Gleason score. The Whitmore-Jewett stage is another method sometimes used. Proper grading of the tumor is critical, since the grade of the tumor is one of the major factors used to determine the treatment recommendation.

Early prostate cancer usually causes no symptoms. Often it is diagnosed during the workup for an elevated PSA noticed during a routine checkup. Sometimes, however, prostate cancer does cause symptoms, often similar to those of diseases such as benign prostatic hypertrophy. These include frequent urination, increased urination at night, difficulty starting and maintaining a steady stream of urine, blood in the urine, and painful urination. Prostate cancer is associated with urinary dysfunction as the prostate gland surrounds the prostatic urethra. Changes within the gland therefore directly affect urinary function. Because the vas deferens deposits seminal fluid into the prostatic urethra, and secretions from the prostate gland itself are included in semen content, prostate cancer may also cause problems with sexual function and performance, such as difficulty achieving erection or painful ejaculation.

Advanced prostate cancer can spread to other parts of the body and this may cause additional symptoms. The most common symptom is bone pain, often in the vertebrae (bones of the spine), pelvis or ribs. Spread of cancer into other bones such as the femur is usually to the proximal part of the bone. Prostate cancer in the spine can also compress the spinal cord, causing leg weakness and urinary and fecal incontinence.

The specific causes of prostate cancer remain unknown. A man's risk of developing prostate cancer is related to his age, genetics, race, diet, lifestyle, medications, and other factors. The primary risk factor is age. Prostate cancer is uncommon in men less than 45, but becomes more common with advancing age. The average age at the time of diagnosis is 70. However, many men never know they have prostate cancer.

A man's genetic background contributes to his risk of developing prostate cancer. This is suggested by an increased incidence of prostate cancer found in certain racial groups, in identical twins of men with prostate cancer, and in men with certain genes. Men who have a brother or father with prostate cancer have twice the usual risk of developing prostate cancer. Studies of twins in Scandinavia suggest that forty percent of prostate cancer risk can be explained by inherited factors. However, no single gene is responsible for prostate cancer; many different genes have been implicated. Two genes (BRCA1 and BRCA2) that are important risk factors for ovarian cancer and breast cancer in women have also been implicated in prostate cancer.

Dietary amounts of certain foods, vitamins, and minerals can contribute to prostate cancer risk. Dietary factors that may increase prostate cancer risk include low intake of vitamin E, the mineral selenium, green tea and vitamin D. A large study has implicated dairy, specifically low-fat milk and other dairy products to which vitamin A palmitate has been added. This form of synthetic vitamin A has been linked to prostate cancer because it reacts with zinc and protein to form an unabsorbable complex. Prostate cancer has also been linked to the inclusion of bovine somatotropin hormone in certain dairy products.

There are also some links between prostate cancer and medications, medical procedures, and medical conditions. Daily use of anti-inflammatory medicines such as aspirin, ibuprofen, or naproxen may decrease prostate cancer risk. Use of the cholesterol-lowering drugs known as the statins may also decrease prostate cancer risk. Infection or inflammation of the prostate (prostatitis) may increase the chance for prostate cancer, and infection with the sexually transmitted infections chlamydia, gonorrhea, or syphilis seems to increase risk. Obesity and elevated blood levels of testosterone may increase the risk for prostate cancer.

Prostate cancer is classified as an adenocarcinoma, or glandular cancer, that begins when normal semen-secreting prostate gland cells mutate into cancer cells. The region of prostate gland where the adenocarcinoma is most common is the peripheral zone. Initially, small clumps of cancer cells remain confined to otherwise normal prostate glands, a condition known as carcinoma in situ or prostatic intraepithelial neoplasia (PIN). Although there is no proof that PIN is a cancer precursor, it is closely associated with cancer. Over time these cancer cells begin to multiply and spread to the surrounding prostate tissue (the stroma) forming a tumor. Eventually, the tumor may grow large enough to invade nearby organs such as the seminal vesicles or the rectum, or the tumor cells may develop the ability to travel in the bloodstream and lymphatic system. Prostate cancer is considered a malignant tumor because it is a mass of cells which can invade other parts of the body. This invasion of other organs is called metastasis. Prostate cancer most commonly metastasizes to the bones, lymph nodes, rectum, and bladder.

In prostate cancer, the regular glands of the normal prostate are replaced by irregular glands and clumps of cells. When a man has symptoms of prostate cancer, or a screening test indicates an increased risk for cancer, more invasive evaluation is offered. The only test which can fully confirm the diagnosis of prostate cancer is a biopsy, the removal of small pieces of the prostate for microscopic examination. However, prior to a biopsy, several other tools may be used to gather more information about the prostate and the urinary tract. Cystoscopy shows the urinary tract from inside the bladder, using a thin, flexible camera tube inserted down the urethra. Transrectal ultrasonography creates a picture of the prostate using sound waves from a probe in the rectum.

After biopsy, the tissue samples are then examined under a microscope to determine whether cancer cells are present, and to evaluate the microscopic features (or Gleason score) of any cancer found. In addition, tissue samples may be stained for the presence of PSA and other tumor markers in order to determine the origin of maligant cells that have metastasized. A number of other potential approaches for diagnosis of prostate cancer are ongoing such as early prostate cancer antigen-2 (EPCA-2), and prostasome analysis.

In addition to therapy using the compounds according to the present invention, therapy (including prophylactic therapy) for prostate cancer supports roles in reducing prostate cancer for dietary selenium, vitamin E, lycopene, soy foods, vitamin D, green tea, omega-3 fatty acids and phytoestrogens. The selective estrogen receptor modulator drug toremifene has shown promise in early trials. Two medications which block the conversion of testosterone to dihydrotestosterone (and reduce the tendency toward cell growth), finasteride and dutasteride, are shown to be useful. The phytochemicals indole-3-carbinol and diindolylmethane, found in cruciferous vegetables (califlower and broccholi), have favorable antiandrogenic and immune modulating properties. Prostate cancer risk is decreased in a vegetarian diet.

Treatment for prostate cancer may involve active surveillance, surgery (prostatecomy or orchiectomy), radiation therapy including brachytherapy (prostate brachytherapy) and external beam radiation as well as hormonal therapy. There are several forms of hormonal therapy which include the following, each of which may be combined with compounds according to the present invention.

- Antiandrogens such as flutamide, bicalutamide, nilutamide, and cyproterone acetate which directly block the actions of testosterone and DHT within prostate cancer cells.
- Medications such as ketoconazole and aminoglutethimide which block the production of adrenal androgens such as DHEA. These medications are generally used only in combination with other methods that can block the 95% of androgens made by the testicles. These combined methods are called total androgen blockade (TAB), which can also be achieved using antiandrogens.
- GnRH modulators, including agonists and antagonists. GnRH antagonists suppress the production of LH directly, while GnRH agonists suppress LH through the process of downregulation after an initial stimulation effect. Abarelix is an example of a GnRH antagonist, while the GnRH agonists include leuprolide, goserelin, triptorelin, and buserelin.
- The use of abiraterone acetate can be used to reduce PSA levels and tumor sizes in aggressive end-stage prostate cancer for as high as 70% of patients. Sorafenib may also be used to treat metastatic prostate cancer.

Each treatment described above has disadvantages which limit its use in certain circumstances. GnRH agonists eventually cause the same side effects as orchiectomy but may cause worse symptoms at the beginning of treatment. When GnRH agonists are first used, testosterone surges can lead to increased bone pain from metastatic cancer, so antiandrogens or abarelix are often added to blunt these side effects. Estrogens are not commonly used because they increase the risk for cardiovascular disease and blood clots. The antiandrogens do not generally cause impotence and usually cause less loss of bone and muscle mass. Ketoconazole can cause liver damage with prolonged use, and aminoglutethimide can cause skin rashes.

Palliative care for advanced stage prostate cancer focuses on extending life and relieving the symptoms of metastatic disease. As noted above, abiraterone acetate shows some promise in treating advance stage prostate cancer as does sorafenib. Chemotherapy may be offered to slow disease progression and postpone symptoms. The most commonly used regimen combines the chemotherapeutic drug docetaxel with a corticosteroid such as prednisone. Bisphosphonates such as zoledronic acid have been shown to delay skeletal complications such as fractures or the need for radiation therapy in patients with hormone-refractory metastatic prostate cancer. Alpharadin may be used to target bone metastasis. The phase II testing shows prolonged patient survival times, reduced pain and improved quality of life.

Bone pain due to metastatic disease is treated with opioid pain relievers such as morphine and oxycodone. External beam radiation therapy directed at bone metastases may provide pain relief. Injections of certain radioisotopes, such as strontium-89, phosphorus-32, or samarium-153, also target bone metastases and may help relieve pain.

As an alternative to active surveillance or definitive treatments, alternative therapies may also be used for the management of prostate cancer. PSA has been shown to be lowered in men with apparent localized prostate cancer using a vegan diet (fish allowed), regular exercise, and stress reduction. Many other single agents have been shown to reduce PSA, slow PSA doubling times, or have similar effects on secondary markers in men with localized cancer in short term trials, such as pomegranate juice or genistein, an isoflavone found in various legumes.

Manifestations or secondary conditions or effects of metastatic and advanced prostate cancer may include anemia, bone marrow suppression, weight loss, pathologic fractures, spinal cord compression, pain, hematuria, ureteral and/or bladder outlet obstruction, urinary retention, chronic renal failure, urinary incontinence, and symptoms related to bony or soft-tissue metastases, among others.

Additional prostate drugs which can be used in combination with the chimeric antibody recruiting compounds according to the present invention include, for example, the enlarged prostate drugs/agents, as well as eulexin, flutamide, goserelin, leuprolide, lupron, nilandron, nilutamide, zoladex and mixtures thereof. Enlarged prostate drugs/agents as above, include for example, ambenyl, ambophen, amgenal, atrosept, bromanyl, bromodiphenhydramine-codeine, bromotuss-codeine, cardura, chlorpheniramine-hydrocodone, ciclopirox, clotrimazole-betamethasone, dolsed, dutasteride, finasteride, flomax, gecil, hexalol, lamisil, lanased, loprox, lotrisone, methenamine, methen-bella-meth Bl-phen sal, meth-hyos-atrp-M blue-BA-phsal, MHP-A, mybanil, prosed/DS, Ro-Sed, S-T Forte, tamsulosin, terbinafine, trac, tussionex, ty-methate, uramine, uratin, uretron, uridon, uroves, urstat, usept and mixtures thereof.

The term "tumor" is used to describe a malignant or benign growth or tumefacent.

The term "antibody binding terminal moiety", "antibody binding terminus" or "antibody binding moiety" is use to described that portion of a chimeric compound according to the present invention which comprises at least one small molecule or hapten. The term "hapten" is used to describe a small-molecular-weight inorganic or organic molecule that alone is not antigenic but which when linked to another molecule, such as a carrier protein (albumin, etc.) or in the case of the present invention, a cell binding terminal moiety of the present compounds is antigenic; and an antibody raised against the hapten (generally, the hapten bonded or complexed to the carrier) will react with the hapten alone.

It is preferred that the antibody binding terminal comprise a hapten which is reactive (binds to) an endogenous antibody that pre-exists in the patient prior to initiating therapy with the compounds of the present invention and does not have to be separately raised as part of a treatment regimen. Thus, haptens which comprise a di- or trinitro phenyl group as depicted below, or a digalactose hapten (Gal-Gal-Z, preferably Gal-Gal-sugar, preferably Gal-Gal-Glu), are preferred. Additionally, a compound according to the general structure:

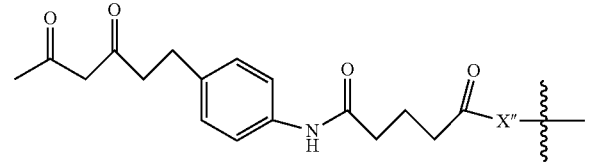

Where X" is O, $CH_2$, $NR^1$, S; and $R^1$ is H, a $C_1$-$C_3$ alkyl group or a —$C(O)(C_1$-$C_3)$ group;
May be used as haptens in the present invention.

Further, a moiety according to the chemical structure:

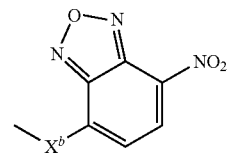

Where $X^b$ is a bond, O, $CH_2$, $NR^1$ or S may also be used as a hapten (ABT) in the present invention.

The di- or trinitro phenyl hapten (ABT) moiety for use in the present invention may be represented by the following formula:

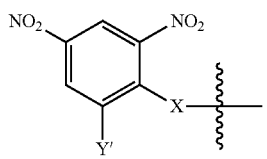

Where Y' is H or $NO_2$;
X is O, $CH_2$, NR', S(O), $S(O)_2$, $-S(O)_2O$, $-OS(O)_2$, or $OS(O)_2O$;
$R^1$ is H, a $C_1$-$C_3$ alkyl group, or a $-C(O)(C_1$-$C_3)$ group;

The (Gal-Gal-Z) hapten is represented by the chemical formula:

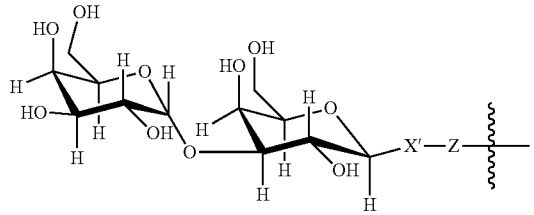

Where X' is $CH_2$, O, N—$R^{1'}$, or S, preferably O;
$R^{1'}$ is H or $C_1$-$C_3$ alkyl;
Where Z is a bond, a monosaccharide, disaccharide, oligosaccharide, glycoprotein or glycolipid, preferably a sugar group, more preferably a sugar group selected from the monosaccharides, including aldoses and ketoses, and disaccharides, including those disaccharides described herein. Monosaccharide aldoses include monosaccharides such as aldotriose (D-glyceraldehdye, among others), aldotetroses (D-erythrose and D-Threose, among others), aldopentoses, (D-ribose, D-arabinose, D-xylose, D-lyxose, among others), aldohexoses (D-allose, D-altrose, D-Glucose, D-Mannose, D-gulose, D-idose, D-galactose and D-Talose, among others), and the monosaccharide ketoses include monosaccharides such as ketotriose (dihydroxyacetone, among others), ketotetrose (D-erythrulose, among others), ketopentose (D-ribulose and D-xylulose, among others), ketohexoses (D-Psicone, D-Fructose, D-Sorbose, D-Tagatose, among others), aminosugars, including galactoseamine, sialic acid, N-acetylglucosamine, among others and sulfosugars, including sulfoquinovose, among others. Exemplary disaccharides which find use in the present invention include sucrose (which may have the glucose optionally N-acetylated), lactose (which may have the galactose and/or the glucose optionally N-acetylated), maltose (which may have one or both of the glucose residues optionally N-acetylated), trehalose (which may have one or both of the glucose residues optionally N-acetylated), cellobiose (which may have one or both of the glucose residues optionally N-acetylated), kojibiose (which may have one or both of the glucose residues optionally N-acetylated), nigerose (which may have one or both of the glucose residues optionally N-acetylated), isomaltose (which may have one or both of the glucose residues optionally N-acetylated), β,β-trehalose (which may have one or both of the glucose residues optionally N-acetylated), sophorose (which may have one or both of the glucose residues optionally N-acetylated), laminaribiose (which may have one or both of the glucose residues optionally N-acetylated), gentiobiose (which may have one or both of the glucose residues optionally N-acetylated), turanose (which may have the glucose residue optionally N-acetylated), maltulose (which may have the glucose residue optionally N-acetylated), palatinose (which may have the glucose residue optionally N-acetylated), gentiobiluose (which may have the glucose residue optionally N-acetylated), mannobiose, melibiose (which may have the glucose residue and/or the galactose residue optionally N-acetylated), melibiulose (which may have the galactose residue optionally N-acetylated), rutinose, (which may have the glucose residue optionally N-acetylated), rutinulose and xylobiose, among others. Oligosaccharides for use in the present invention as Z can include any sugar of three or more (up to about 100) individual sugar (saccharide) units as described above (i.e., any one or more saccharide units described above, in any order, especially including glucose and/or galactose units as set forth above), or for example, fructo-oligosaccharides, galactooligosaccharides and mannan-oligosaccharides ranging from three to about ten-fifteen sugar units in size. Glycoproteins for use in the present invention include, for example, N-glycosylated and O-glycosylated glycoproteins, including the mucins, collagens, transferring, ceruloplasmin, major histocompatability complex proteins (MHC), enzymes, lectins and selectins, calnexin, calreticulin, and integrin glycoprotein IIb/IIa, among others. Glycolipids for use in the present invention include, for example, glyceroglycolipids (galactolipids, sulfolipids), glycosphingolipids, such as cerebrosides, galactocerebrosides, glucocerebrosides (including glucobicaranateoets), gangliosides, globosides, sulfatides, glycophosphphingolipids and glycocalyx, among others.

Preferably, Z is a bond (linking a Gal-Gal disaccharide to a linker or connector molecule) or a glucose or glucosamine (especially N-acetylglucosamine). It is noted that Z is linked to a galactose residue through a hydroxyl group or an amine group on the galactose of Gal-Gal, preferably a hydroxyl group. A preferred hapten is Gal-Gal-Glu which is represented by the structure:

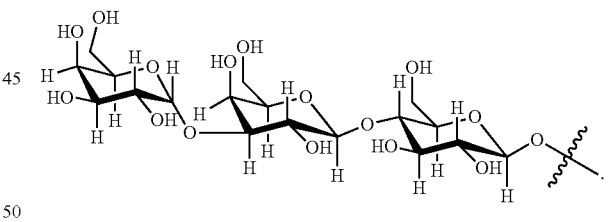

The term "cell binding terminal moiety", "cell binding terminus" or "cell binding moiety" is use to described that portion of a chimeric compound according to the present invention which comprises at least one small molecule or moiety which can bind specifically to prostate specific membrane antigen (PSMA).

Preferred CBT groups for use in the present invention are set forth below:

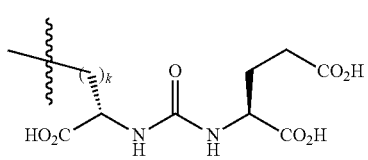

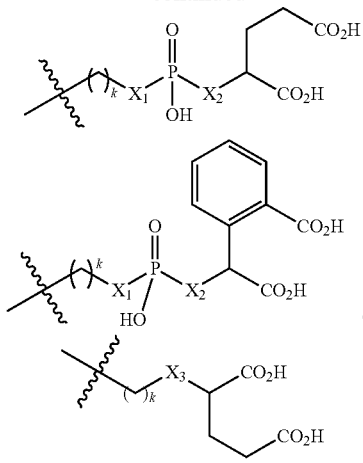

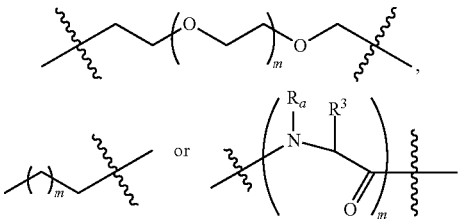

Where $X_1$ and $X_2$ are each independently $CH_2$, O, NH or S; $X_3$ is O, $CH_2$, NR', S(O), $S(O)_2$, $-S(O)_2O$, $-OS(O)_2$, or $OS(O)_2O$;

$R^1$ is H, a $C_1$-$C_3$ alkyl group, or a $-C(O)(C_1$-$C_3)$ group;

k is an integer from 0 to 20, 8 to 12, 1 to 15, 1 to 10, 1 to 8, 1 to 6, 1, 2, 3, 4, 5 or 6; or a salt thereof.

The term "linker" refers to a chemical entity connecting an antibody binding terminus (ABT) moiety to a cell binding terminus (CBT) moiety, optionally through a connector moiety through covalent bonds. The linker between the two active portions of the molecule, that is the antibody binding terminus (ABT) and the cell binding terminus (CBT) ranges from about 5 Å to about 50 Å or more in length, about 6 Å to about 45 Å in length, about 7 Å to about 40 Å in length, about 8 Å to about 35 Å in length, about 9 Å to about 30 Å in length, about 10 Å to about 25 Å in length, about 7 Å to about 20 Å in length, about 5 Å to about 16 Å in length, about 5 Å to about 15 Å in length, about 6 Å to about 14 Å in length, about 10 Å to about 20 Å in length, about 1 IA to about 25 Å in length, etc. Linkers which are based upon ethylene glycol units and are between 8 and 12 glycol units in length may be preferred. By having a linker with a length as otherwise disclosed herein, the ABT moiety and the CBT moiety may be situated to advantageously take advantage of the biological activity of compounds according to the present invention which bind to prostate specific membrane antigen (PSMA) and attractive endogenous antibodies to the cell to which the compounds are bound, resulting in the selective and targeted cell death of those cells, in whatever tissues they may reside, which have PSMA. The selection of a linker component is based on its documented properties of biocompatibility, solubility in aqueous and organic media, and low immunogenicity/antigenicity. Although numerous linkers may be used as otherwise described herein, a linker based upon polyethyleneglycol (PEG) linkages, polypropylene glycol linkages, or polyethyleneglycol-co-polypropylene oligomers (up to about 100 units, about 1 to 100, about 1 to 75, about 1 to 60, about 1 to 50, about 1 to 35, about 1 to 25, about 1 to 20, about 1 to 15, 1 to 10, about 8 to 12, about 1 to 8, etc.) may be favored as a linker because of the chemical and biological characteristics of these molecules. The use of polyethylene (PEG) linkages is preferred.

Preferred linkers include those according to the chemical structures:

Or a polypropylene glycol or polypropylene-co-polyethylene glycol linker having between 1 and 100 glycol units;

Where $R_a$ is H, $C_1$-$C_3$ alkyl or alkanol or forms a cyclic ring with $R^3$ (proline) and $R^3$ is a side chain derived of an amino acid preferably selected from the group consisting of alanine (methyl), arginine (propyleneguanidine), asparagine (methylenecarboxyamide), aspartic acid (ethanoic acid), cysteine (thiol, reduced or oxidized di-thiol), glutamine (ethylcarboxyamide), glutamic acid (propanoic acid), glycine (H), histidine (methyleneimidazole), isoleucine (1-methylpropane), leucine (2-methylpropane), lysine (butyleneamine), methionine (ethylmethylthioether), phenylalanine (benzyl), proline ($R^3$ forms a cyclic ring with $R_a$ and the adjacent nitrogen group to form a pyrrolidine group), serine (methanol), threonine (ethanol, 1-hydroxyethane), tryptophan (methyleneindole), tyrosine (methylene phenol) or valine (isopropyl);

m is an integer from 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5; or A linker according to the chemical formula:

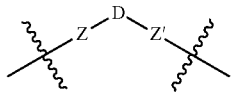

Where Z and Z' are each independently a bond, $-(CH_2)_i-$O, $-(CH_2)_i-$S, $-(CH_2)_i-$N$-$R,

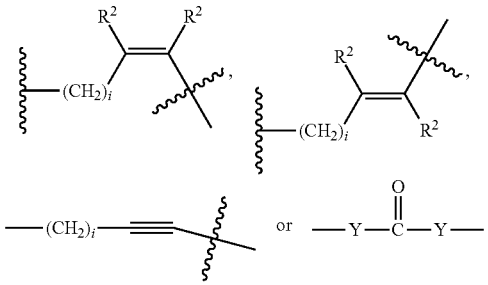

wherein said $-(CH_2)_i$ group, if present in Z or Z', is bonded to a connector, ABT or CBT;

Each R is H, or a $C_1$-$C_3$ alkyl or alkanol group;

Each $R^2$ is independently H or a $C_1$-$C_3$ alkyl group;

Each Y is independently a bond, O, S or N$-$R;

Each i is independently 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

D is

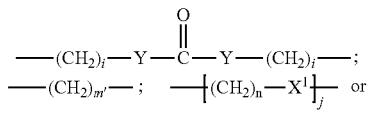

or a bond, with the proviso that Z, Z' and D are not each simultaneously bonds;

j is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

m' is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

n is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

$X^1$ is O, S or N—R; and

R is as described above, or a pharmaceutical salt thereof.

The term "connector", symbolized by [CON], is used to describe a chemical moiety which is optionally included in chimeric compounds according to the present invention which forms from the reaction product of an activated ABT-linker with a CBT moiety (which also is preferably activated) or an ABT moiety with an activated linker-CBT as otherwise described herein. The connector group is the resulting moiety which forms from the facile condensation of two separate chemical fragments which contain reactive groups which can provide connector groups as otherwise described to produce chimeric compounds according to the present invention. It is noted that a connector may be distinguishable from a linker in that the connector is the result of a specific chemistry which is used provide chimeric compounds according to the present invention wherein the reaction product of these groups results in an identifiable connector group which is distinguishable from the linker group as otherwise described herein. It is noted that there may be some overlap between the description of the connector group and the linker group, especially with respect to more common connector groups such as amide groups, oxygen (ether), sulfur (thioether) or amine linkages, urea or carbonate —OC(O)O— groups as otherwise described herein. It is further noted that a connector (or linker) may be connected to ABT, a linker or CBT at positions which are represented as being linked to another group using the using the symbol

Where two or more such groups are present in a linker or connector, any of an ABT, a linker or a CBT may be bonded to such a group.

Common connector groups which are used in the present invention include the following chemical groups:

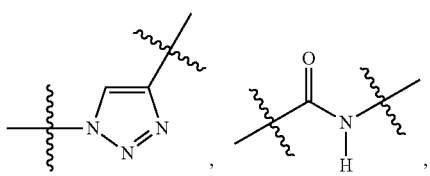

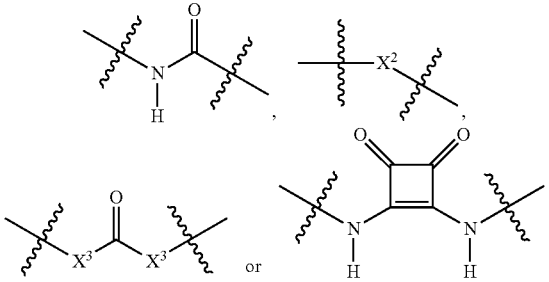

Where $X^2$ is O, S, $NR^4$, S(O), $S(O)_2$, —$S(O)_2O$, —$OS(O)_2$, or $OS(O)_2O$;

$X^3$ is O, S, $NR^4$; and $R^4$ is H, a $C_1$-$C_3$ alkyl or alkanol group, or a —C(O)($C_1$-$C_3$) group.

The term "pharmaceutically acceptable salt" or "salt" is used throughout the specification to describe a salt form of one or more of the compositions herein which are presented to increase the solubility of the compound in saline for parenteral delivery or in the gastric juices of the patient's gastrointestinal tract in order to promote dissolution and the bioavailability of the compounds. Pharmaceutically acceptable salts include those derived from pharmaceutically acceptable inorganic or organic bases and acids. Suitable salts include those derived from alkali metals such as potassium and sodium, alkaline earth metals such as calcium, magnesium and ammonium salts, among numerous other acids well known in the pharmaceutical art. Sodium and potassium salts may be preferred as neutralization salts of carboxylic acids and free acid phosphate containing compositions according to the present invention. The term "salt" shall mean any salt consistent with the use of the compounds according to the present invention. In the case where the compounds are used in pharmaceutical indications, including the treatment of prostate cancer, including metastatic prostate cancer, the term "salt" shall mean a pharmaceutically acceptable salt, consistent with the use of the compounds as pharmaceutical agents.

The term "coadministration" shall mean that at least two compounds or compositions are administered to the patient at the same time, such that effective amounts or concentrations of each of the two or more compounds may be found in the patient at a given point in time. Although compounds according to the present invention may be co-administered to a patient at the same time, the term embraces both administration of two or more agents at the same time or at different times, provided that effective concentrations of all coadministered compounds or compositions are found in the subject at a given time. Chimeric antibody-recruiting compounds according to the present invention may be administered with one or more additional anti-cancer agents or other agents which are used to treat or ameliorate the symptoms of cancer, especially prostate cancer, including metastatic prostate cancer. Exemplary anticancer agents which may be coadministered in combination with one or more chimeric compounds according to the present invention include, for example, antimetabolites, inhibitors of topoisomerase I and II, alkylating agents and microtubule inhibitors (e.g., taxol). Specific anticancer compounds for use in the present invention include, for example, Aldesleukin; Alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous;

busulfan oral; calusterone; capecitabine; carboplatin; carmustine; carmustine with Polifeprosan 20 Implant; celecoxib; chlorambucil; cisplatin; cladribine; cyclophosphamide; cytarabine; cytarabine liposomal; dacarbazine; dactinomycin; actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemtuzumab ozogamicin; goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); meclorethamine (nitrogen mustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; oxaliplatin; paclitaxel; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; talbuvidine (LDT); talc; tamoxifen; temozolomide; teniposide (VM-26); testolactone; thioguanine (6-TG); thiotepa; topotecan; toremifene; Tositumomab; Trastuzumab; tretinoin (ATRA); Uracil Mustard; valrubicin; valtorcitabine (monoval LDC); vinblastine; vinorelbine; zoledronate; and mixtures thereof, among others.

In addition to anticancer agents, a number of other agents may be coadministered with chimeric compounds according to the present invention in the treatment of cancer, especially prostate cancer, including metastatic prostate cancer. These include active agents, minerals, vitamins and nutritional supplements which have shown some efficacy in inhibiting prostate cancer tissue or its growth or are otherwise useful in the treatment of prostate cancer. For example, one or more of dietary selenium, vitamin E, lycopene, soy foods, vitamin D, green tea, lycopene, omega-3 fatty acids and phytoestrogens, including beta-sitosterol, may be utilized in combination with the present compounds to treat prostate cancer.

In addition, active agents, other than traditional anticancer agents have shown some utility in treating prostate cancer. The selective estrogen receptor modulator drug toremifene may be used in combination with the present compounds to treat cancer, especially prostate cancer, including metastatic prostate cancer. In addition, two medications which block the conversion of testosterone to dihydrotestosterone, finasteride and dutasteride, are also useful in the treatment of prostate cancer when coadministered with compounds according to the present invention. The phytochemicals indole-3-carbinol and diindolylmethane, may also be coadministered with the present compounds for their effects in treating prostate cancer. Additional agents which may be combined with compounds according to the present invention include antiandrogens, for example, flutamide, bicalutamide, nilutamide, and cyproterone acetate as well as agents which reduce the production of adrenal androgens (e.g. DHEA), such as ketoconazole and aminoglutethimide. Other active agents which may be combined with compounds according to the present invention include, for example, GnRH modulators, including agonists and antagonists. GnRH antagonists suppress the production of LH directly, while GnRH agonists suppress LH through the process of downregulation after an initial stimulation effect. Abarelix is an example of a GnRH antagonist, while the GnRH agonists include leuprolide, goserelin, triptorelin, and buserelin, among others. These agents may be combined with compounds according to the present invention in effective amounts. In addition, abiraterone acetate may also be combined with one or more compounds according to the present invention in the treatment of prostate cancer, especially including metastatic prostate cancer.

Other agents which may be combined with one or more compounds according to the present invention, include the bisphosphonates such as zoledronic acid, which have been shown to delay skeletal complications such as fractures which occur with patients having metastatic prostate cancer. Alpharadin, another agent, may be combined with compounds according to the present invention to target bone metastasis. In addition, bone pain due to metastatic prostate cancer may be treated with opioid pain relievers such as morphine and oxycodone, among others, which may be combined with compounds according to the present invention.

The present invention preferably relates to compounds according to the general chemical structure:

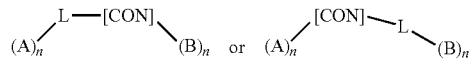

Wherein A is an antibody binding moiety according to the chemical formula:

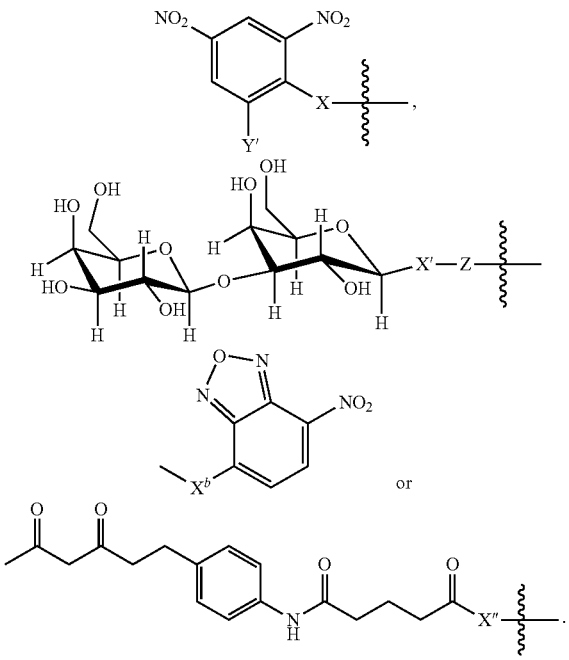

Where Y' is H or $NO_2$;
X is O, $CH_2$, $NR^1$, S(O), $S(O)_2$, —$S(O)_2O$, —$OS(O)_2$, or $OS(O)_2O$;
$R^1$ is H, a $C_1$-$C_3$ alkyl group, or a —$C(O)(C_1$-$C_3)$ group;
X' is $CH_2$, O, N—$R^{1'}$, or S, preferably O;
$R^{1'}$ is H or $C_1$-$C_3$ alkyl;
Z is a bond, a monosaccharide, disaccharide, oligosaccharide, glycoprotein or glycolipid;
$X^b$ is a bond, O, $CH_2$, $NR^1$ or S;
X" is O, $CH_2$, $NR^1$;
$R^1$ is H, a $C_1$-$C_3$ alkyl group or a —$C(O)(C_1$-$C_3)$ group;

B is a cell binding moiety according to the chemical formula:

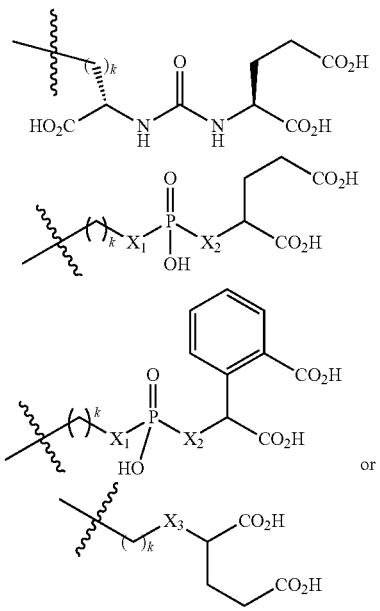

Where $X_1$ and $X_2$ are each independently $CH_2$, O, NH or S; $X_3$ is O, $CH_2$, $NR^1$, S(O), $S(O)_2$, $-S(O)_2O$, $-OS(O)_2$, or $OS(O)_2O$;
$R^1$ is H, a $C_1$-$C_3$ alkyl group, or a $-C(O)(C_1$-$C_3)$ group;
k is an integer from 0 to 20, 8 to 12, 1 to 15, 1 to 10, 1 to 8, 1 to 6, 1, 2, 3, 4, 5 or 6;
L is a linker according to the chemical formula:

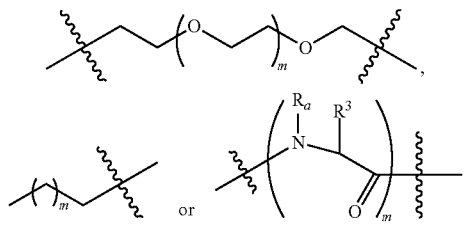

Or a polypropylene glycol or polypropylene-co-polyethylene glycol linker having between 1 and 100 glycol units (1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 52 and 50, 3 and 45);
Where $R_a$ is H, $C_1$-$C_3$ alkyl or alkanol or forms a cyclic ring with $R^3$ (proline) and $R^3$ is a side chain derived of an amino acid preferably selected from the group consisting of alanine (methyl), arginine (propyleneguanidine), asparagine (methylenecarboxyamide), aspartic acid (ethanoic acid), cysteine (thiol, reduced or oxidized di-thiol), glutamine (ethylcarboxyamide), glutamic acid (propanoic acid), glycine (H), histidine (methyleneimidazole), isoleucine (1-methylpropane), leucine (2-methylpropane), lysine (butyleneamine), methionine (ethylmethylthioether), phenylalanine (benzyl), proline ($R^3$ forms a cyclic ring with $R_a$ and the adjacent nitrogen group to form a pyrrolidine group), serine (methanol). threonine (ethanol, 1-hydroxyethane), tryptophan (methyleneindole), tyrosine (methylene phenol) or valine (isopropyl);

m is an integer from 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5; or L is a linker according to the chemical formula:

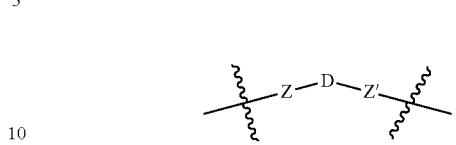

Where Z and Z' are each independently a bond, $-(CH_2)_i-$O, $-(CH_2)_i-$S, $-(CH_2)_i-$N$-$R,

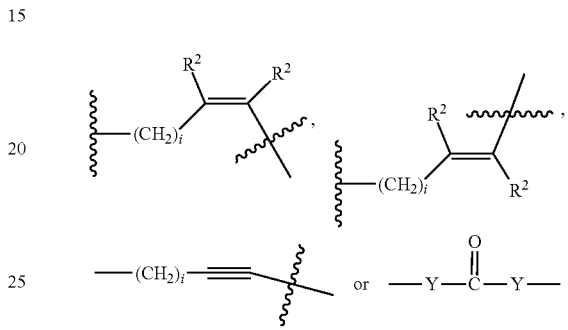

wherein said $-(CH_2)$, group, if present in Z or Z', is bonded to [CON] if present, ABT or CBT;

Each R is independently H, or a $C_1$-$C_3$ alkyl or alkanol group;

Each $R^2$ is independently H or a $C_1$-$C_3$ alkyl group;

Each Y is independently a bond, O, S or N$-$R;

Each i is independently 0 to 100, 1 to 100, 1 to 75, 1 to 60, 1 to 55, 1 to 50. 1 to 45, 1 to 40, 2 to 35, 3 to 30, 1 to 15, 1 to 10, 1 to 8, 1 to 6, 1, 2, 3, 4 or 5;

D is

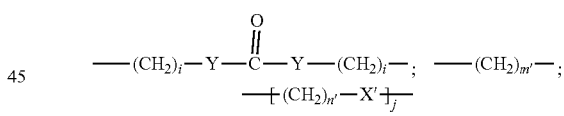

or a bond, with the proviso that Z, Z' and D are not each simultaneously bonds;

j is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

m' is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

n' is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5; and $X^1$ is O, S or N$-$R, R is as described above; and The connector moiety [CON] is a bond or a moiety according to the chemical structure:

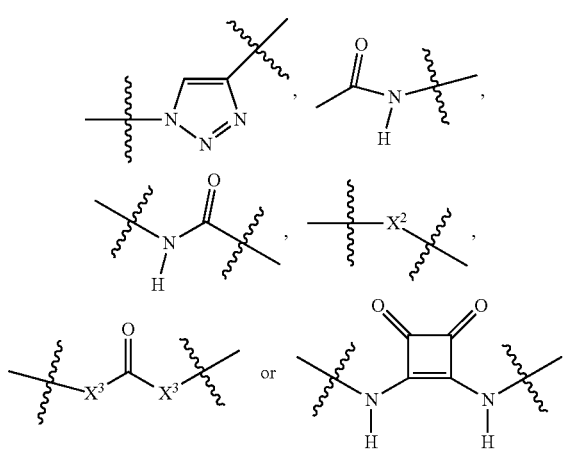

Where $X^2$ is O, S, $NR^4$, S(O), $S(O)_2$, —$S(O)_2$O, —$OS(O)_2$, or $OS(O)_2$O;
$X^3$ is $NR^4$, O or S; and
$R^4$ is H, a $C_1$-$C_3$ alkyl or alkanol group, or a —C(O)($C_1$-$C_3$) group; or
a pharmaceutically acceptable salt, solvate or polymorph thereof.

In preferred aspects of the invention, the antibody binding terminus (ABT) is

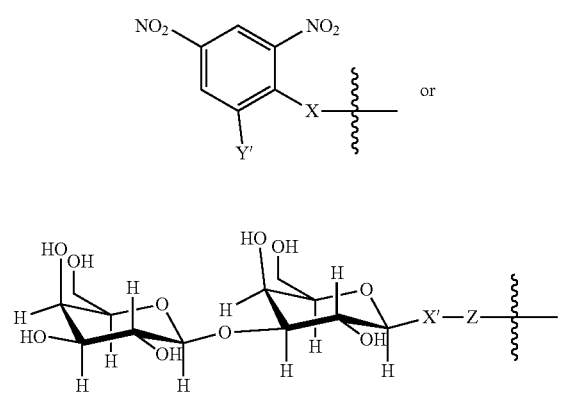

Y' is $NO_2$;
X' is O;
Z is a bond, a monosaccharide or a disaccharide.

In preferred aspects of the invention, CBT is

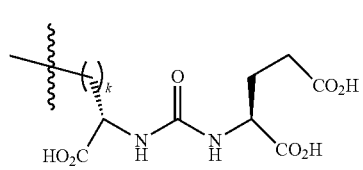

Where k is an integer from 0 to 20, 1 to 20, more preferably 8 to 12.

In other preferred aspects the connector moiety [CON} is a

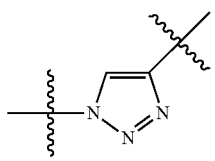 [SMILES: *c1cn(*)nn1]

N group which can be covalently bonded at

with a ABT group, a CBT group or alternatively, a linker group to provide compounds as otherwise described herein.

In still other preferred aspects the linker group is a oligo or polyethyleneglycol moiety of the structure:

Where m is from 1 to 100 or as otherwise described herein, preferably about 8 to 12. Noted there is that polypropylene glycol or polyethylene glycol-co-polypropylenen glycol linkers may be substituted for PEG groups in the present compounds.

Figure 7:
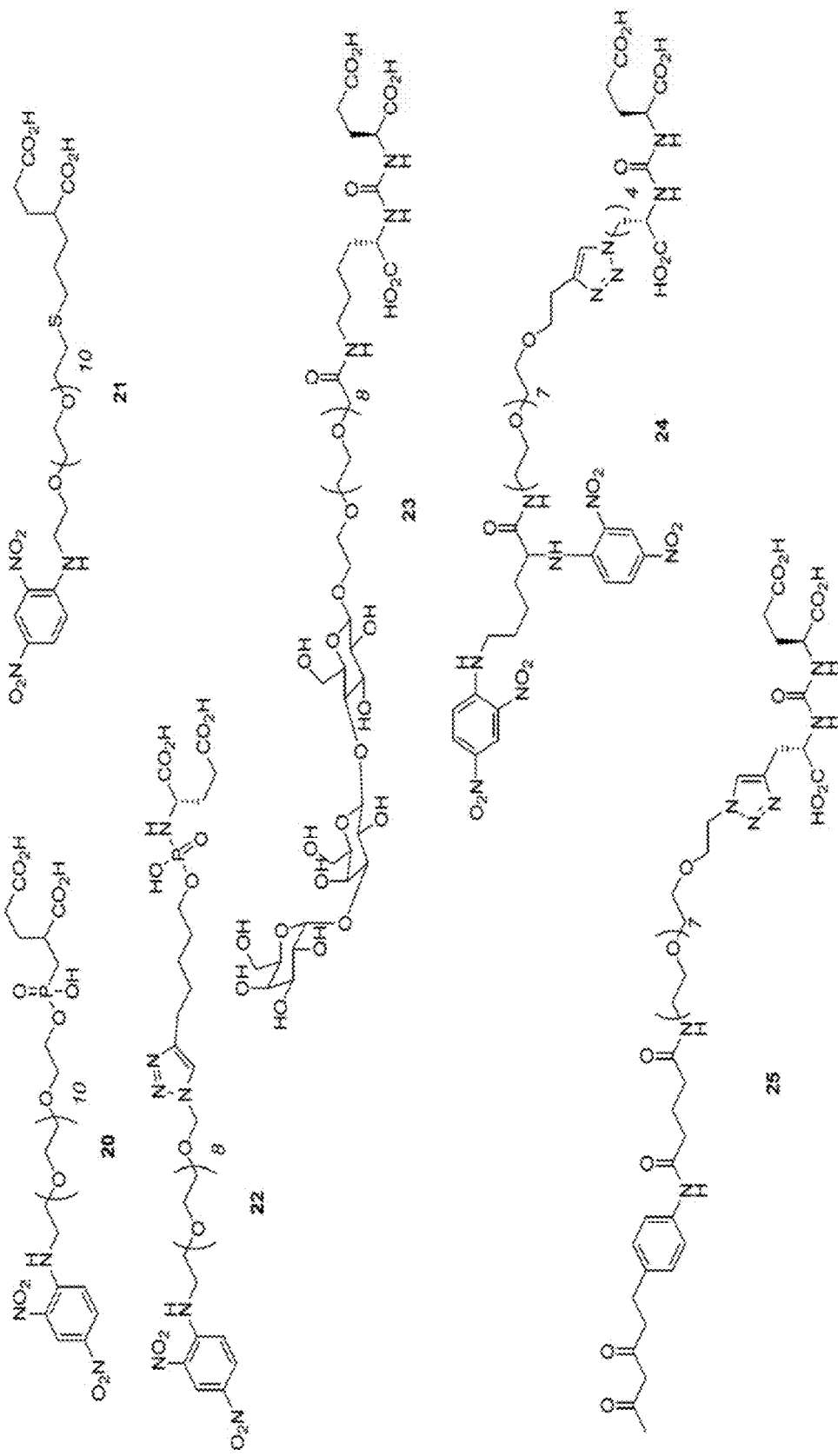
FIG. 7 shows exemplary compounds according to the present invention.

A number of preferred compounds, 20, 21, 22, 23, 24 and 25 are set forth in attached FIG. 7.

In certain preferred aspects, the compound is according to the chemical structure:

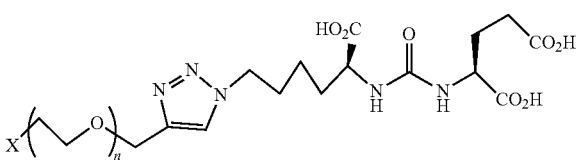

Where n is 0 to 12, O to 12, O to 8, O to 6, 1 to 4; and
X is

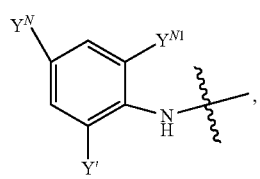

Where $Y^N$, $Y^{N1}$ and Y' is H or $NO_2$; with at least one of $Y^N$, $Y^{N1}$ and Y' being $NO_2$, Or a pharmaceutically acceptable salt, enantiomer, diastereomer, solvate or polymorph thereof.

In the above compounds, X is preferably

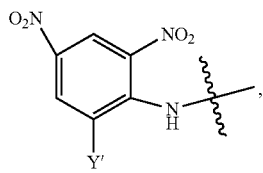

where Y' is H or $NO_2$, preferably H,

Pharmaceutical compositions comprising combinations of an effective amount of at least one chimeric antibody-recruiting compound according to the present invention, and one or more of the compounds otherwise described herein, all in effective amounts, in combination with a pharmaceutically effective amount of a carrier, additive or excipient, represents a further aspect of the present invention.

The compositions of the present invention may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially to treat skin cancers, psoriasis or other diseases which occur in or on the skin. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound in a pharmaceutical composition of the instant invention that may be combined with the carrier materials to produce a single dosage form will vary depending upon the host and disease treated, the particular mode of administration. Preferably, the compositions should be formulated to contain between about 0.05 milligram to about 750 milligrams or more, more preferably about 1 milligram to about 600 milligrams, and even more preferably about 10 milligrams to about 500 milligrams of active ingredient, alone or in combination with at least one additional non-antibody attracting compound which may be used to treat cancer, prostate cancer or metastatic prostate cancer or a secondary effect or condition thereof.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject (e.g. a male human) suffering from cancer can be treated by administering to the patient (subject) an effective amount of a chimeric antibody recruiting compound according to the present invention including pharmaceutically acceptable salts, solvates or polymorphs, thereof optionally in a pharmaceutically acceptable carrier or diluent, either alone, or in combination with other known anticancer or pharmaceutical agents, preferably agents which can assist in treating prostate cancer, including metastatic prostate cancer or ameliorate the secondary effects and conditions associated with prostate cancer. This treatment can also be administered in conjunction with other conventional cancer therapies, such as radiation treatment or surgery.

These compounds can be administered by any appropriate route, for example, orally, parenterally, intravenously, intradermally, subcutaneously, or topically, in liquid, cream, gel, or solid form, or by aerosol form.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from 0.01-3% wt/wt in a suitable carrier.

The compound is conveniently administered in any suitable unit dosage form, including but not limited to one containing less than 1 mg, 1 mg to 3000 mg, preferably 5 to 500 mg of active ingredient per unit dosage form. An oral dosage of about 25-250 mg is often convenient.

The active ingredient is preferably administered to achieve peak plasma concentrations of the active compound of about 0.00001-30 mM, preferably about 0.1-30 μM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its pro-drug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action, such as other anticancer agents, antibiotics, antifungals, antiinflammatories, or antiviral compounds. In certain preferred aspects of the invention, one or more chimeric antibody-recruiting compound according to the present invention is coadministered with another anticancer agent and/or another bioactive agent, as otherwise described herein.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension.

General Chemical Synthesis

The chimeric antibody-recruiting compounds according to the present invention may be synthesized readily using standard chemical connectivity between the linker and cell binding terminus (CBT) and the antibody binding terminus (ABT), along with appropriate protecting groups when necessary. The approach uses standard functional group chemistry in order to link a cell binding moiety to an antibody binding moiety through a linker, which, in preferred aspects, provides an optional connector moiety (between the linker and the ABT or the linker and the CBT depending on functional groups, reactions used, etc.) which forms when the CBT is covalently bonded (connected) to the ABT antibody binding through the linker. Noted here is the fact that the connector moiety per se is not required and the linker, as otherwise described herein, may be covalently bonded directly to a CBT and/or an ABT without the formation of a specific connector moiety. In the present invention, the connector moiety, which is preferably included in chimeric antibody-recruiting compounds according to the present invention, reflects its formation reflective of favorable synthetic chemistries to provide chimeric compounds as otherwise disclosed herein.

As depicted in the general scheme below, a carboxylic acid, such L-A, could be coupled to either an amine or an alcohol, such as C-A, to generate esters or amides through standard carbodiimide conditions (DCC, EDC, DIC along with base and catalytic amine (DMAP, imidazole), by conversion to the acid chloride through oxaly chloride or thionyl chloride etc. followed by addition of amine/alcohol.

Additionally, for example, an amine or an alcohol, such as A-A, can be coupled to an isocyanate or an isothiocyanate, such as C-E, to generate ureas, thioureas, or the corresponding carbonates or thiocarbonates.

In yet another approach, a triazole may be synthesized through a cycloaddition reaction between an azide, such as C-B, and an alkyne, such as L-C. This can be catalyzed by copper, such as copper sulfate along with ascorbic acid, to facilitate a clean reaction.

Still, in a further approach, for example, a heterolinker can be made through treating a nucleophile, such as A-A, with the appropriate leaving group, such as L-E. Some leaving groups could be halogens, such as bromine, or sulfonates, such as triflates or tosylates.

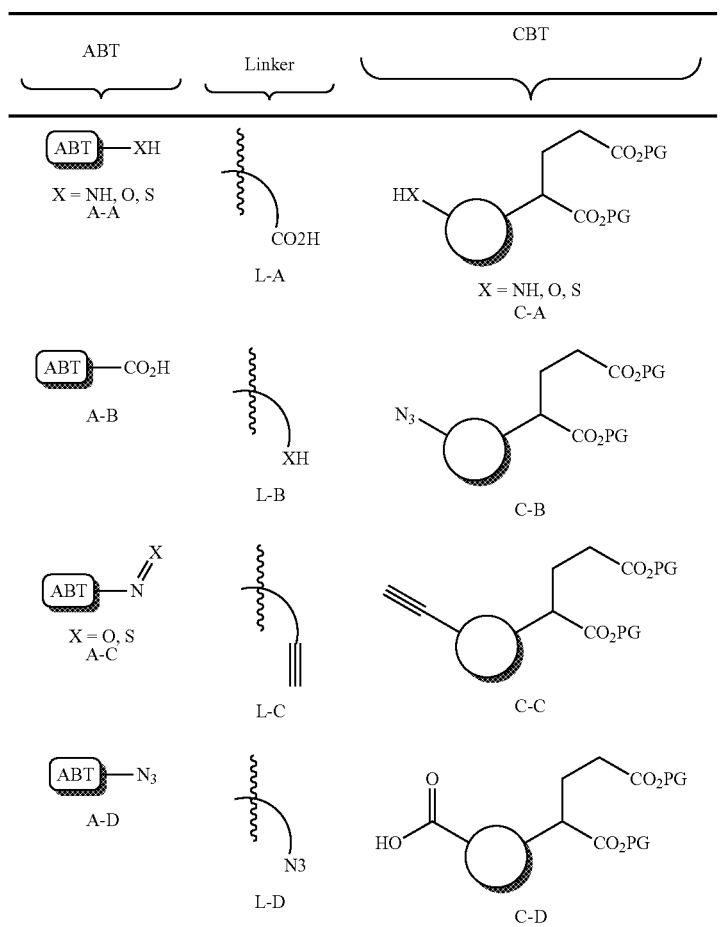

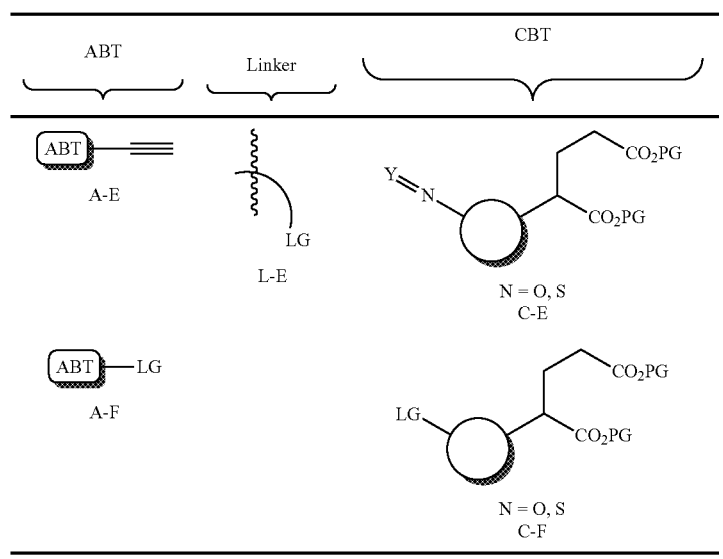

LG = leaving group such as Cl, Br, OTs, ect.
PG = protecting group, such as t-Bu, Bn, etc.

Compounds

Figure 2A:
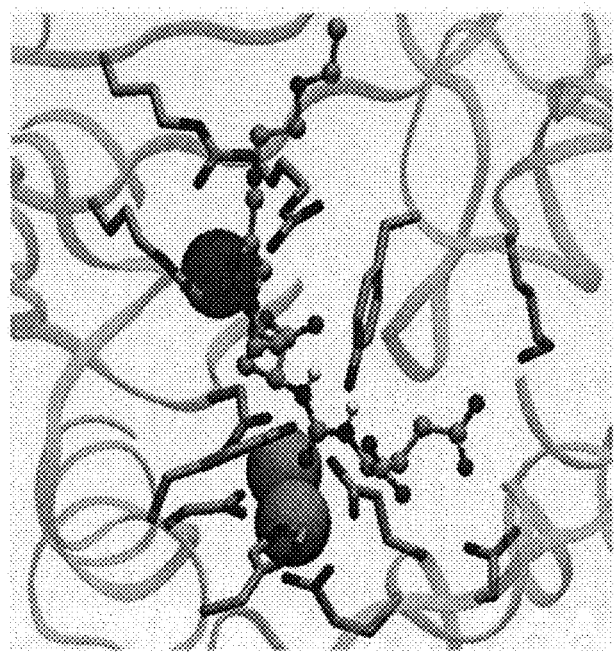
FIG. 2(A) shows computational modeling of cell-binding terminus in the binding pocket of PSMA.
Figure 2B:
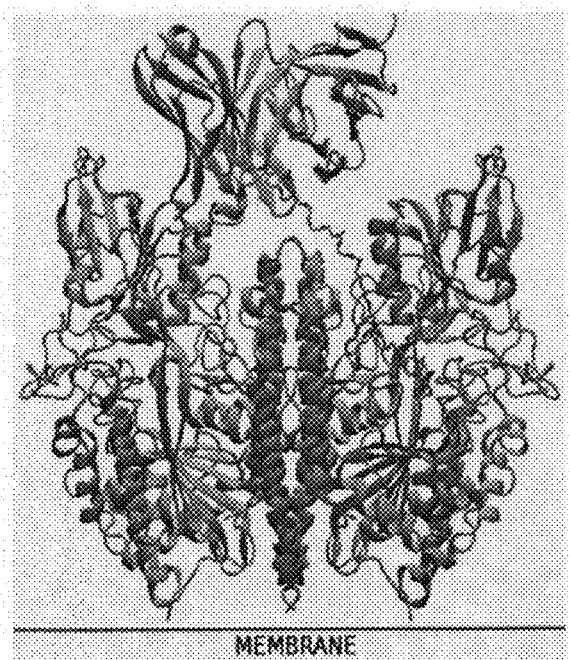
FIG. 2(B) shows a model of PSMA-small molecule-Anti-DNP antibody ternary complex.
Figure 3:
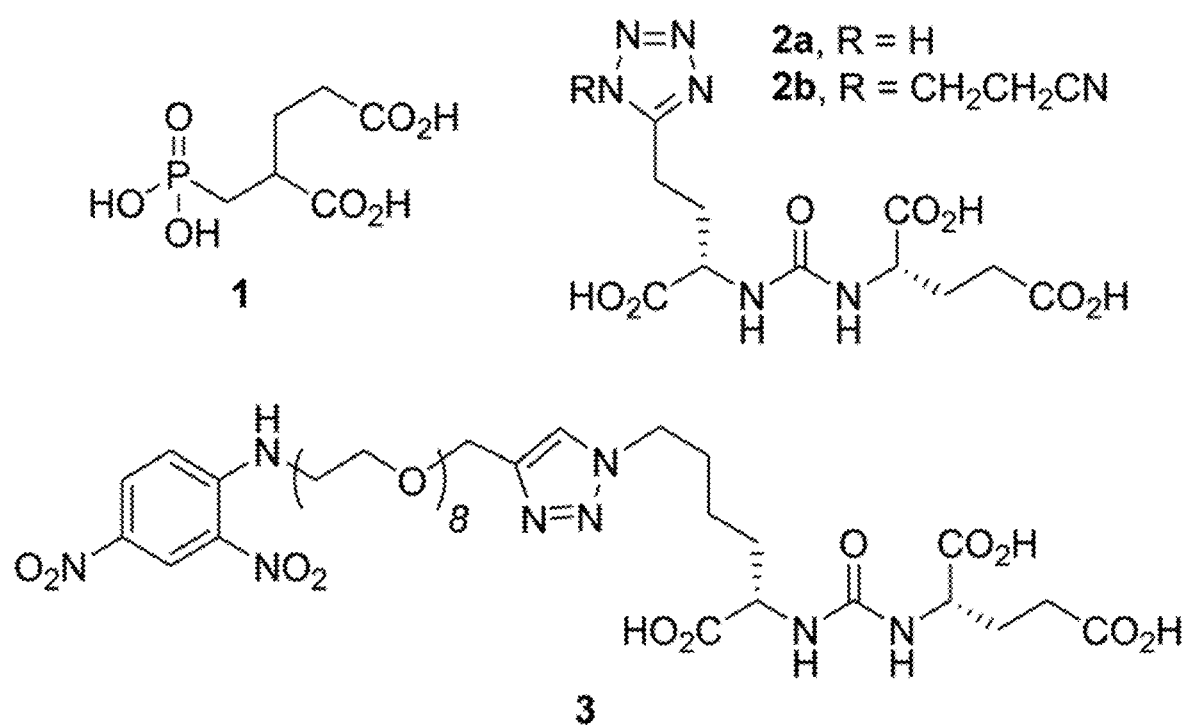
FIG. 3 shows a prostate cancer antibody-recruiting molecule of the present invention, PC-ARM (3).

Several high affinity ligands have been developed to target PSMA selectively. See, Slusher, et al, *Nature Medicine*, 1999, 5, 1396. FIG. 1 depicts the small molecule templated immunotherapy which is generally understood to represent the principal mechanism of chimeric antibody-recruiting compounds according to the present invention. PC-ARM (3, FIG. 3) was inspired by a urea-based, tetrazole-containing ligand with exceptionally high affinity (2, Ki=0.9 nM) {See, Kozikowski, *J. Med. Chem.*, 2004, 47, and refined with molecular modeling to accommodate a solvent-exposed appendage (FIG. 2A). A model of this overall ternary complex (FIG. 2B) suggested that a sizeable tether length would be required (8-12 polyethylene glycol units).

Figure 4:
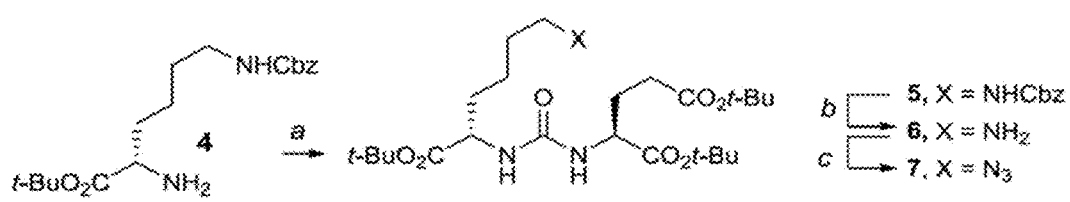
FIG. 4 shows the synthesis of the prostate cancer antibody-recruiting molecule of FIG. 3. The azide-functionalized cell-binding terminus was synthesized in 3 steps by coupling Cbz-protected lysine and t-butyl protected glutamic acid with triphosgene, followed by Cbz deprotection and azide formation (scheme 2). Heterobifunctional PEG 10 was synthesized in a five step process from octaethylene glycol (scheme 2). These intermediates were coupled via microwave assisted, copper-catalyzed Huisgen cyloaddition, and deprotected using microwave assisted TFA deprotection (scheme 3) afforded the prostate cancer antibody-recruiting molecule of the present invention PC-ARM (3).
Figure 4:
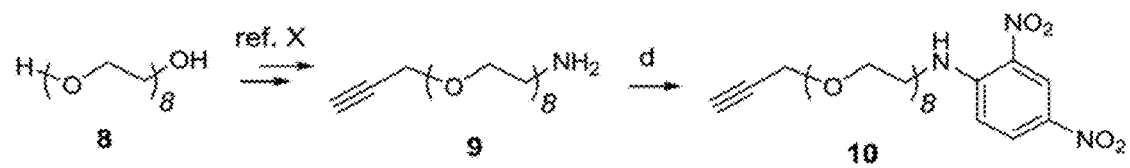
Figure 4:
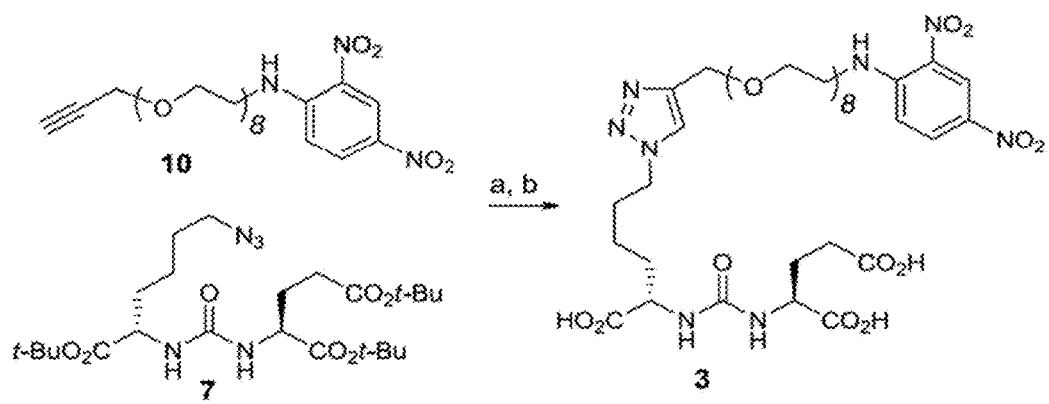

The azide-functionalized cell-binding terminus was synthesized in 3 steps by coupling Cbz-protected lysine and t-butyl protected glutamic acid with triphosgene (See, Kozikowski, et al., *J. Med. Chem.*, 2004, 47, 1729) followed by Cbz deprotection and azide formation (Scheme 2, FIG. 4). Link, et al., *J. Am. Chem. Soc.*, 2004, 126, 10598. Heterobifunctional PEG 10 was synthesized in a five step process from octaethylene glycol (Scheme 2, FIG. 4). Natarajan, et al., *J. Chem. Comm.*, 2007, 7, 695. These intermediates were coupled via microwave assisted, copper-catalyzed Huisgen cyloaddition, (Bouillon, et al., *J. Org. Chem.*, 2006, 71, 4700) and deprotected using microwave assisted TFA deprotection (Scheme 3, FIG. 4) afforded PC-ARM (3). This specific synthesis may be genericized and applied to produce a large number of compounds according to the present invention simply following the experimental section set forth hereinbelow. Inhibition experiments against a human recombinant PSMA (R&D Research) confirmed indirectly that this long-tethered molecule could bind PSMA with high affinity (Ki=0.9±0.3 nM).

Figure 5A:
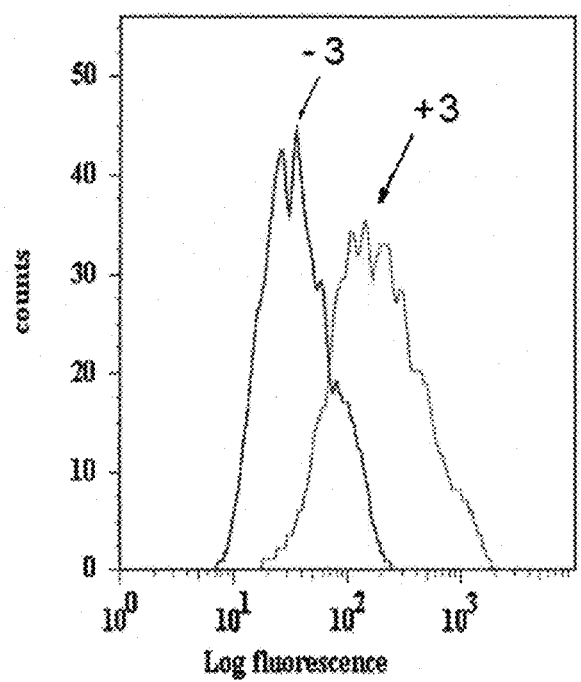
FIG. 5A-B shows in (5A) a representative flow cytometry histogram illustrating small-molecule 3-dependant anti-DNP antibody binding to PSMA-expressing LNCaP cells. LNCaP cells were preincubated with 3 (50 nM), and subsequently incubated with Alexa Fluor 488-conjugated anti-DNP antibodies. (5B) Representative flow cytometry histogram illustrating no small-molecule 3 dependant anti-DNP antibody binding to PSMA-negative DU-145 cells. DU-145 cells were preincubated with 3 (50 nM), and subsequently incubated with Alexa Fluor 488-conjugated anti-DNP antibodies.
Figure 5B:
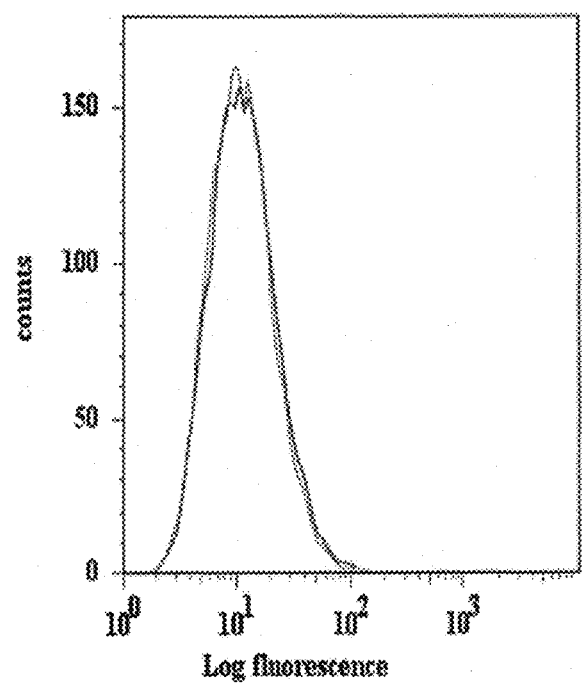

In order to confirm the antibody-recruiting capability of our small-molecule, live-cell recruitment assays were performed with PSMA-expressing LNCaP cells and Alexafluor488 conjugated anti-DNP antibodies. In the presence of anti-DNP antibodies, only a small shift was observed, likely due to non-specific binding. However, when chimeric molecule 3 was added, an increase in fluorescence was observed, indicating the formation of the desired ternary complex formation (FIG. 5A). In fact, this increase in fluorescence could be observed at concentrations well into the picomolar concentration range, suggesting exceptional activity. An observed decrease in fluorescence with the addition of either 2-phosphonomethyl pentanedioic acid (Slusher, et al., *Nature Medicine*, 1999, 5, 1396) or di-DNP lysine confirmed that the recruitment was the result of both the cell-binding and antibody-binding termini. In addition, cells expressing no PSMA showed no significant increase in fluorescence (FIG. 5B).

Figure 6:
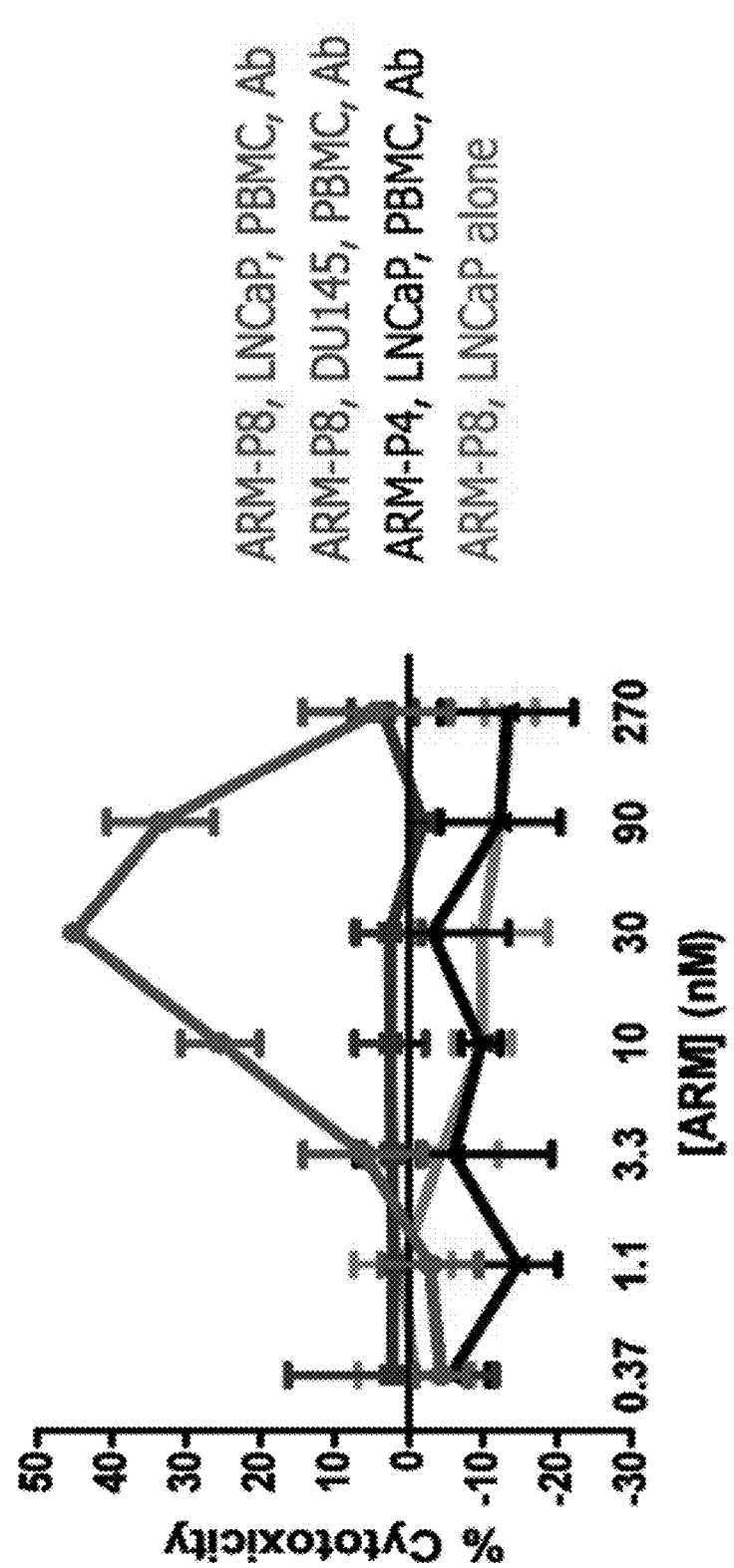
FIG. 6 shows the change in % cell killing induced by PC-ARM (3) (shown in the figure as ARM-P8). In short, LNCaP cells and PBMCs were incubated in the presence of anti-DNP antibody IgG1, IgG3 and a sample of normal human IgG known to have anti-DNP antibodies for 24 hours at 37° C. The change in % cell-killing reflects the increase associated with addition of 50 nM P-ARM8 (3). The data was run in dodecaplets, and is reported as the average±SEM. In addition, each experiment was run in parallel with 50 nM P-ARM8 alone to screen for inherent small-molecule induced cell-killing.

Further, the ability of our molecules to induce cell killing was tested. While small-molecule (3) induced increases in cell-killing were not seen, or were modest, (<20%) using a complement-dependant cytotoxicity assays in the presence of anti-DNP antibodies, significant increases in cell-death was observed in preliminary antibody-dependant cell-mediated cytotoxicity assay (ADCC). In the presence of anti-DNP antibodies and human peripheral blood mononuclear cells, 3 alone does not show cytotoxicity, and ADCC does not occur on PSMA-DU145 cells (FIG. 6). These results are consistent with reports of naked monoclonal antibodies to PSMA being capable inducing ADCC but not CDC responses. Deo, et al., international patent publication WO2003/064606. Current work is underway to confirm these results, and better understand the mode of action, such as the specific effector cells that mediate the killing.

Alternative Compounds

Figure 9:
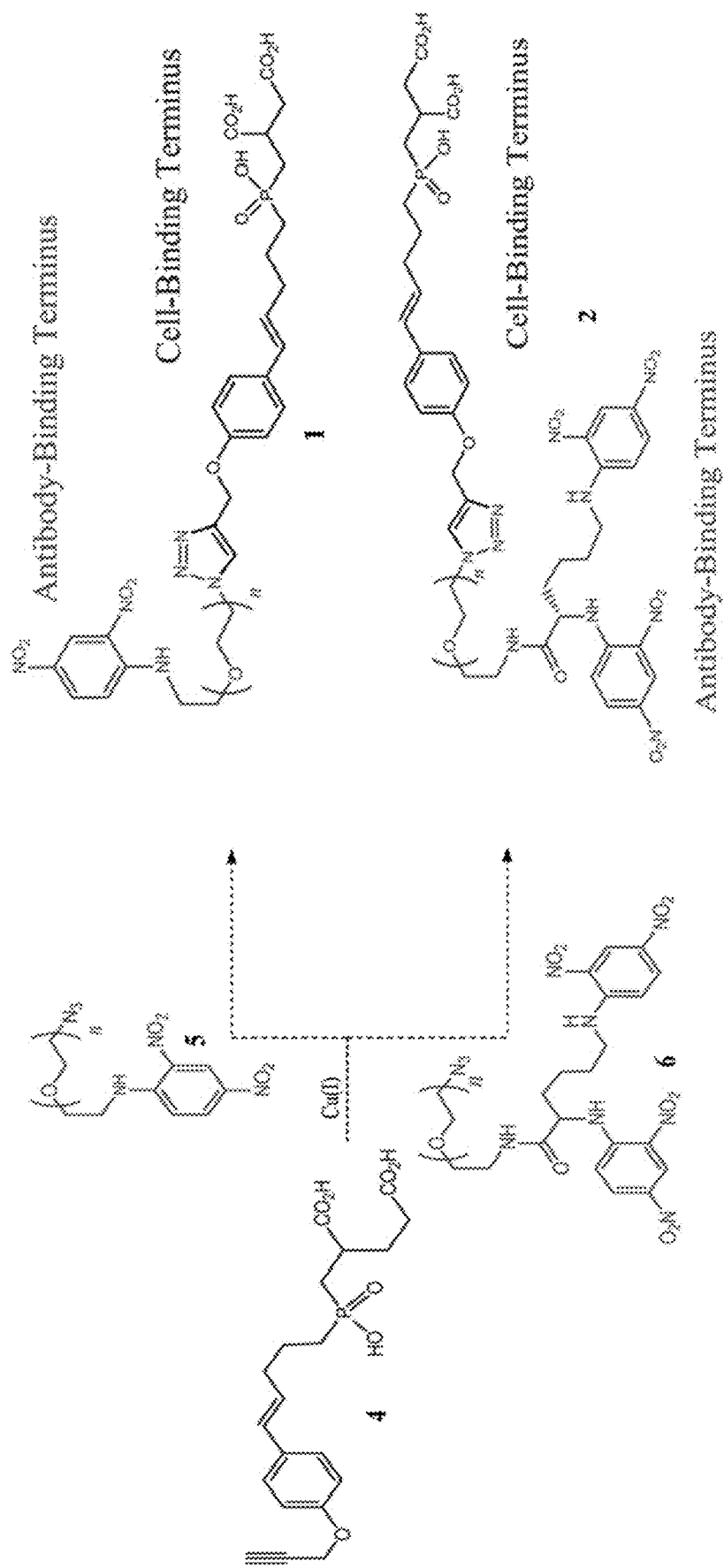
FIG. 9 shows divergent synthetic scheme 1a which is used for target synthesis.

Alternatively, in relying on the above described general approach, molecule (4) (FIG. 9) may be readily synthesized and used as a synthon for the chemical synthesis of dimeric compounds according to the present invention. Compound 4 or similar synthetically manageable molecules that have a propargyl tether that can be used for click chemistry (Scheme 1a, FIG. 9). See, Sharpless and Manetsch, *Expert Opinion on Drug Discovery* 2006, 1, 525-538. Treating this molecule to azides 5 and 6 with variously lengthened polyethylene glycol units allows rapid entry into a group of chimeric recruiting molecules of different tether lengths. Having the flexibility to alter the chain length is important to assist in identifying an optimal CBT-ABT distance.

Figure 10:
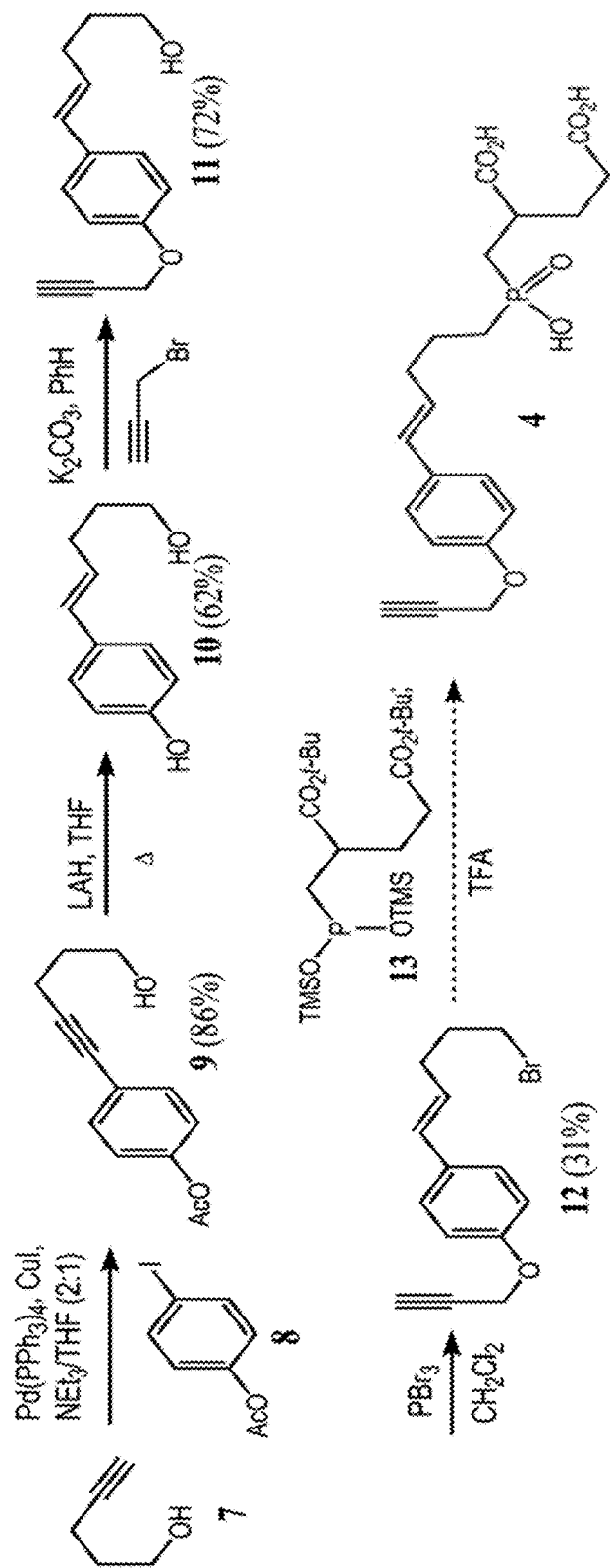
FIG. 10 shows Scheme 2a—synthesis toward propargyl intermediates used in synthesizing compounds according to the invention.

Efforts toward alkyne 4 have provided us with bromide intermediate 12, which will generate our target through an Arbuzov reaction with known phosphate 13 (Scheme 2a, FIG. 10). See, Jackson, et al., *J. Med. Chem.* 2001, 44, 4170-4175. Sonogashira coupling of 7 and 8 provides the carbon framework for the linker, (Liu and Stahl, *J. Am. Chem. Soc.;* 2007; 129; 6328-6335) and LAH reducing conditions generates 10 in the appropriate trans-substituted orientation (Luo, et al., *Chem. Comm.* 2007, 2136-2138) and deprotects the acyl group. This newly deprotected phenol is selectively deprotonated over the homoallylic alcohol with potassium carbonate and trapped with propargyl bromide to generate 11. The remaining alcohol can then be converted to an alkyl bromide through the use of phosphorous tribromide.

Figure 11:
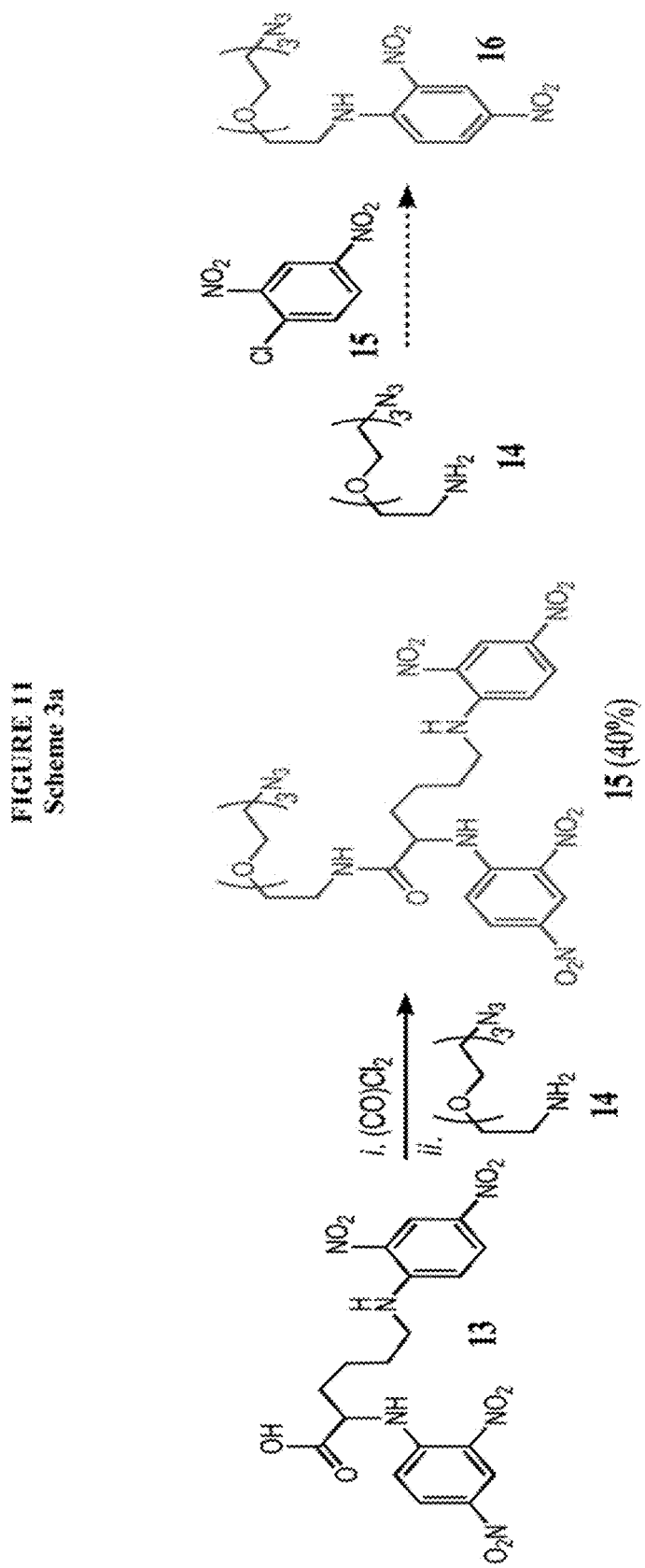
FIG. 11 shows Scheme 3a which is directed to the synthesis of intermediate 15, and proposed access to azide intermediate 16 to be used in click chemistry.

The synthesis of the azide coupling partners is also provided. See Scheme 3, FIG. 11. The focus was on azide 15 because bis-DNP lysine attached to polyethylene glycol linkers has demonstrated significant affinity toward anti-DNP antibodies. See, Baird, et al. *Biochem.* 2003, 42, 12739-12748. This particular azide, which possesses 3 polyethylene glycol units, was synthesized in one-pot from commercially available bis(2,4-dinitrophenyl)-lysine and 1 1-azido-3,6,9-trioxaundecan-1-amine. This was accomplished through a Schotten-Bauman protocol to provide the desired product in an unoptimized yield of 40%. Demko, et al., *J. Org. Chem.* 2001, 66, 7945-7950. Scheme 3a, FIG. 11. Alternatively, mono DNP azide 16 may be readily prepared through nucleophilic aromatic substitution.

Synthesis of Polyvalent Derivatives

Figure 12:
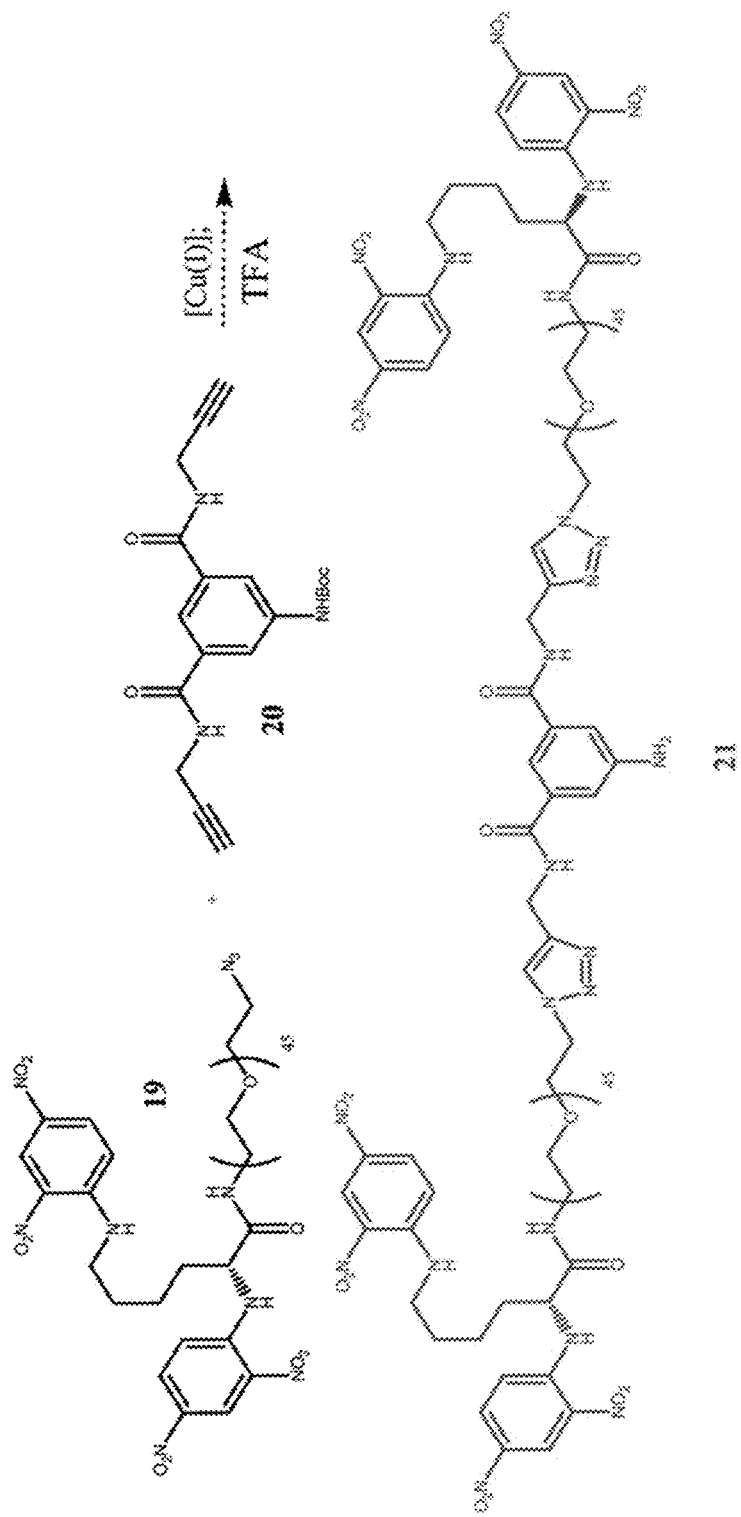
FIG. 12 shows scheme 4a which describes a synthetic approach to bis di-DNP lysine 21.

Polyvalent derivatives can be synthesized in a divergent manner from the previously proposed intermediates. Synthetically complementary bis-alkynyl and tris-azidyl compounds are known, and can be used very effectively in this pursuit. Bis-alkynyl 20 can be converted under click conditions with a longer PEG-derived azido-DNP 19, to generate the desired bis-di DNP analog 21 (Scheme 4a, FIG. 12).

Figure 8:
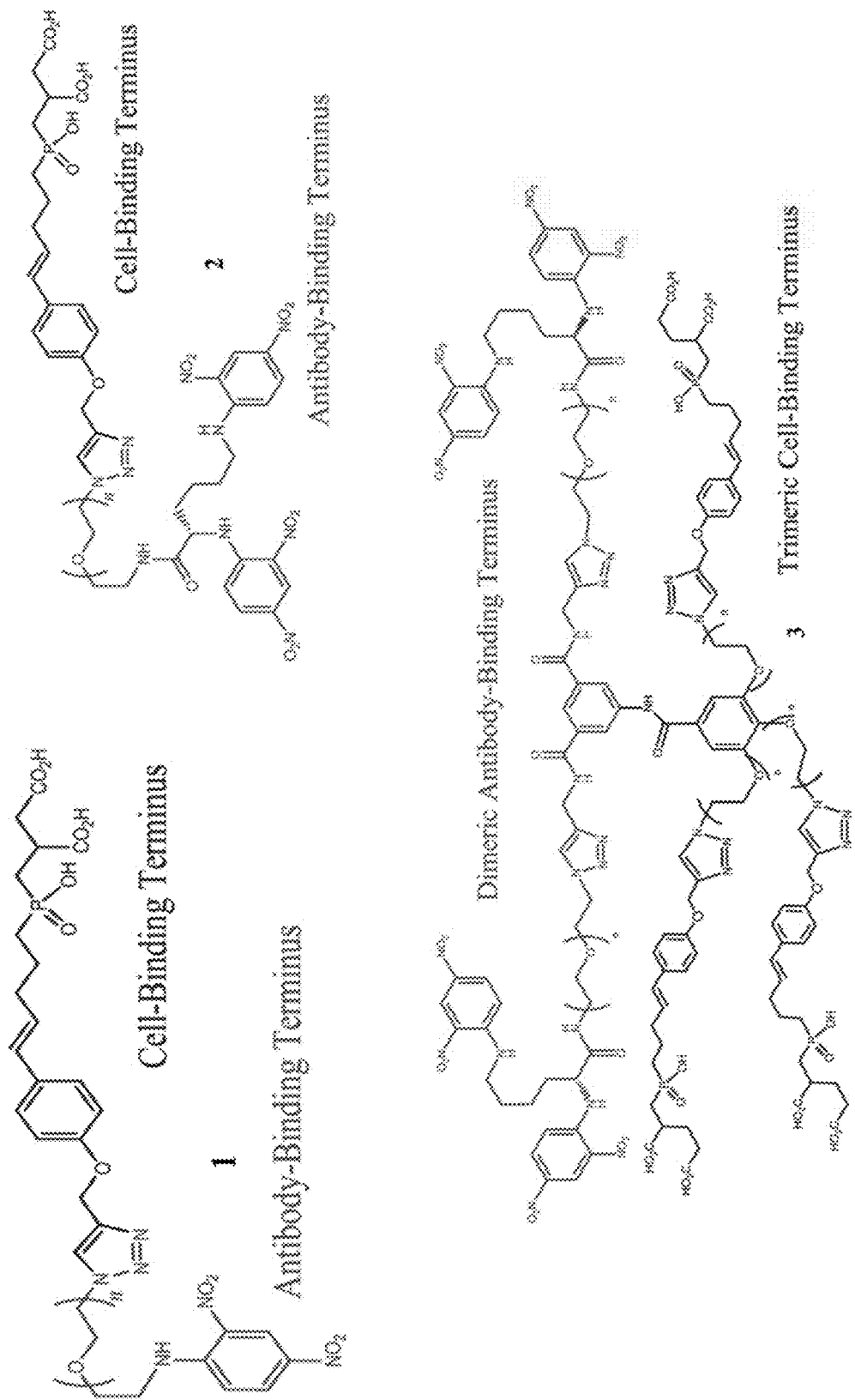
FIG. 8 shows additional exemplary compounds according to the present invention.
Figure 13:
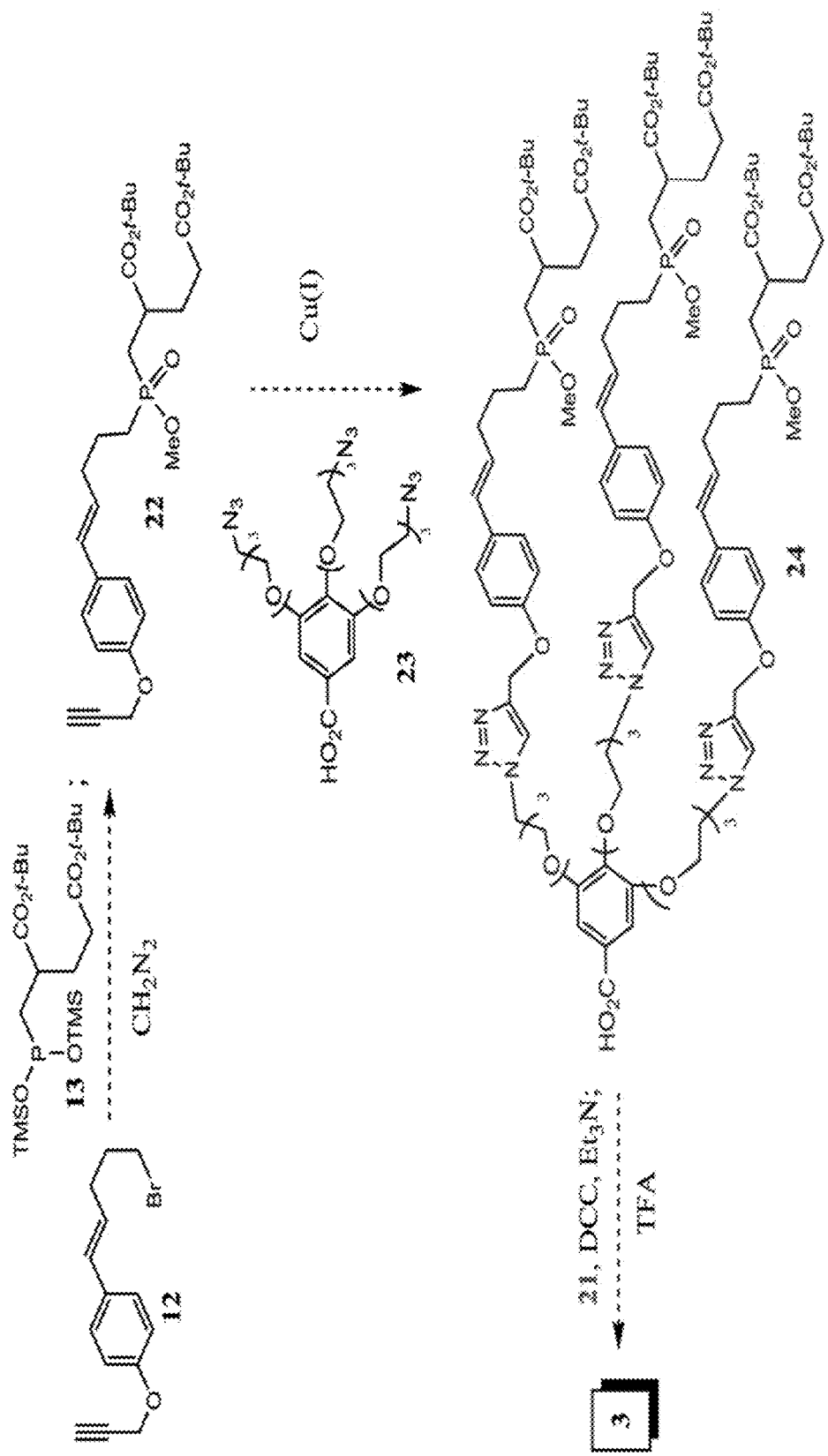
FIG. 13 shows scheme 5a which describes a synthetic approach to the tris-azidylated analog which can be used to condense with the bis-diDNP lysine 21 to produce compound 3 of FIG. 8 or similar compounds.

The tris-azidylated analog can be synthesized in a similar manner from a known triazide 23. See Scheme 5a, FIG. 13. See, Kale, et al., *Biorg. Med. Chem. Lett.* 2007, 17, 2459-2464. This triazide can undergo click chemistry with protected intermediate 22 to provide trimeric 2-PMPA analog 24. With these synthetic pieces (synthons) in hand, the final molecule can be put together by standard peptide coupling followed by TFA deprotection. The final compound is presented in FIG. 8 (compound 3).

The experiments conducted and presented here demonstrate that small-molecule antibody-recruiting molecules which bind selectively to prostate-specific membrane antigen can recruit antibodies to PSMA-expressing cells and induce cell killing. This small-molecule mediated response represents a new treatment for cancer.

The present invention is further described by way of the presentation of the following examples. While these examples are to be taken as exemplary of the present invention, they are not limiting in any way.

Examples

General Information

Unless otherwise stated, all reactions are carried out in flame-dried glassware under a nitrogen atmosphere. All reagents were purchased from commercial suppliers and used without further purification except the following: Triethylamine was distilled over calcium hydride; $CH_2Cl_2$, PhMe, DMF, and THF were purified using a solvent dispensing system; Water was purified using a Milli-Q purification system.

Infrared (IR) spectra bands are characterized as broad (br), strong (s), medium (m) and weak (w). $^1H$ NMR chemical shifts are reported with the solvent residual peak as the internal standard ($CDCl_3$ δ 7.26 ppm or $CD_3OD$ δ 3.31 ppm). Data are reported as follows: chemical shift, integration, multiplicity (s=singlet, d=doublet, t=triplet, q=quartet, br=broad, m=multiplet), and coupling constants (Hz). $^{13}C$ NMR chemical shifts are reported in ppm with the solvent as an internal reference ($CDCl_3$ δ 77.2 ppm Synthesis

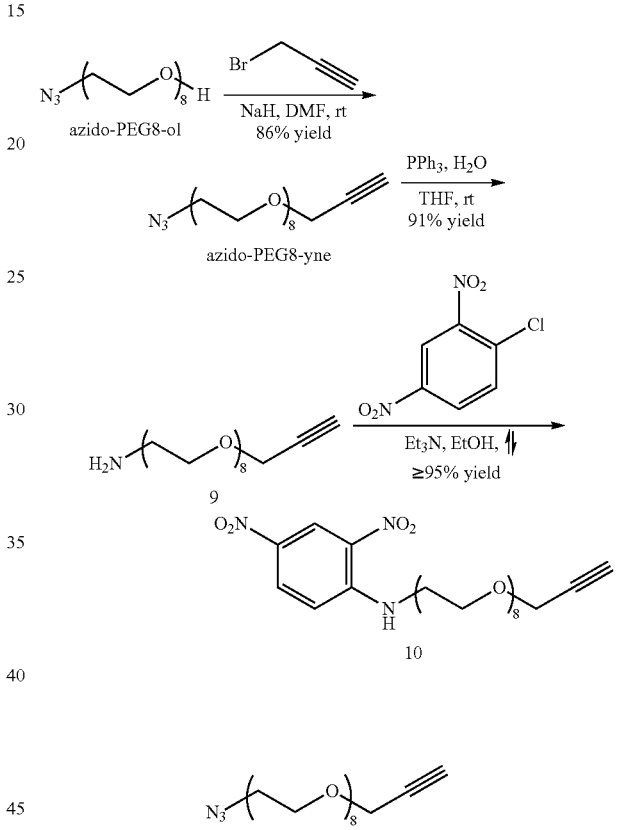

1-azido-3,6,9,12,15,18,21,24-octaoxaheptacos-26-yne (azido-PEG8-yne)

23-Azido-3,6,9,12,15,18,21-heptaoxatricosan-1-ol (azido-PEG8-ol) (1.1 g, 3.17 mmol, 1.0 equiv.) was dissolved in N,N'-dimethylformamide (6 mL), and sodium hydride (152 mg, 6.34 mmol, 2.0 equiv.) was added, followed by propargyl bromide (80% in PhMe, 683 μL, 6.34 mmol, 2.0 equiv.). The reaction ran for 4 h at rt, at which time it was found complete by NMR aliquot. The reaction was taken up in $CH_2Cl_2$ (25 mL) and washed with a saturated aqueous ammonium chloride solution (25 mL). The aqueous solution was back-extracted with dichloromethane (2×10 mL), and combined organics were dried over $MgSO_4$ and concentrated to a brown oil. Chromatography (3 cm×20 cm Silica gel, 3% $MeOH/CH_2Cl_2$) yielded azido-PEG8-yne (960 mg, 78% yield). IR (thin film/NaCl) 2874 (m), 2110 (m), 1160 (s), 1105 (s) cm$^{-1}$; $^1$HNMR (400 MHz, $CDCl_3$) δ 4.20 (d, J=2.4 Hz, 2H), 3.58 (m, 30H), 3.39

(t, J=5.1 Hz, 2H), 2.43 (t, J=2.4 Hz, 1H), 1.82 (s, 1H); $^{13}$CNMR (125 MHz, CDCl$_3$) δ 79.82, 74.72, 70.75, 7022, 68.27, 58.62, 50.84; HRMS (ES+) calc'd for C$_{19}$H$_{35}$N$_3$O$_8$ (M+Na) m/z 456.231637. Found 456.23182.

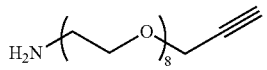

3,6,9,12,15,18,21,24-octaoxaheptacos-26-yn-1-amine (9)

23-Azido-3,6,9,12,15,18,21-heptaoxatricosan-1-ol (azido-PEG8-yne) (960 mg, 2.52 mmol, 1 equiv.), triphenylphosphine (992 mg, 3.78 mmol, 1.5 equiv.), and water (68 μL, 3.78 mmol, 1.5 equiv.) were dissolved in THF (10 mL) and stirred for 12 h. Reaction was concentrated and chromatographed (3 cm×20 cm Silica, CH$_2$Cl$_2$ then ramp to 80:20:1 CH$_2$Cl$_2$:MeOH:Et$_3$N) and concentrated to yield 3,6,9,12,15,18,21,24-octaoxaheptacos-26-yn-1-amine (9) as a clear oil (815 mg, 91% yield). IR (thin film, NaCl) 3105 (br), 2914 (m), 1781 (m), 1638 (m), 1169 (s) cm$^{-1}$. $^{1}$H-NMR (500 MHz, CDCl$_3$) δ 4.17 (d, 2H, J=2.4), 3.66-3.57 (m, 28H), 3.54 (t, 2H, J=5.3 Hz), 2.88 (t, 2H, J=5.0 Hz), 2.41 (t, 1H, J=2.4 Hz), 2.18 (br s, 2H). $^{13}$C NMR (125 MHz, CDCl$_3$) δ 79.52, 74.59, 72.54, 70.41, 70.38, 70.38, 70.35, 70.31, 70.20, 70.06, 68.90, 58.20, 41.44. HRMS (ES+) calc'd for C$_{19}$H$_{37}$NO$_8$ (M+H) m/z 408.259194.

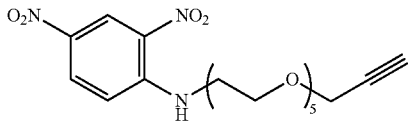

Found 408.25712.

N-(2,4-dinitrophenyl)-3,6,9,12,15,18,21,24-octaoxaheptacos-26-yn-1-amine (10)

3,6,9,12-tetraoxapentadec-14-yn-1-amine (815 mg, 2.27 mmol, 1 equiv.) was dissolved in EtOH (10 mL), and triethylamine (666 μL, 0.726 mmol, 1.5 equiv.) and 1-chloro-2,4-dinitrobenzene (505 mg, 2.5 mmol, 1.5 equiv.) were added. The reaction flask was fitted with a reflux condenser and the reaction was heated to reflux for 48 h, cooled, and concentrated to a yellow oil. The crude mixture was purified by flash chromatography (3 cm×20 cm Silica, 3% MeOH:CH$_2$C$_2$) to yield N-(2,4-dinitrophenyl)-3,6,9,12,15,18,21,24-octaoxaheptacos-26-yn-1-amine (10) as a yellow solid (1.15 g, >95% yield). IR (thin film/NaCl) 3363 (w), 2871 (s), 1621 (s), 1337 (m), 1103 (s) cm$^{-1}$; $^{1}$H-NMR (500 MHz, CDCl$_3$) δ 9.08 (d, 1H, J=2.6 Hz), 8.77 (bs, 1H), 8.21 (dd, 1H, J=2.6, J=9.5 Hz), 6.94 (d, 1H, J=9.5 Hz), 4.16 (6, 2H, J=2.4 Hz), 3.78 (t, 2H, J=5.0 Hz), 3.64 (m, 32H), 3.58 (q, 2H), 2.41 (t, 1H, 2.38 Hz); $^{13}$C-NMR (125 MHz, CDCl$_3$) δ 148.5, 136.1, 130.5, 130.29, 124.3, 114.3, 79.8, 74.6, 70.7, 70.6, 70.5, 69.2, 68.7, 58.5, 43.3; HRMS (EI) calc'd for C$_{25}$H$_{39}$N$_3$O$_{12}$ (M+H) m/z 574.260650. Found 574.26106.

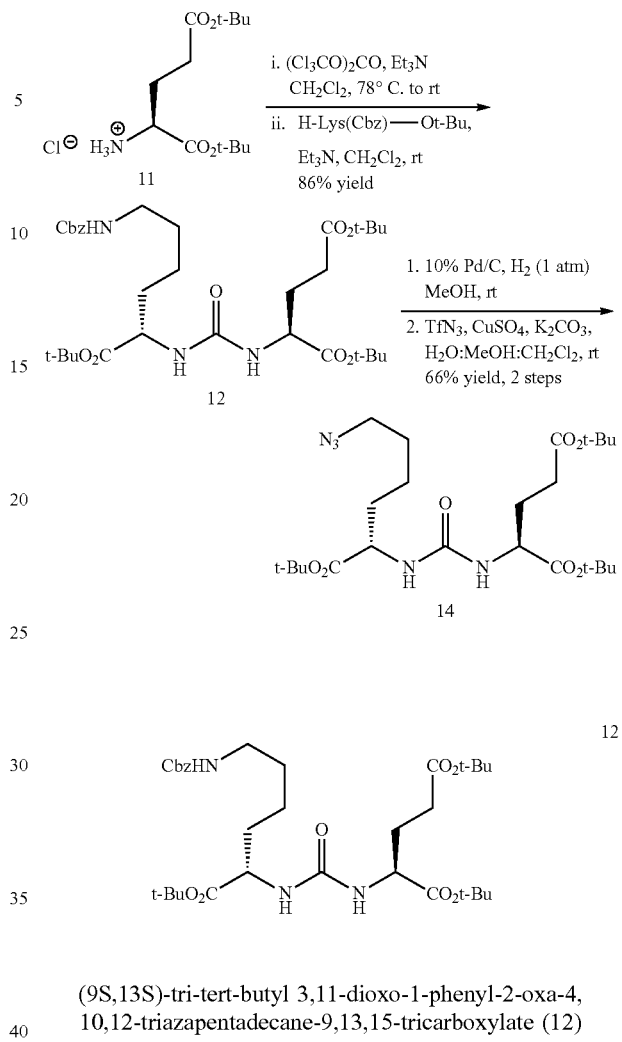

(9S,13S)-tri-tert-butyl 3,11-dioxo-1-phenyl-2-oxa-4,10,12-triazapentadecane-9,13,15-tricarboxylate (12)

11 (1.0 g, 3.38 mmol, 1.0 equiv.) and triethylamine (30 mL) and cooled to −78° C. Triphosgene (341 mg, 1.15 mmol, 0.34 equiv.) in dichloromethane (10 mL) was added dropwise to the reaction mixture. Upon complete addition, the reaction was allowed to warm to room temperature and stirred for 30 minutes. 12 (757 mg, 2.03 mmol, 0.6 equiv) was added, followed by the addition of triethylamine (283 μL, 2.03 mmol, 0.6 equiv.). The reaction was allowed to stir at room temperature overnight for 16 hours. The reaction was then diluted with dichloromethane (50 mL), and washed with water (100 mL×2). The crude mixture was dried over Na$_2$SO$_4$ and concentrated under reduced pressure. Column chromatography (Silica 1.5:1 hexane:ethyl acetate) yielded 4 (1.09 g, 86%) as a colorless oil with the following spectral characteristics: IR (thin film/KBr) 3342, 2976, 1731, 1650, 1552, 1454, 1368, 1255, and 1153 cm$^{-1}$; $^{1}$H NMR (500 MHz, CDCl$_3$) δ 7.35 (d, J=3.75 Hz, 4H), 7.33-7.30 (m, 1H), 5.10 (d, J=4.55 Hz, 2H), 5.06-5.01 (m, 2H), 4.99 (s, 1H), 4.34-4.31 (m, 2H), 3.20-3.18 (m, 2H), 2.36-2.23 (m, 2H), 2.10-2.03 (m, 1H), 1.88-1.75 (m, 2H), 1.65-1.57 (m, 1H), 1.57-1.45 (m, 2H), 1.453 (s, 9H), 1.446 (s, 9H), 1.43 (s, 9H), 1.40-1.30 (m, 2H); $^{13}$C NMR (125 MHz, CDCl$_3$) δ 172.6, 172.5, 172.2, 136.8, 128.6, 128.5, 128.2, 82.2, 82.0, 80.7, 66.7, 53.4, 53.2, 40.7, 32.8, 31.7, 29.4, 28.5, 28.2, 28.1, 22.3; HRMS (EI+) m/z 622.3695 [calc'd for C$_{32}$H$_{51}$N$_3$O$_9$ (M+H)+ 622.3698].

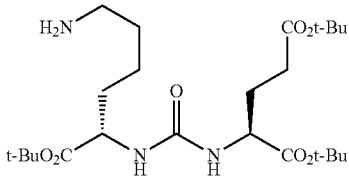

(S)-di-tert-butyl 2-(3-((S)-6-amino-1-tert-butoxy-1-oxohexan-2-yl)ureido)pentanedioate (12)

X (2.35 g, 3.78 mmol, 1.0 equiv.) was dissolved in methanol (37.8 ml) and was added dropwise to a vigorously stirred reaction flask containing dry 10% Pd/C (475 mg). $H_2$ was bubbled through the solution for 1-2 m, and then ran for 13 h under a balloon of $H_2$. The reaction was deemed complete by TLC (Rf=0.48 in 10% $MeOH/CH_2Cl_2$), plugged through celite, and concentrated to give a viscous oil, which was carried on without further purification.

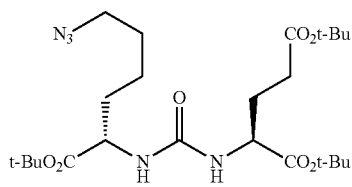

(S)-di-tert-butyl 2-(3-((S)-6-azido-1-tert-butoxy-1-oxohexan-2-yl)ureido)pentanedioate (14)

Sodium azide (2.629 g, 40.75 mmol, 10.0 equiv.) was dissolved in water (7.63 mL), and dichloromethane (12.91 mL) was added. The reaction mixture was cooled to 0° C. and triflic anhydride (1.36 mL, 8.09 mmol, 2.0 equiv.) was added. The solution was stirred for 3 h at rt, and the organic layer was separated from the aqueous layer. The aqueous layer was extracted with dichloromethane (3×4 mL). The organic layers were combined and washed with aqueous $Na_2CO_{3(aq)}$ to give 25 ml of 0.391 M $TfN_3$. Amine 13 (1.97 g, 4.04 mmol, 1.0 equiv.) was dissolved in water (14.37 mL) and methanol (28.74). To this solution were added $CuSO_4 \cdot 5H_2O$ (10.1 mg, 0.04 mmol, 0.01 equiv.) and $K_2CO_3$ (837.5 mg, 6.06 mmol, 1.5 equiv.). The $TfN_3$ solution (25 ml, 8.09 mmol, 2 equiv.) was added rapidly to the stirring solution of 13, and the reaction stirred for 19 h at rt. The organic layer was separated from the aqueous layer, and the water/methanol layer was extracted once with dichloromethane. The combined organic layers were dried over MgSO4, concentrated under reduced pressure, and purified by column chromatography to yield 14 as a white solid (1.440 g, 71%). Rf=0.68 in 10% $MeOH:CH_2Cl_2$. IR (Thin film/NaCl) 3335, 2980, 2933, 2868, 2097, 1733, 1635, 1560, 1368, 1257, and 1155 cm$^{-1}$; $^1$HNMR (500 MHz, $CDCl_3$) δ 5.01 (d, J=8.25 Hz, 2H), 4.34 (m, 2H), 3.26 (t, J=7.4 Hz, 2H), 2.35-2.25 (m, 2H), 2.09-2.05 (m, 1H), 1.87-1.76 (m, 2H), 1.66-1.55 (m, 3H), 1.46 (s, 18H), 1.43 (s, 9H), 1.45-1.35 (m, 2H) ppm; $^{13}$CNMR (125 MHz, $CDCl_3$) δ 172.6, 172.4, 172.2, 156.8, 82.3, 82.1, 80.7, 53.4, 53.2, 51.3, 33.0, 31.7, 28.6, 28.5, 28.2, 28.1, 22.4 ppm; HRMS (EI+) m/z 514.3225 [calc'd for $C_{24}H_{43}N_5O_7$ (M+H)+514.3235].

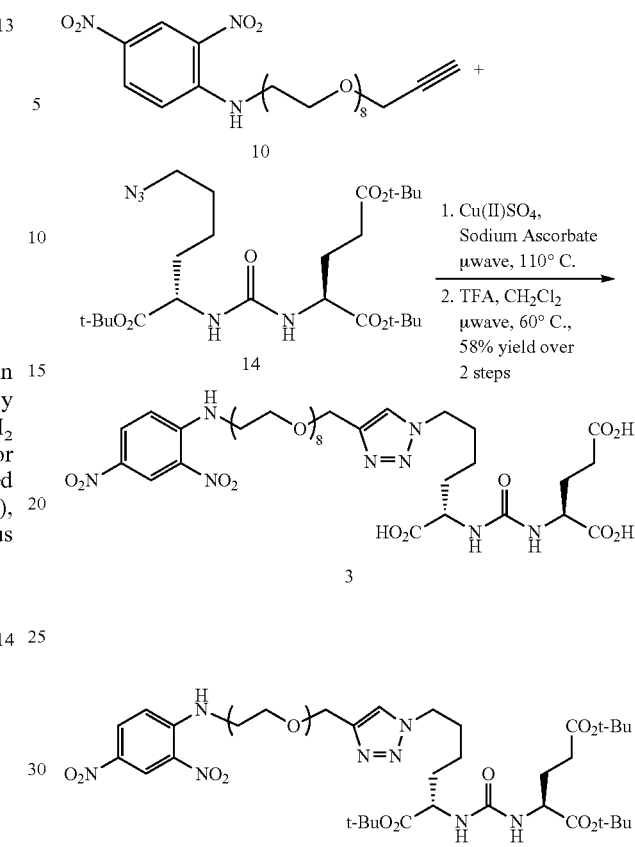

(S)-di-tert-butyl 2-(3-((S)-1-tert-butoxy-6-(4-(13-(2,4-dinitrophenylamino)-2,5,8,11-tetraoxatridecyl)-1H-1,2,3-triazol-1-yl)-1-oxohexan-2-yl)ureido)pentanedioate (3)

To a mixture of 10 (76 mg, 0.145 mmol, 1.0 equiv) and 14 (74.4 mg, 0.145 mmol, 1.0 μwave reaction tube was added sodium ascorbate (7 mg, 0.036 mmol, 0.25 equiv.) and aqueous solution of 0.1 M copper (II) sulfate (0.0725 ml, 0.00725 mmol, 0.05 equiv.). The tube was capped, and subjected to microwave radiation for 10 minutes at 110° C. The reaction was then concentrated and redissolved in trifluoroacetic acid (2 mL) and dichloromethane (1 mL) in a 5 ml microwave reaction tube. The tube was capped and subjected to microwave radiation for 2 m at 70° C. The resulting reaction mixture was concentrated under reduced pressure, chromatographed using HPLC, and concentrated to yield 3 (87 mg, 58% yield) as a yellow oil. IR (thin film/NaCl) 3359 (w), 2925 (s), 1737 (s), 1622 (m), 1170 (s) cm$^{-1}$; $^1$HNMR (100 MHz, MeOD) δ 9.07 (d, J=2.7 Hz, 1H), 8.33 (dd, J=2.7, 9.6 Hz, 1H), 8.03 (s, 1H), 7.27 (d, J=9.6 Hz, 1H), 4.66 (s, 2H), 4.45 (t, J=7 Hz, 2H), 4.35-4.28 (m, 2H), 3.83 (t, J=7 Hz, 2H), 3.73-3.61 (m, 32H), 2.44-2.36 (m, 2H), 2.17-2.08 (m, 1H), 1.99-1.82 (m, 4H), 1.71-1.64 (m, 1H), 1.46-1.38 (m, 2H); $^{13}$CNMR (125 MHz, MeOD) δ 176.4, 176.1, 175.7, 160.0, 149.9, 145.9, 137.0, 131.5, 131.0, 125.2, 124.7, 116.1, 71.6, 71.5, 71.5, 70.9, 69.9, 64.8, 53.7, 53.5, 51.2, 44.1, 32.8, 31.1, 30.6, 28.8, 23.4 ppm; HRMS (ES+) calc'd for $C_{37}H_{58}N_8O_{19}$ (M+H) m/z 919.389098. Found 919.38801.

NAALADase Inhibition Experiments

A 10 mM stock solution of N-acetyl-aspartyl-glutamate (NAAG) in 40 mM NaOH was diluted to 40 μM in Tris buffer (0.1M Tris-HCl, pH=7.5), and was added to 384 well plate (25 μl per well). For Km measurements and controls, 2× dilution (40 μM-312 nM) series of NAAG were made and added to separate wells. For $IC_{50}$ measurements, solutions of recruiting molecule 3 in water (2 μL per well, dilution series) were added to wells. For all other wells, 2 μL of water was added. To initiate reactions, rhPSMA (R&D research) diluted in Tris buffer (20 pg/mL), was added to each well (25 μl per well). For negative controls, Tris buffer was added (25 μl per well). The plate was covered and incubated for 15 minutes, at which time the protein was deactivated by heating the plate to 95° C. for 3 minutes. After plate was allowed to cool, glutamic acid release was visualized using an Amplex®-Red glutamic acid/glutamate oxidase assay kit (Invitrogen). Km and $IC_{50}$ values were calculated using graphpad prism software, and Ki was calculated from these values using the Cheng-Prusoff Equation. This process was run in triplicate, and is reported in the manuscript as the average of three runs±standard deviation.

Flow Cytometry Recruiting Experiments
Antibody Recruitment Flow Cytometry:

LNCaP and DU145 cells were detached, counted, washed, and resuspended with flow cytometry buffer (25 mM Tris-HCl, 150 mM NaCl, 1.5% BSA, 5 mM Glucose, 1.5 mM $MgCl_2$, pH 7.2) to a density of $2\times10^5$ cells $mL^{-1}$ of buffer, and 1 mL was added to each epindorf tube per experiment. Solutions of 3 in water (2 μL, variable concentration per experiment) in flow cytometry buffer were added to the cells, and the cells were incubated at 4° C. for 60 minutes. For cell-binding termini competition experiments, solutions of PMPA in water (2 μL, variable concentrations) were added prior to incubation. Following incubation, the cells were washed three times with flow cytometry buffer. 20 μL of 1 mg $ml^{-1}$ human IgG in mouse serum were added to each tube and the tubes were incubated for 5 minutes at room temperature to allow blocking of Fc receptors. 200 μL of flow cytometry buffer were added, and to that was added 2 μL of 2 mg $ml^{-1}$ AlexaFluor488 conjugated rabbit anti-dinitrophenyl IgG-fraction KLH. For antibody-binding terminus competition experiments, a solution of di-DNP Lysine (2 μL of 5 mM solution in water) was added prior to incubation. The tubes were incubated at 4° C. for 60 minutes and taken up with 850 μL of flow cytometry buffer. The cells were spun down and washed with flow cytometry buffer (2×1 mL). The cells were taken up with 1 mL of Tris buffered saline (25 mM TrisHCl, 150 mM NaCl, pH 7.2) and 2 μL of 500 μg $mL^{-1}$ of propidium iodide was added, and samples were analyzed immediately on FACSCalibur instrument (Becton Dickinson). The data was analyzed using FlowJo (Tree Star Inc.), gating for live cells on FL-3. An experiment omitting 3 was done as a control. The experiment was repeated in triplicate to ensure reproducibility.

Further Examples

Figure 14:
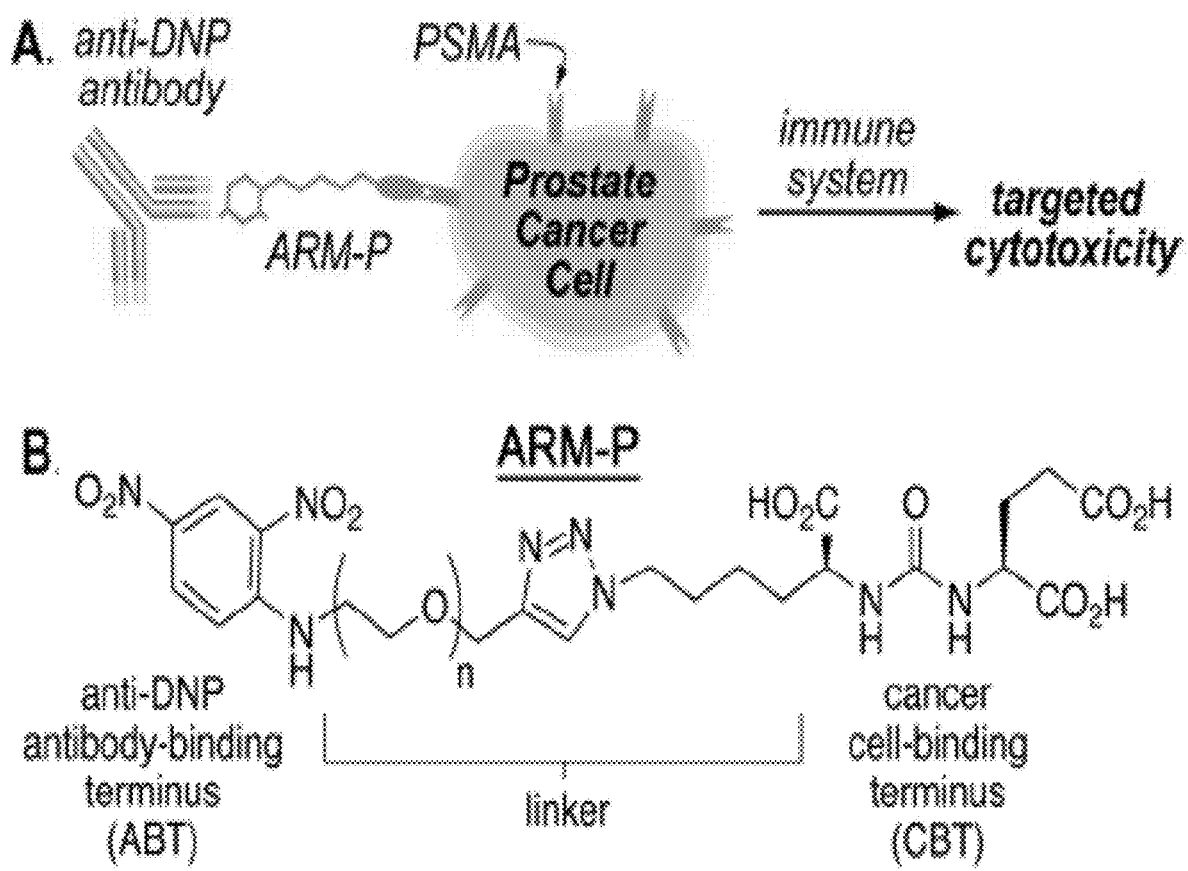
FIG. 14 shows the structure and function of ARM-Ps (antibody-recruiting molecules targeting prostate cancer). (A) ARM-Ps recruit anti-DNP antibodies to PSMA-expressing prostate cancer cells, and thereby bring about immune-mediated cytotoxicity. (B) ARM-Ps are bifunctional and consist of an antibody-binding terminus (ABT), a linker region, and a cell-binding terminus (CBT).

The following experiments relate to a number of additional compounds, i.e., antibody-recruiting molecules targeting prostate cancer (ARM-Ps) which were synthesized and tested for binding affinity and/or inhibition of PMSA. ARM-Ps belong to a class of glutamate urea compounds capable of inhibiting PSMA with high potency. See FIG. 14.

During the course of developing ARM-Ps, the inventors observed that bifunctional DNP-containing conjugates were strikingly more potent than the parent glutamate urea compounds from which they were derived. Furthermore, we also noted that potency increases were correlated to the length of the linker regions connecting the two poles of the molecule. Here we provide a molecular basis for these findings, which involves the disclosure of a previously unreported arene-binding site on PSMA. These conclusions are supported by extensive biochemical, crystallographic, and computational studies.

Synthesis:

All starting materials and reagents were purchased from commercially available sources and used without further purification. $^1$H NMR shifts are measured using the solvent residual peak as the internal standard ($CDCl_3$ 7.26, MeOD 3.31), and reported as follows: chemical shift, multiplicity (s=singlet, bs=broad singlet, d=doublet, t=triplet, dd=doublet of doublet, q=quartet, m=multiplet), coupling constant (Hz), integration. $^{13}$C NMR shifts are measured using the solvent residual peak as the internal standard ($CDCl_3$ 77.20 or MeOD 49.00 or DMSO-$d_6$ 39.01), and reported as chemical shifts. Infrared (IR) spectral bands are characterized as broad (br), strong (s), medium (m), and weak (w).

Chemical Synthesis

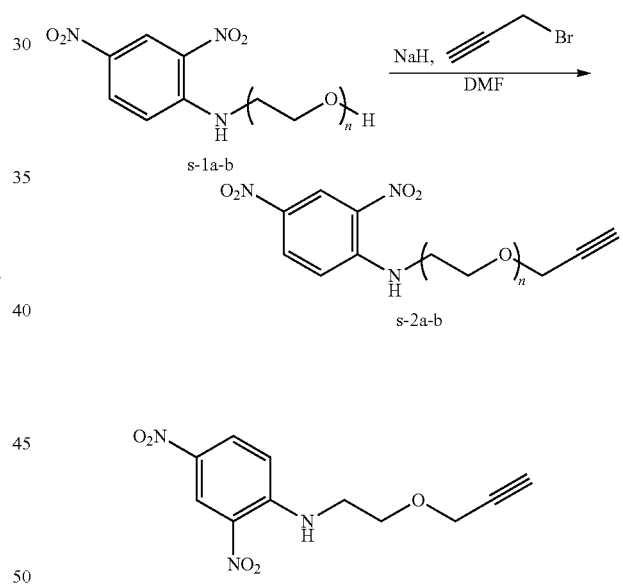

Scheme S-1. General synthesis of DNP—PEG-alkynes from the corresponding DNP—PEG—OH. (a, $n = 1$; b, $n = 2$).

2,4-dinitro-N-(2-(prop-2-ynyloxy)ethyl)aniline
(s-2a)

2-(2,4-dinitrophenylamino)ethanol (s-1a) (410 mg, 1.80 mmol, 1.0 equiv.) was dissolved in 3 mL of DMF and slowly added to a slurry of NaH (86.4 mg, 3.6 mmol, 2 equiv.) in 5 mL of DMF in a flame dried flask pre-cooled to 0° C. To the resulting slurry, 80% propargyl bromide (0.240 mL, 2.16 mmol, 1.2 equiv.) in toluene, cooled to 0° C., was added slowly. The ice bath was removed and the reaction was allowed to stir at room temperature for an additional 15 hours. The reaction was then re-cooled to 0° C., quenched with saturated $NH_4Cl$, and extracted with diethyl ether (3×150 mL). The organic layers were combined, dried, concentrated under reduced pressure, and chromatographed (silica gel, 1×25 cm, 0% CH₃OH in CHCl₃, then 2.5% CH₃OH in CHCl₃) to yield 2,4-dinitro-N-(2-(prop-2-ynyloxy)ethyl)aniline (s-2a) as a dark yellow solid (310 mg, 64.8%). IR (thin film) 3356 (m), 3285 (m), 3105 (w), 2871 (w), 2117 (w), 1616 (s), 1584 (s), 1521 (s), 1499 (m), 1423 (m), 1274 (s), 1089 (s), 920 (m); $^1$H NMR (400 MHz, CDCl₃) δ 9.16 (d, J=2.6 Hz, 1H), 8.76 (bs, 1H), 8.28 (dd, J=9.5, 2.7 Hz, 1H), 6.96 (d, J=9.5 Hz, 1H), 4.25 (d, J=2.4 Hz, 2H), 3.91-3.84 (m, 2H), 3.65 (d, J=5.3 Hz, 1H), 2.50 (t, J=2.4 Hz, 1H). $^{13}$C NMR (125 MHz, CDCl₃) δ 149.5, 136.3, 130.7, 130.4, 124.4, 114.1, 78.9, 75.5, 67.3, 58.7, 43.3. HRMS (ES+) calc'd for $C_{11}H_{11}N_3O_5$ (M+H) m/z 266.0732 Found 266.0771.

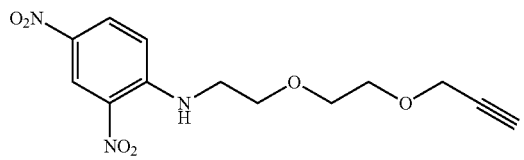 [SMILES: C#CCOCCOCCNc1ccc([N+](=O)[O-])cc1[N+](=O)[O-]]

2,4-dinitro-N-(2-(2-(prop-2-ynyloxy)ethoxy)ethyl) aniline (s-2b)

2-(2-(2,4-dinitrophenylamino)ethoxy)ethanol (s-1b) (100 mg, 0.369 mmol, 1.0 equiv.) was dissolved in 0.81 mL of DMF and slowly added to a slurry of NaH (17.71 mg, 0.738 mmol, 2.0 equiv.) in 0.81 mL of DMF in a flame dried flask pre-cooled to 0° C. An 80% solution of propargyl bromide in toluene (0.049 □L, 0.443 mmol, 1.2 equiv.) was added slowly. The ice bath was then removed and the reaction was allowed to stir at room temperature for an additional 2 hours. The reaction was then re-cooled to 0° C., quenched with saturated NH₄Cl, and then extracted with diethyl ether (3×50 mL). The organic layers were combined, dried with Na₂SO₄, concentrated under reduced pressure, and chromatographed (silica gel, 3×25 cm, 0% EtOAc in hexanes, then 10% EtOAc in hexanes, then 20% EtOAc in hexanes, then 30% EtOAc in hexanes) to yield 2,4-dinitro-N-(2-(2-(prop-2-ynyloxy)ethoxy)ethyl)aniline (s-2b) as a dark yellow solid (50 mg, 45% yield). IR (thin film) 3360 (m), 3285 (m), 3107 (w), 2872 (m), 1621 (s), 1588 (m), 1524 (m), 1425 (w), 1335 (s), 1305 (m), 1133 (m), 1101 (m), 920 (w), 832 (w); $^1$H NMR (500 MHz, CDCl₃) δ 9.15 (d, J=2.6 Hz, 1H), 8.81 (bs, 1H), 8.27 (dd, J=9.4, 2.3 Hz, 1H), 6.96 (d, J=9.5 Hz, 1H), 4.21 (d, J=2.3 Hz, 2H), 3.84 (t, J=5.2 Hz, 2H), 3.74 (m, 4H), 3.61 (q, J=5.2 Hz, 2H), 2.44 (t, J=2.3 Hz, 1H). $^{13}$C NMR (125 MHz, CDCl₃) δ 148.6, 136.3, 130.7, 130.4, 124.4, 114.2, 79.6, 74.9, 70.7, 69.3, 68.9, 58.7, 43.4. HRMS (ES+) calc'd for $C_{13}H_{15}N_3O_6$ (M+H) m/z 310.0994 Found 310.1033.

Scheme S-2. General synthesis of mononitro-PEG₂-alkynes.

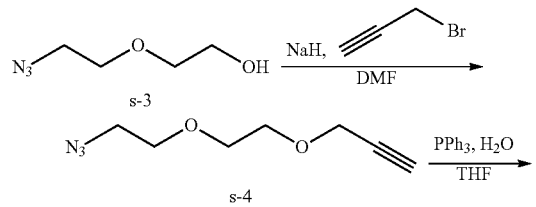

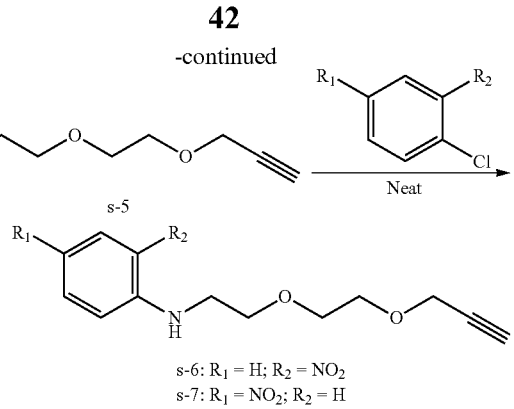

3-(2-(2-azidoethoxy)ethoxy)prop-1-yne (s-4)

2-(2-azidoethoxy)ethanol[1] (s-3) (3 g, 22.89 mmol, 1.0 equiv.) was slowly added to a slurry of NaH (1.10 g, 45.78 mmol, 2 equiv.) in 102.64 mL of DMF in a flame dried flask pre-cooled to 0° C. To the resulting slurry, 80% propargyl bromide in toluene (3.06 mL, 27.47 mmol, 1.2 equiv.), cooled to 0° C., was added slowly. The ice bath was removed and the reaction was allowed to stir at room temperature for an additional 3 hours. The reaction was then re-cooled to 0° C., and 3 mL of cold H₂O was added to quench the reaction, after which the reaction was concentrated under reduced pressure and taken up with saturated NH₄Cl. The reaction was extracted with diethyl ether, dried with Na₂SO₄, concentrated under reduced pressure, and chromatographed (silica gel, 3×25 cm, 0% CH₃OH in CHCl₃, then 10% MeOH in CHCl₃) to yield 3-(2-(2-azidoethoxy)ethoxy)prop-1-yne (s-4) as a dark brown oil (2.79 g, 72.1%). IR (thin film) 3291 (m), 2867 (m), 2099 (s), 1442 (w), 1347 (w), 1285 (m), 1101 (s), 1032 (w), 920 (w), 942 (w), 646 (m); $^1$H NMR (125 MHz, CDCl₃) δ 4.21 (d, J=2.4 Hz, 1H), 3.74-3.65 (m, 3H), 3.40 (t, J=5.1 Hz, 1H), 2.43 (t, J=2.4 Hz, 0H). $^{13}$C NMR (125 MHz, CDCl₃) δ 79.5, 74.6, 70.5, 70.0, 69.1, 58.5, 50.6. HRMS (ES+) calc'd for $C_7H_{11}N_3O_2$ (M+H) m/z 170.0885 Found 170.0924.

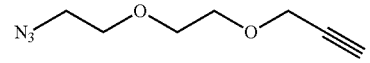

2-(2-(prop-2-ynyloxy)ethoxy)ethanamine (s-5)

3-(2-(2-azidoethoxy)ethoxy)prop-1-yne (s-4) (2 g, 11.83 mmol, 1.0 equiv) was dissolved in THF (30.5 mL). Triphenylphosphine (3.72 g, 14.20 mmol, 1.2 equiv.) and water (0.21 mL, 11.83 mol, 1.0 equiv.) were added to the solution and the reaction was allowed to stir at room temperature for 10 hours. The reaction was concentrated under reduced pressure and chromatographed (5% CH₃OH in CHCl₃, then 5% CH₃OH in CHCl₃+5% Et₃N) to yield 2-(2-(prop-2-ynyloxy)ethoxy)ethanamine (s-5) as a pale green oil (1.35 g, 80%). IR (thin film) 3250 (m), 2863 (m), 2112 (w), 1589 (w), 1443 (w), 1349 (m), 1291 (w), 1093 (s), 1037 (m), 918

(w), 840 (w), 673 (m); ¹H NMR (500 MHz, CDCl₃) δ 4.21 (d, J=2.3 Hz, 2H), 3.73-3.68 (m, 2H), 3.68-3.62 (m, 2H), 3.51 (t, J=5.2 Hz, 2H), 2.87 (t, J=5.2 Hz, 2H), 2.43 (dd, J=2.4 Hz, 1H). ¹³C NMR (125 MHz, CDCl₃) δ 79.7, 74.7, 73.7, 70.3, 69.2, 58.6, 41.9. HRMS (ES+) calc'd for $C_7H_{13}NO_2$ (M+H) m/z 144.0980 Found 144.1019.

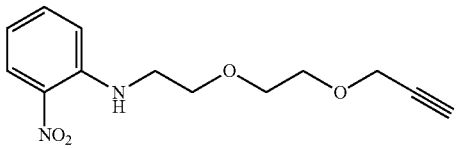 [SMILES: C#CCOCCOCCNc1ccccc1[N+](=O)[O-]]

2-nitro-N-(2-(2-(prop-2-ynyloxy)ethoxy)ethyl)aniline (s-6)

To 1-chloro-2-nitrobenzene (152 mg, 0.97 mmol, 1.0 equiv.) was added neat 2-(2-(prop-2-ynyloxy)ethoxy)ethanamine (s-5) (900 mg, 6.31 mmol, 6.5 equiv.), and the resulting slurry was heated to 100° C. for 6 hours during which time the solid dissolved. At the end of this period, the heating bath was removed, the reaction content was mixed with water (50 mL), and then extracted with CH₂Cl₂ (3×50 mL). The organic layers were combined, dried with Na₂SO₄, concentrated under reduced pressure, and chromatographed (silica gel, 1×25 cm, 0% CH₃OH in CH₂Cl₂, then 10% CH₃OH in CH₂Cl₂) to yield 2-nitro-N-(2-(2-(prop-2-ynyloxy)ethoxy)ethyl)aniline (s-6) as a dark yellow oil (76 mg, 30%). IR (thin film) 3378 (m), 3286 (m), 3085 (w), 2875 (m), 2114 (w), 1616 (s), 1570 (s), 1508 (s), 1417 (m), 1349 (m), 1228 (s), 1093 (s), 1034 (m), 740 (m), 670 (s); ¹H NMR (500 MHz, CDCl₃) δ 8.23 (bs, 1H), 8.18 (dd, J=8.6, 1.6 Hz, 1H), 7.43 (ddd, J=8.6, 7.0, 1.6 Hz, 1H), 6.86 (d, J=8.6 Hz, 1H), 6.65 (ddd, J=8.3, 7.0, 1.2 Hz, 1H), 4.22 (d, J=2.4 Hz, 2H), 3.80 (t, J=5.5 Hz, 2H), 3.73 (d, J=2.4 Hz, 4H), 3.52 (q, J=5.4 Hz, 2H), 2.43 (t, J=2.4 Hz, 1H). ¹³C NMR (125 MHz, CDCl₃) 145.45, 136.13, 132.22, 126.94, 115.39, 113.78, 79.56, 74.61, 70.50, 69.20, 69.19, 58.52, 42.75; HRMS (ES+) calc'd for $C_{13}H_{16}N_2O_4$ (M+H) m/z 265.1144 Found 265.1181.

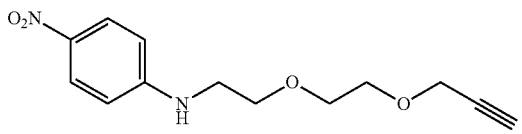 [SMILES: C#CCOCCOCCNc1ccc([N+](=O)[O-])cc1]

4-nitro-N-(2-(2-(prop-2-ynyloxy)ethoxy)ethyl)aniline (s-7)

To 1-chloro-4-nitrobenzene (152 mg, 0.97 mmol, 1.0 equiv.) was added neat 2-(2-(prop-2-ynyloxy)ethoxy)ethanamine (s-5) (900 mg, 6.31 mmol, 6.5 equiv.), and the resulting slurry was heated to 100° C. for 19 hours. At the end of this period, the heating bath was removed, and the reaction content was mixed with water (50 mL) and then extracted with CH₂Cl₂ (3×50 mL). The organic layers were combined, dried with Na₂SO₄, concentrated under reduced pressure, and chromatographed (silica gel, 1×25 cm, 0% EtOAc in CH₂Cl₂, then 30% EtOAc in CH₂Cl₂ to yield 4-nitro-N-(2-(2-(prop-2-ynyloxy)ethoxy)ethyl)aniline (s-7) as a dark yellow oil (40 mg, 16%). IR (thin film) 3351 (m), 3239 (m), 2858 (w), 2112 (w), 1599 (s), 1535 (w), 1500 (w), 1467 (s), 1284 (s), 1086 (s), 1034 (w); ¹H NMR (400 MHz, CDCl₃) δ 8.06 (d, J=9.2 Hz, 2H), 6.53 (d, J=9.2 Hz, 2H), 5.05 (bs, 1H), 4.19 (d, J=2.4 Hz, 2H), 3.76-3.70 (m, 2H), 3.70-3.64 (m, 4H), 3.38 (q, J=5.3 Hz, 2H), 2.45 (t, J=2.4 Hz, 1H). ¹³C NMR (125 MHz, CDCl₃) □ 153.4, 138.0, 126.4, 111.2, 79.5, 74.9, 70.3, 69.1, 69.0, 58.5, 42.9. HRMS (ES+) calc'd for $C_{13}H_{16}N_2O_4$ (M+H) m/z 265.1144 Found 265.1177.

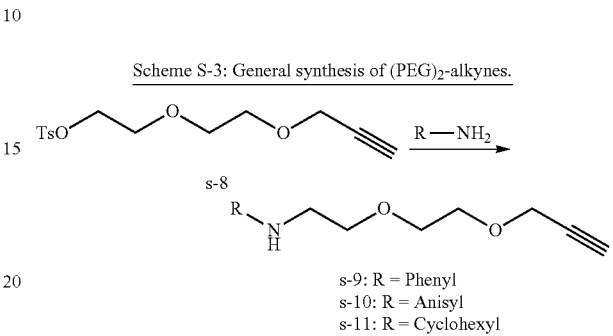

Scheme S-3: General synthesis of (PEG)₂-alkynes.

s-9: R = Phenyl
s-10: R = Anisyl
s-11: R = Cyclohexyl

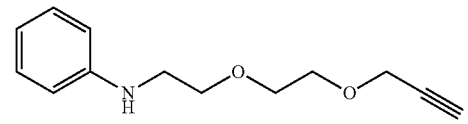 [SMILES: C#CCOCCOCCNc1ccccc1]

N-(2-(2-(prop-2-ynyloxy)ethoxy)ethyl)aniline (s-9)

2-(2-(prop-2-ynyloxy)ethoxy)ethyl 4-methylbenzenesulfonate (s-8)² (100 mg, 0.335 mmol, 0.31 equiv.) was dissolved in aniline (102 mg, 1.10 mmol, 1 equiv.). The reaction was allowed to proceed at 100° C. in a sealed reaction vessel for 5 hours, after which time it was chromatographed (Silica Gel, 25 g RediSep pre-packed column, 0% EtOAc:Hexanes→20% EtOAc:Hexanes) to yield N-(2-(2-(prop-2-ynyloxy)ethoxy)ethyl)aniline (s-9) as a brown oil (39.0 mg, 53.1%). IR (thin film) 3393 (m), 3278 (m), 3052 (w), 2865 (m), 2115 (w), 1603 (s), 1506 (s), 1461 (w), 1320 (w), 1277 (m), 1099 (s), 1030 (w), 750 (s), 693 (s); ¹H NMR (500 MHz, CDCl₃) δ 7.22-7.16 (m, 2H), 6.72 (t, J=7.3 Hz, 1H), 6.67-6.63 (m, 2H), 4.22 (d, J=2.4 Hz, 2H), 4.12 (s, 1H), 3.74-3.70 (m, 4H), 3.70-3.66 (m, 2H), 3.32 (t, J=5.2 Hz, 2H), 2.46 (t, J=2.4 Hz, 1H). ¹³C NMR (125 MHz, CDCl₃) □□ 148.7, 129.6, 117.9, 113.5, 80.0, 75.1, 70.5, 70.1, 69.5, 58.9, 43.9. HRMS (ES+) calc'd for $C_{13}H_{17}NO_2$ (M+H) m/z 220.1293 Found 220.1327.

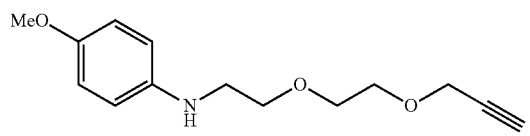 [SMILES: C#CCOCCOCCNc1ccc(OC)cc1]

4-methoxy-N-(2-(2-(prop-2-ynyloxy)ethoxy)ethyl)aniline (s-10)

K₂CO₃ (380 mg, 2.76 mmol, 2.5 equiv.) was added to a solution of 4-methoxyaniline (136 mg, 1.1 mmol, 1 equiv.) in 1 mL of DMF, and the resulting slurry was heated to 100°

C. 2-(2-(prop-2-ynyloxy)ethoxy)ethyl 4-methylbenzenesulfonate (s-8) (100 mg, 0.276 mmol, 0.25 equiv.), dissolved in DMF (1 mL), was then added to the reaction via syringe-pump over 5 hours. The reaction was stirred for an additional 12 hours, after which time it was concentrated under reduced pressure and partially purified (Silica Gel, 12 g RediSep pre-packed column, 0% EtOAc:Hexanes→20% EtOAc:Hexanes→50% EtOAc:Hexanes, followed by EtOAc flush). The material obtained after chromatography was carried directly on to the next step without further purification.

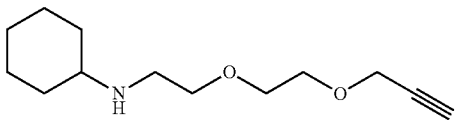 [SMILES: C#CCOCCOCCNC1CCCCC1]

N-(2-(2-(prop-2-ynyloxy)ethoxy)ethyl)cyclohexanamine (s-11)

Cyclohexylamine (150 mg, 1.5 mmol, 1 equiv.) and 2-(2-(prop-2-ynyloxy)ethoxy)ethyl 4-methylbenzenesulfonate (s-8) (100 mg, 0.335 mmol, 0.2 equiv.) were dissolved in 1 mL of ethanol. The reaction was allowed to proceed under microwave irradiation at 80° C. for 10 minutes, after which it was concentrated under reduced pressure and chromatographed (Silica Gel, 25 g RediSep pre-packed column, 10% EtOAc:Hexanes→50% EtOAc:Hexanes, followed by EtOAc flush) to give N-(2-(2-(prop-2-ynyloxy)ethoxy)ethyl)cyclohexanamine (s-10) as a clear oil (28 mg, 37%). IR (thin film) 3253 (w), 2924 (s), 2852 (s), 2113 (w), 1449 (m), 1349 (m), 1263 (w), 1102 (s), 919 (w), 839 (w); $^1$H NMR (400 MHz, CDCl$_3$) δ 4.19 (d, J=2.4 Hz, 2H), 3.70-3.65 (m, 2H), 3.65-3.60 (m, 2H), 3.59 (t, J=5.4 Hz, 2H), 2.80 (t, J=5.4 Hz, 2H), 2.42 (t, J=2.3 Hz, 1H), 2.40-2.34 (m, 1H), 1.90-1.84 (m, 2H), 1.72-1.69 (m, 2H), 1.64-1.54 (m, 1H), 1.30-1.15 (m, 3H), 1.15-0.99 (m, 2H), 0.92-0.81 (m, 1H). $^{13}$C NMR (100 MHz, CDCl$_3$) δ 79.6, 74.6, 70.9, 70.1, 69.0, 58.4, 56.8, 42.3, 33.4, 26.2, 25.1. HRMS (ES+) calc'd for $C_{13}H_{23}NO_2$ (M+H) m/z 226.1762 Found 226.1797.

Scheme S-4: General synthesis of 2 and 3. (2, n = 1; 3, n = 2).

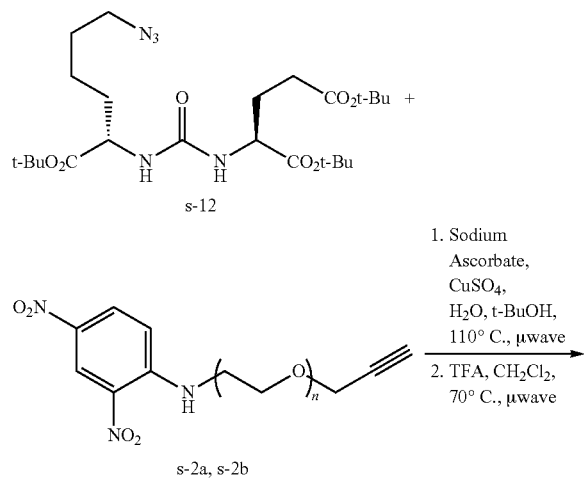

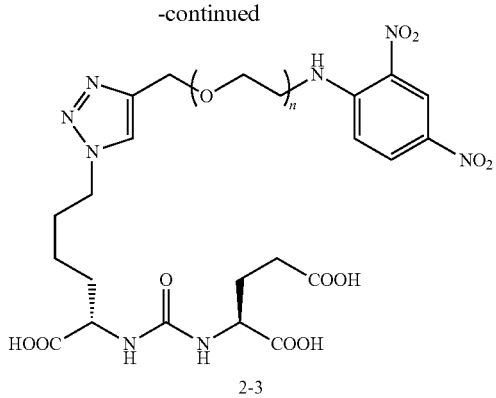

2-3

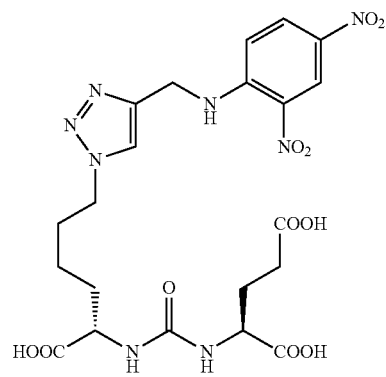 [SMILES: O=C(O)CC[C@H](NC(=O)N[C@@H](CCCCn1cc(CNc2ccc([N+](=O)[O-])cc2[N+](=O)[O-])nn1)C(=O)O)C(=O)O]

(S)-2-(3-((S)-1-carboxy-5-(4-((2,4-dinitrophenylamino)methyl)-1H-1,2,3-triazol-1-yl)pentyl)ureido)pentanedioic acid (1)

2,4-dinitro-N-(prop-2-ynyl)aniline[3] (48.75 mg, 0.220 mmol, 1.1 equiv.) and azide s-12[4] (100 mg, 0.194 mmol, 1 equiv.) were added to a mixture of water (0.694 mL) and t-BuOH (0.694 mL). The slurry was placed in a microwave reaction tube, to which a 0.1 M solution of sodium ascorbate in water (0.388 mL, 0.039 mmol, 0.2 equiv.) and a 0.1 M solution of copper (II) sulfate in water (0.078 mL, 0.008 mmol, 0.04 equiv.) were added. The tube was capped and subjected to microwave irradiation at 110° C. for 20 minutes. The crude mixture was concentrated under reduced pressure, and taken up in 67% trifluoroacetic acid in CH$_2$Cl$_2$ (3 mL). The tube was capped and subjected to microwave irradiation at 70° C. for 2 minutes. The crude mixture was concentrated under reduced pressure, purified via HPLC, and the pure fractions were collected and concentrated under reduced pressure to yield 1 (47.7 mg, 43.6% over two steps) as a yellow solid. IR (thin film) 3367 (br), 2946 (br), 1720 (m), 1619 (s), 1589 (m), 1524 (w), 1425 (w), 1338 (m), 1203 (m), 1137 (m); $^1$H NMR (400 MHz, MeOD) δ 9.05 (d, J=2.6 Hz, 1H), 8.29 (dd, J=9.5, 2.6 Hz, 1H), 8.00 (s, 1H), 7.24 (d, J=9.6 Hz, 1H), 4.82 (s, 2H), 4.41 (t, J=7.0 Hz, 2H), 4.29 (ddd, J=18.6, 8.5, 4.9 Hz, 2H), 2.50-2.33 (m, 2H), 2.20-2.10 (m, 1H), 2.03-1.80 (m, 4H), 1.72-1.62 (m, 1H), 1.48-1.36 (m, 2H). $^{13}$CNMR (125 MHz, DMSO-d$_6$) □□ 174.3, 174.1, 173.7, 157.2, 147.8, 143.1, 135.2, 130.1, 130.0, 123.5, 123.0, 115.7, 52.0, 51.5, 49.3, 38.4, 29.8, 29.4, 27.4, 22.1. HRMS (ES+) calc'd for $C_{21}H_{26}N_8O_{11}$ (M+H) m/z 567.1755 Found 567.1796.

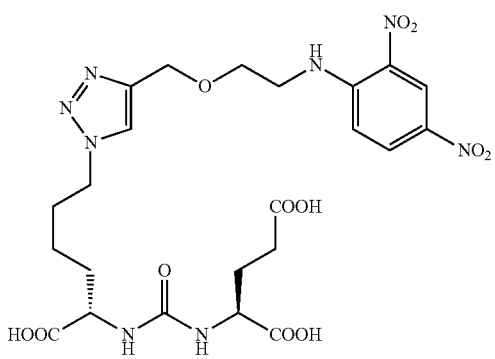 [SMILES: O=C(O)CC[C@H](NC(=O)N[C@@H](CCCCn1cc(COCCNc2ccc([N+](=O)[O-])cc2[N+](=O)[O-])nn1)C(=O)O)C(=O)O]

(S)-2-(3-((S)-1-carboxy-5-(4-((2-(2,4-dinitrophenylamino)ethoxy)methyl)-1H-1,2,3-triazol-1-yl)pentyl)ureido)pentanedioic acid (2)

2,4-dinitro-N-(2-(prop-2-ynyloxy)ethyl)aniline (s-2a) (51.4 mg, 0.194 mmol, 1 equiv.) and azide s-12 (100 mg, 0.194 mmol, 1 equiv.) were added to a mixture of water (0.694 mL) and t-BuOH (0.694 mL). This slurry was placed in a microwave reaction tube, to which a 0.1 M solution of sodium ascorbate in water (0.388 mL, 0.039 mmol, 0.2 equiv.) and 0.1 M solution of copper (II) sulfate in water (0.078 mL, 0.008 mmol, 0.04 equiv.) were added. The tube was capped and subjected to microwave irradiation at 110° C. for 20 minutes. The crude mixture was concentrated under reduced pressure, and taken up in 67% trifluoroacetic acid in $CH_2Cl_2$ (3 mL). The tube was capped and subjected to microwave irradiation at 70° C. for 2 minutes. The crude mixture was concentrated under reduced pressure, purified via HPLC, and the pure fractions were collected and concentrated under reduced pressure to yield 2 (38.0 mg, 32.2% over two steps), as a yellow oil. IR (thin film) 3356 (m), 2938 (m), 1731 (s), 1621 (s), 1586 (m), 1525 (m), 1426 (w), 1336 (s), 1306 (w), 1137 (w), 1087 (m), 833 (w); $^1$H NMR (500 MHz, MeOD) δ 9.00 (d, J=2.2 Hz, 1H), 8.25 (dd, J=9.6, 2.3 Hz, 1H), 7.98 (s, 1H), 7.18 (d, J=9.6 Hz, 1H), 4.68 (s, 2H), 4.41 (t, J=6.9 Hz, 2H), 4.28 (ddd, J=18.1, 8.2, 5.0 Hz, 2H), 3.82 (t, J 5.0 Hz, 2H), 3.67 (t, J=5.0 Hz, 2H), 2.48-2.33 (m, 2H), 2.17-2.10 (m, 1H), 2.01-1.81 (m, 4H), 1.71-1.64 (m, 1H), 1.46-1.35 (m, 2H). $^{13}$CNMR (125 MHz, DMSO-$d_6$) □□ 174.4, 174.1, 173.7, 157.2, 148.3, 143.6, 134.9, 129.9, 129.7, 123.8, 123.6, 115.6, 67.3, 63.4, 52.1, 51.6, 49.1, 42.6, 31.5, 29.9, 29.4, 27.5, 22.1. HRMS (ES+) calc'd for $C_{23}H_{30}N_8O_{12}$ (M+H) m/z 611.2017 Found 611.2074.

(S)-2-(3-((S)-1-carboxy-5-(4-((2-(2-(2,4-dinitrophenylamino)ethoxy)ethoxy)methyl)-1H-1,2,3-triazol-1-yl)pentyl)ureido)pentanedioic acid (3)

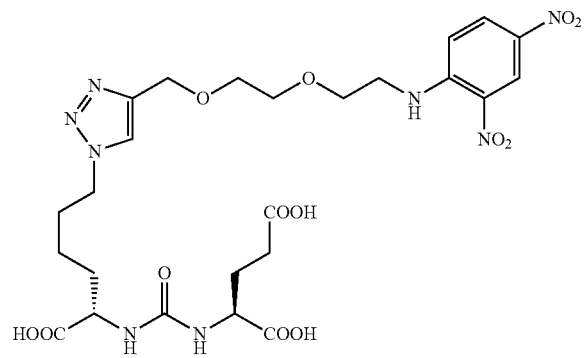 [SMILES: O=C(O)CC[C@H](NC(=O)N[C@@H](CCCCn1cc(COCCOCCNc2ccc([N+](=O)[O-])cc2[N+](=O)[O-])nn1)C(=O)O)C(=O)O]

2,4-dinitro-N-(2-(2-(prop-2-ynyloxy)ethoxy)ethyl)aniline (s-2b) (60 mg, 0.194 mmol, 1 equiv.) and azide s-12 (100 mg, 0.194 mmol, 1 equiv.) were added to a mixture of water (0.694 mL) and t-BuOH (0.694 mL). This slurry was placed in a microwave reaction tube, to which a 0.1 M solution of sodium ascorbate in water (0.388 mL, 0.039 mmol, 0.2 equiv.) and 0.1 M solution of copper (II) sulfate in water (0.078 mL, 0.008 mmol, 0.04 equiv.) were added. The tube was capped and subjected to microwave irradiation at 110° C. for 20 minutes. The crude mixture was concentrated under reduced pressure, and taken up in 67% trifluoroacetic acid in $CH_2Cl_2$ (3 mL). The tube was capped and subjected to microwave irradiation at 70° C. for 2 minutes. The crude mixture was concentrated under reduced pressure, purified via HPLC, and the pure fractions were collected and concentrated under reduced pressure to yield 3 (31.0 mg, 24.6% over two steps) as a yellow oil. IR (thin film) 3360 (m), 2933 (m), 1726 (s), 1621 (s), 1587 (m), 1525 (w), 1425 (w), 1337 (s), 1306 m), 1136 (m); $^1$H NMR (400 MHz, MeOD) □ 9.01 (d, J=2.7 Hz, 1H), 8.26 (dd, J=9.6 Hz, 2.7 Hz, 1H), 7.97 (s, 1H), 7.20 (d, J=9.6 Hz, 1H), 4.63 (s, 2H), 4.41 (t, J=7.0 Hz, 2H), 4.33-4.23 (m, 2H), 3.80 (t, J=5.2 Hz, 2H), 3.72-3.68 (m, 4H), 3.66 (t, J=5.2, 2H), 2.48-2.32 (m, 2H), 2.19-2.08 (m, 1H), 2.00-1.80 (m, 4H), 1.73-163 (m, 1H), 1.46-1.35 (m, 2H). $^{13}$CNMR (125 MHz, DMSO-$d_6$) □ 174.3, 174.1, 173.6, 157.2, 148.2, 143.8, 134.9, 129.9, 129.6, 123.6, 115.6, 69.7, 68.9, 68.2, 63.6, 52.0, 51.5, 49.1, 42.5, 31.4, 29.8, 29.4, 27.4, 22.1. HRMS (ES+) calc'd for $C_{25}H_{34}N_8O_{13}$ (M+H) m/z 655.2279 Found 655.2275.

Scheme S-5: General synthesis of 8-12 (8, $n$ = 0; 9, $n$ = 2; 10, $n$ = 4; 11, $n$ = 8; 12, $n$ = 12) from s-13a-e (a, $n$ = 0; b, $n$ = 2; c, $n$ = 4; d, $n$ = 8; e, $n$ = 12).

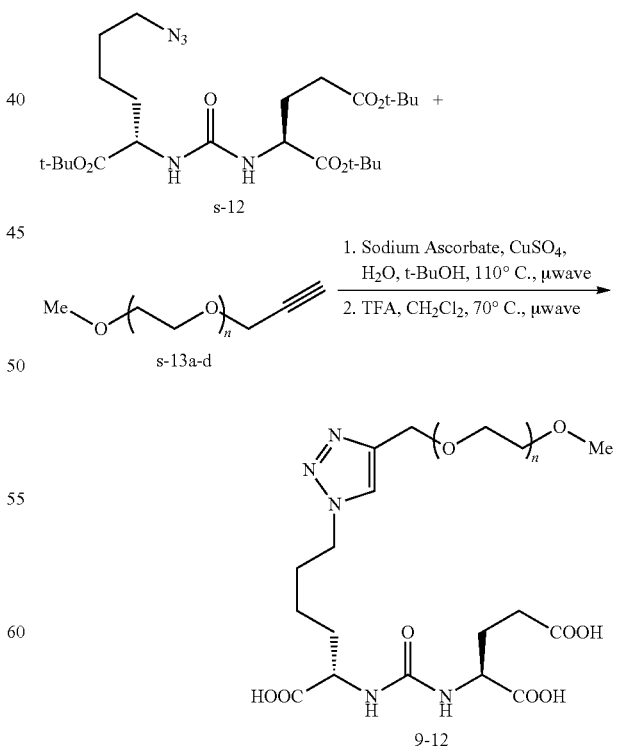

from s-13a-e (a, n=0; b, n=2; c, n=4; d, n=8; e, n=12).

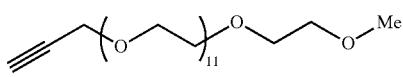

2,5,8,11,14,17,20,23,26,29,32,35,38-tridecaoxahentetracont-40-yne (s-13e)

2,5,8,11,14,17,20,23,26,29,32,35-dodecaoxaheptatriacontan-37-ol (150 mg, 22.89 mmol, 1.0 equiv.) was slowly added to a slurry of NaH (48 mg, 45.78 mol, 8 equiv.) in DMF (1.4 mL) in a flame dried flask pre-cooled to 0° C. 80% propargyl bromide in toluene (36 □L, 27.47 mmol, 1.2 equiv.), cooled to 0° C., was added slowly. The ice bath was removed and the reaction was allowed to stir at room temperature for an additional 2 hours. The reaction was then re-cooled to 0° C., 0.5 mL of ice cold water was added, and the reaction was concentrated under reduced pressure. The remaining residue was redissolved in dichloromethane, then partially purified via silica gel chromatography (10% MeOH in DCM) to remove all the salts. After partial purification, 2,5,8,11,14,17,20,23,26,29,32,35,38-tridecaoxahentetracont-40-yne (s-13e) was obtained as a brown oil that was taken on to the next step without full purification.

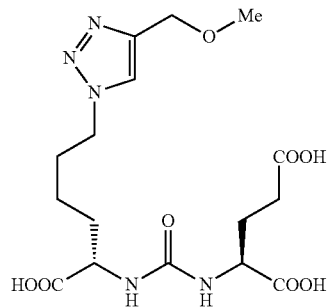 [SMILES: COCc1cn(CCCC[C@H](NC(=O)N[C@@H](CCC(=O)O)C(=O)O)C(=O)O)nn1]

(S)-2-(3-((S)-1-carboxy-5-(4-(methoxymethyl)-1H-1,2,3-triazol-1-yl)pentyl)ureido)pentanedioic acid (8)

Methyl propargyl ether (s-13a) (81.8 mg, 1.16 mmol, 6 equiv.) and azide s-12 (100 mg, 0.194 mmol, 1 equiv.) were added to a mixture of water (0.694 mL) and t-BuOH (0.694 mL). This slurry was placed in a microwave reaction tube to which 0.1 M solution of sodium ascorbate in water (0.388 mL, 0.039 mmol, 0.2 equiv.) and 0.1 M solution of copper (II) sulfate in water (0.078 mL, 0.008 mmol, 0.04 equiv.) were added. The tube was capped and subjected to microwave irradiation at 110° C. for 20 minutes. The crude mixture was concentrated under reduced pressure, and taken up in 67% trifluoroacetic acid in CH$_2$Cl$_2$ (3 mL). The tube was capped and subjected to microwave irradiation at 70° C. for 2 minutes. The crude mixture was concentrated under reduced pressure, purified via HPLC, and the pure fractions were collected and concentrated under reduced pressure to yield 8 (32.9 mg, 41.4% over two steps) as a clear oil. IR (thin film) 3368 (br), 2936 (m), 1670 (s), 1564 (m), 1437 (w), 1193 (s), 1139 (s), 1064 (m), 839 (w), 800 (w), 723 (w). $^1$H NMR (500 MHz, MeOD) δ 8.00 (s, 1H), 4.55 (s, 2H), 4.43 (t, J=7.0 Hz, 2H), 4.36-4.25 (m, 2H), 3.38 (s, 3H), 3.18 (s, OH), 2.48-2.35 (m, 2H), 2.19-2.12 (m, 1H), 2.02-1.82 (m, 4H), 1.75-1.64 (m, 1H), 1.48-1.36 (m, 2H). $^{13}$CNMR (125 MHz, MeOD) □□176.5, 176.2, 175.8, 160.1, 145.6, 125.2, 66.2, 58.4, 53.7, 53.5, 51.3, 32.8, 31.1, 30.7, 28.8, 23.4. HRMS (ES+) calc'd for C$_{16}$H$_{25}$N$_5$O$_8$ (M+H) m/z 416.1737 Found 415.2019.

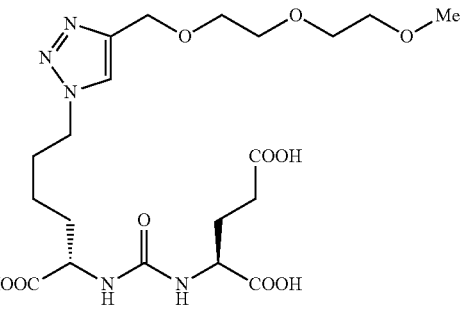

(S)-2-(3-((S)-1-carboxy-5-(4-((2-(2methoxyethoxy)ethoxy)methyl)-1H-1,2,3-triazol-1-yl)pentyl)ureido)pentanedioic acid (9)

3-(2-(2-methoxyethoxy)ethoxy)prop-1-yne (s-13b)[5] (30.7 mg, 0.194 mmol, 1 equiv.) and azide s-12 (100 mg, 0.194 mmol, 1 equiv.) were added to a mixture of water (0.694 mL) and t-BuOH (0.694 mL). This slurry was placed in a microwave reaction tube, to which a 0.1 M solution of sodium ascorbate in water (0.388 mL, 0.039 mmol, 0.2 equiv.) and 0.1 M solution of copper (II) sulfate in water (0.078 mL, 0.008 mmol, 0.04 equiv.) were added. The tube was capped and subjected to microwave irradiation at 110° C. for 20 minutes. The crude mixture was concentrated under reduced pressure, and taken up in 67% trifluoroacetic acid in CH$_2$Cl$_2$ (3 mL). The tube was capped and subjected to microwave irradiation at 70° C. for 2 minutes. The crude mixture was concentrated under reduced pressure, purified via HPLC, and the pure fractions were collected and concentrated under reduced pressure to yield 9 (30.6 mg, 31.5% over two steps) as a clear oil. IR (thin film) 3346 (br), 2931 (m), 1734 (s), 1642 (m), 1562 (s), 1451 (w), 1201 (s), 1087 (s); $^1$H NMR (400 MHz, MeOD) δ 8.01 (s, 1H), 4.65 (s, 2H), 4.43 (t, J=7.0 Hz, 2H), 4.33-4.24 (m, 2H), 3.69-3.64 (m, 4H), 3.64-3.60 (m, 2H), 3.56-3.49 (m, 2H), 3.33 (s, 3H), 2.46-2.34 (m, 2H), 2.16-2.11 (m, 1H), 2.00-1.82 (m, 4H), 1.71-1.64 (m, 1H), 1.48-1.31 (m, 2H). $^{13}$CNMR (125 MHz, CD$_3$OD) □ 176.4, 176.1, 175.8, 160.1, 145.8, 125.3, 72.9, 71.5, 71.3, 70.8, 64.8, 59.1, 53.7, 53.5, 51.3, 32.8, 31.1, 30.7, 28.8, 23.4. HRMS (ES+) calc'd for C$_{20}$H$_{33}$N$_5$O$_{10}$ (M+H) m/z 504.2261 Found 504.2590.

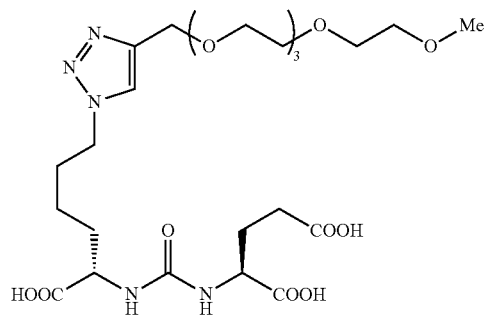

(S)-2-(3-((S)-5-(4-2,5,8,11,14-pentaoxapentadecyl-1H-1,2,3-triazol-1-yl-1-carboxypentyl)ureido)pentanedioic acid (10)

2,5,8,11,14-pentaoxaheptadec-16-yne (s-13c)[5] (52 mg, 0.194 mmol, 1 equiv.) and azide s-12 (100 mg, 0.194 mmol, 1 equiv.) were added to a mixture of water (0.694 mL) and t-BuOH (0.694 mL). This slurry was placed in a microwave reaction tube, to which a 0.1 M solution of sodium ascorbate in water (0.388 mL, 0.039 mmol, 0.2 equiv.) and 0.1 M solution of copper (II) sulfate in water (0.078 mL, 0.008 mmol, 0.04 equiv.) were added. The tube was capped and subjected to microwave irradiation at 110° C. for 20 minutes. The crude mixture was concentrated under reduced pressure, and taken up in 67% trifluoroacetic acid in $CH_2Cl_2$ (3 mL). The tube was capped and subjected to microwave irradiation at 70° C. for 2 minutes. The crude mixture was concentrated under reduced pressure, purified via HPLC, and the pure fractions were collected and concentrated under reduced pressure to yield 10 (19.8 mg, 15.9% over two steps) as a clear oil. IR (thin film) 3323 (br), 2921 (m), 1734 (s), 1642 (w), 1562 (m), 1452 (w), 1201 (m), 1089 (m), 845 (w); TH NMR (500 MHz, MeOD) δ 8.04 (s, 1H), 4.65 (s, 2H), 4.44 (t, J=7.0 Hz, 2H), 4.34-4.24 (m, 2H), 3.70-3.65 (m, 4H), 3.65-3.58 (m, 12H), 3.52 (dd, J=5.6, 3.6 Hz, 2H), 3.34 (s, 3H), 2.47-2.35 (m, 2H), 2.19-2.09 (m, 1H), 2.02-1.82 (m, 4H), 1.72-1.65 (m, 1H), 1.45-1.36 (m, 2H). $^{13}$CNMR (125 MHz, DMSO-d$_6$) □□□ 176.4, 176.1, 160.1, 145.7, 125.3, 72.9, 71.5, 71.3, 70.8, 64.8, 59.1, 53.7, 53.5, 51.3, 32.8, 31.1, 30.7, 28.8, 23.4. HRMS (ES+) calc'd for $C_{24}H_{41}N_5O_{12}$ (M+H) m/z 592.2785 Found 592.2783.

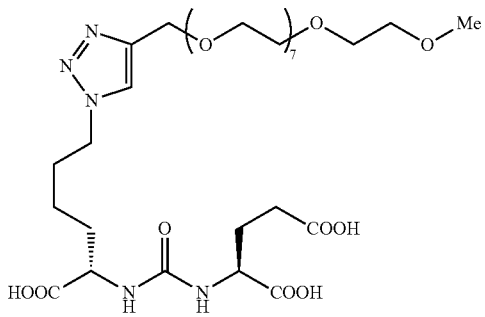

(S)-2-(3-((S)-5-(4-2,5,8,11,14,17,20,23,26-nonaoxaheptacosyl-1H-1,2,3-triazol-1-yl)-1-carboxypentyl)ureido)pentanedioic acid (11)

2,5,8,11,14,17,20,23,26-nonaoxanonacos-28-yne (s-13d)[6] (41 mg, 0.097 mmol, 1 equiv.) and azide s-12 (50 mg, 0.097 mmol, 1 equiv.) were added to a mixture of water (0.350 mL) and t-BuOH (0.350 mL). This slurry was placed in a microwave reaction tube, to which a 0.1 M solution of sodium ascorbate in water (0.194 mL, 0.019 mmol, 0.2 equiv.) and 0.1 M solution of copper (II) sulfate in water (0.039 mL, 0.004 mmol, 0.04 equiv.) were added. The tube was capped and subjected to microwave irradiation at 110° C. for 20 minutes. The crude mixture was concentrated under reduced pressure, and taken up in 67% trifluoroacetic acid in $CH_2Cl_2$ (3 mL). The tube was capped and subjected to microwave irradiation at 70° C. for 2 minutes. The crude mixture was concentrated under reduced pressure, purified via HPLC, and the pure fractions were collected and concentrated under reduced pressure to yield 11 (9.6 mg, 21.4% over two steps) as a clear oil. IR (thin film) 3332 (br), 2919 (m), 2875 (m), 1734 (s), 1557 (m), 1452 (w), 1203 (s), 1088 (s), 946 (w), 850 (w); $^1$H NMR (400 MHz, MeOD) δ 8.00 (s, 1H), 4.64 (s, 2H), 4.42 (t, J=6.9 Hz, 2H), 4.35-4.23 (m, 2H), 3.66 (s, 4H), 3.62 (m, J=5.5, 1.1 Hz, 26H), 3.56-3.52 (m, 2H), 3.36 (d, J=1.1 Hz, 3H), 2.45-2.41 (m, 2H), 2.22-2.07 (m, 1H), 1.98-1.82 (m, 4H), 1.72-1.64 (m, 1H), 1.44-1.35 (m, 2H). $^{13}$CNMR (125 MHz, MeOD) □□ 176.4, 176.1, 175.8, 160.1, 145.9, 125.2, 73.0, 71.5, 71.3, 70.8, 64.9, 59.1, 53.7, 53.5, 51.2, 32.8, 31.1, 30.7, 28.8, 23.4. HRMS (ES+) calc'd for $C_{32}H_{57}N_5O_{16}$ (M+H) m/z 768.3834 Found 768.3865.

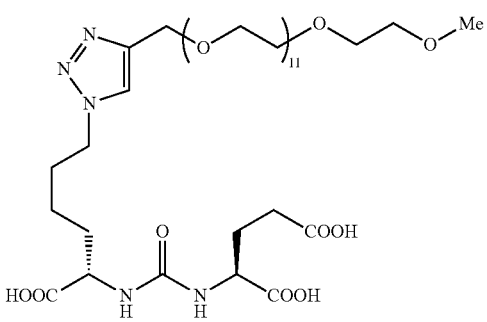

(S)-2-(3-((S)-5-(4-2,5,8,11,14,17,20,23,26,29,32,35,38-tridecaoxanonatriacontyl-1H-1,2,3-triazol-1-yl)-1-carboxypentyl)ureido)pentanedioic acid (12)

Crude 2,5,8,11,14,17,20,23,26,29,32,35,38-tridecaoxahentetracont-40-yne (s-13e) (58 mg, 0.097 mmol, 1 equiv.) and azide s-12 (50 mg 0.097 mmol, 1 equiv.) were added to a mixture of water (0.350 mL) and t-BuOH (0.350 mL). This slurry was placed in a microwave reaction tube, to which a 0.1 M solution of sodium ascorbate in water (0.194 mL, 0.019 mmol, 0.2 equiv.) and 0.1 M solution of copper (II) sulfate in water (0.039 mL, 0.004 mmol, 0.04 equiv.) were added. The tube was capped and subjected to microwave irradiation at 110° C. for 20 minutes. The crude mixture was concentrated under reduced pressure, and taken up in 67% trifluoroacetic acid in $CH_2Cl_2$ (3 mL). The tube was capped and subjected to microwave irradiation at 70° C. for 2 minutes. The crude mixture was concentrated under reduced pressure, purified via HPLC, and the pure fractions were collected and concentrated under reduced pressure to yield 12 (13.0 mg, 9.6%, 3 steps) as a clear oil. IR (thin film) 3369 (br), 2878 (s), 1673 (s), 1561 (w), 1456 (w), 1351 (w), 1200 (s), 1105 (s), 950 (w), 836 (w), 800 (w), 721 (w); $^1$H NMR (500 MHz, MeOD) δ 8.00 (s, 1H), 4.64 (s, 2H), 4.42 (t, J=7.0 Hz, 2H), 4.33-4.24 (m, 2H), 3.69-3.59 (m, 46H), 3.56-3.52 (m, 2H), 2.48-2.34 (m, 2H), 2.19-2.09 (m, 1H), 2.02-1.81 (m, 4H), 1.71-1.64 (m, 1H), 1.45-1.33 (m, 2H). $^{13}$CNMR (125 MHz, MeOD) □□ 176.4, 176.1, 175.8, 160.1, 145.9, 125.2, 72.9, 71.5, 71.3, 70.7, 65.0, 59.1, 53.7, 53.5, 51.1, 32.9, 31.1, 30.8, 28.9, 23.4. LCMS (ES+) calc'd for $C_{40}H_{73}N_5O_{20}$ (M+H) m/z 944.49 Found 944.72.

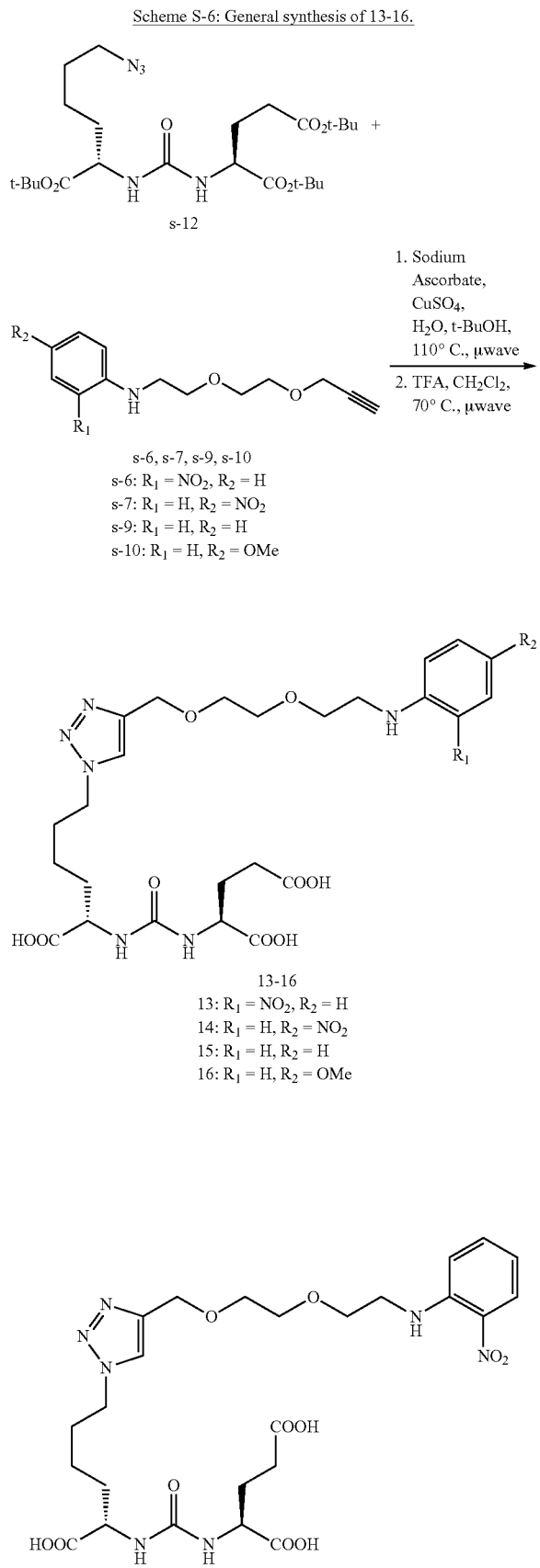

Scheme S-6: General synthesis of 13-16.

s-6, s-7, s-9, s-10
s-6: R₁ = NO₂, R₂ = H
s-7: R₁ = H, R₂ = NO₂
s-9: R₁ = H, R₂ = H
s-10: R₁ = H, R₂ = OMe

1. Sodium Ascorbate, CuSO₄, H₂O, t-BuOH, 110° C., μwave
2. TFA, CH₂Cl₂, 70° C., μwave 13-16
13: R₁ = NO₂, R₂ = H
14: R₁ = H, R₂ = NO₂
15: R₁ = H, R₂ = H
16: R₁ = H, R₂ = OMe

(S)-2-(3-((S)-1-carboxy-5-(4-((2-(2-(2-nitrophenylamino)ethoxy)ethoxy)methyl)-1H-1,2,3-triazol-1-yl)pentyl)ureido)pentanedioic acid (13)

2-nitro-N-(2-(2-(prop-2-ynyloxy)ethoxy)ethyl)aniline (s-6) (51.2 mg, 0.194 mmol, 1 equiv.) and azide s-12 (100 mg, 0.194 mmol, 1 equiv.) were added to a mixture of water (0.694 mL) and t-BuOH (0.694 mL). This slurry was placed in a microwave reaction tube, to which a 0.1 M solution of sodium ascorbate in water (0.388 mL, 0.039 mmol, 0.2 equiv.) and 0.1 M solution of copper (II) sulfate in water (0.078 mL, 0.008 mmol, 0.04 equiv.) were added. The tube was capped and subjected to microwave irradiation at 110° C. for 20 minutes. The crude mixture was concentrated under reduced pressure, and taken up in 67% trifluoroacetic acid in CH₂Cl₂ (3 mL). The tube was capped and subjected to microwave irradiation at 70° C. for 2 minutes. The crude mixture was concentrated under reduced pressure, purified via HPLC, and the pure fractions were collected and concentrated under reduced pressure to yield 13 (36.5 mg, 31.0% over two steps) as a dark yellow oil. IR (thin film) 3335 (br), 2923 (m), 1722 (s), 1668 (m), 1602 (s), 1561 (w), 1470 (w), 1308 (s), 1187 (m), 1111 (w), 998 (w), 836 (w); $^1$H NMR (500 MHz, MeOD) δ 8.12 (dd, J=8.6, 1.6 Hz, 1H), 7.98 (s, 1H), 7.49 (ddd, J=8.6, 6.9, 1.6 Hz, 1H), 7.02 (dd, J=8.7, 0.9 Hz, 1H), 6.67 (ddd, J=8.3, 6.9, 1.2 Hz, 1H), 4.65 (s, 2H), 4.41 (t, J=7.1 Hz, 2H), 4.30 (ddd, J=17.8, 8.4, 5.0 Hz, 2H), 3.78 (t, J=5.3 Hz, 2H), 3.71 (m, 4H), 3.53 (t, J=5.3 Hz, 2H), 2.44-2.40 (m, 2H), 2.21-2.10 (m, 1H), 2.00-1.81 (m, 4H), 1.72-1.65 (m, 1H), 1.47-1.35 (m, 2H). $^{13}$CNMR (125 MHz, DMSO-d₆) □174.4, 174.1, 173.7, 157.2, 145.2, 143.9, 136.6, 131.0, 126.2, 123.6, 115.4, 114.7, 69.6, 68.9, 68.4, 63.6, 52.1, 51.6, 49.1, 42.0, 31.5, 29.9, 29.4, 27.5, 22.1. HRMS (ES+) calc'd for C₂₅H₃₅N₇O₁₁ (M+H) m/z 610.2428 Found 610.2471.

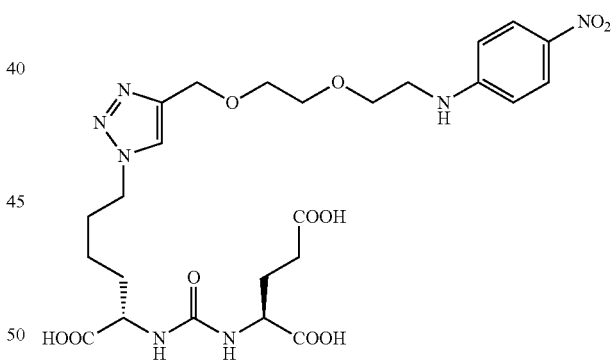

(S)-2-(3-((S)-1-carboxy-5-(4-((2-(2-(4-nitrophenylamino)ethoxy)ethoxy)methyl)-1H-1,2,3-triazol-1-yl)pentyl)ureido)pentanedioic acid (14)

4-nitro-N-(2-(2-(prop-2-ynyloxy)ethoxy)ethyl)aniline (s-7) (34.2 mg, 0.129 mmol, 1 equiv.) and azide s-12 (66.7 mg, 0.129 mmol, 1 equiv.) were added to a mixture of water (0.600 mL) and t-BuOH (0.600 mL). This slurry was placed in a microwave reaction tube, to which a 0.1 M solution of sodium ascorbate in water (0.260 mL, 0.026 mmol, 0.2 equiv.) and a 0.1 M solution of copper (II) sulfate in water (0.051 mL, 0.005 mmol, 0.04 equiv.) were added. The tube was capped and subjected to microwave irradiation at 110° C. for 20 minutes. The crude mixture was concentrated

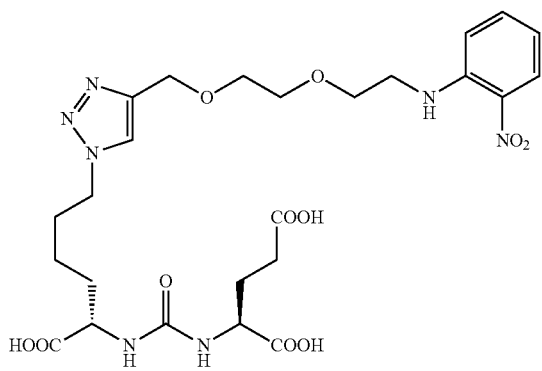 [SMILES: O=C(O)CC[C@H](NC(=O)N[C@@H](CCCCn1cc(COCCOCCNc2ccccc2[N+](=O)[O-])nn1)C(=O)O)C(=O)O]

under reduced pressure, and taken up in 67% trifluoroacetic acid in CH$_2$Cl$_2$ (3 mL). The tube was capped and subjected to microwave radiation at 70° C. for 2 minutes. The crude mixture was concentrated under reduced pressure, purified via HPLC, and the pure fractions were collected and concentrated under reduced pressure to yield 14 (21.7 mg, 27.6% over two steps) as a yellow oil. IR (thin film) 3335 (br), 2924 (m), 2870 (m), 1722 (s), 1668 (m), 1602 (s), 1561 (m), 1505 (w), 1470 (w), 1308 (s), 1187 (m), 1118 (m), 837 (w); $^1$H NMR (500 MHz, MeOD) δ 8.01 (d, J=10.4 Hz, 1H), 7.95 (s, 1H), 6.64 (d, J=10.4 Hz, 1H) 4.63 (s, 2H), 4.39 (t, J=7.0 Hz, 2H), 4.29 (ddd, J=16.4, 8.4, 5.0 Hz, 2H), 3.71-3.62 (m, 6H), 3.38 (t, J=5.4 Hz, 2H), 2.47-2.34 (m, 2H), 2.19-2.08 (m, 1H), 1.99-1.80 (m, 4H), 1.71-1.64 (m, 1H), 1.42-1.36 (m, 2H). $^{13}$CNMR (125 MHz, DMSO-d$_6$) □ 174.4, 174.1, 173.7, 157.3, 154.6, 143.8, 135.6, 126.2, 123.7, 110.8, 69.6, 68.9, 68.6, 63.5, 52.1, 51.6, 49.1, 42.3, 31.5, 29.9, 29.4, 27.5, 22.1. HRMS (ES+) calc'd for C$_{25}$H$_{35}$N$_7$O$_{11}$ (M+H) m/z 610.2428 Found 610.2468.

3.27 (t, J=5.4 Hz, 2H), 2.46-2.34 (m, 2H), 2.19-2.08 (m, 1H), 1.98-1.79 (m, 4H), 1.71-1.62 (m, 1H), 1.44-1.32 (m, 2H). $^{13}$CNMR (125 MHz, DMSO-d$_6$) □□ 174.4, 174.1, 173.7, 157.3, 146.2, 143.8, 129.1, 123.7, 118.3, 114.2, 69.6, 68.9, 68.2, 63.6, 52.1, 51.7, 49.1, 44.1, 31.5, 29.9, 29.4, 27.5, 22.1. HRMS (ES+) calc'd for C$_{25}$H$_{36}$N$_6$O$_9$ (M+H) m/z 565.2577 Found 565.2621.

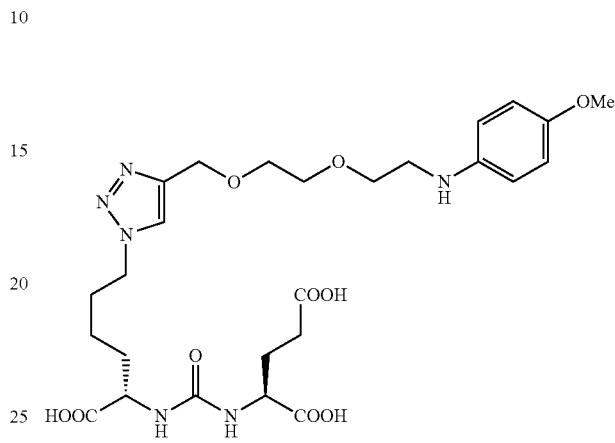

(S)-2-(3-((S)-1-carboxy-5-(4-((2-(2-(4-methoxyphenylamino)ethoxy)ethoxy)methyl)-1H-1,2,3-triazol-1-yl)pentyl)ureido)pentanedioic acid (16)

4-methoxy-N-(2-(2-(prop-2-ynyloxy)ethoxy)ethyl)aniline (s-10) (34 mg, 0.137 mmol, 1 equiv.) and azide s-12 (70 mg, 0.137 mmol, 1 equiv.) were added to a mixture of water (1 mL) and t-BuOH (1 mL). This slurry was placed in a microwave reaction tube, to which a 0.1 M solution of sodium ascorbate (6 mg, 0.034 mmol, 0.25 equiv.) and a 0.1 M solution of copper (II) sulfate in water (0.068 mL, 0.007 mmol, 0.05 equiv.) were added. The tube was capped and subjected to microwave irradiation at 110° C. for 20 minutes. The crude mixture was concentrated under reduced pressure, and taken up in 67% trifluoroacetic acid in CH$_2$Cl$_2$ (3 mL). The tube was capped and subjected to microwave irradiation at 70° C. for 2 minutes. The crude mixture was concentrated under reduced pressure, purified via HPLC, and the pure fractions were collected and concentrated under reduced pressure to yield 16 (9.3 mg, 11.8% over three steps) as a light brown oil. IR (thin film) 3347 (br), 2956 (m), 1728 (s), 1670 (s), 1564 (m), 1513 (m), 1443 (w), 1259 (w), 1200 (s), 1137 (m), 1029 (w), 837 (w); $^1$H NMR (400 MHz, MeOD) δ 8.01 (s, 1H), 7.45-7.39 (m, 2H), 7.09-7.04 (m, 2H), 4.68 (s, 2H), 4.42 (t, J=7.0 Hz, 2H), 4.30 (dd, J=8.6, 5.0 Hz, 1H), 4.22 (dd, J=8.5, 4.9 Hz, 1H), 3.87 (s, 3H), 3.75-3.73 (m, 2H), 3.72-3.68 (m, 2H), 3.68-3.64 (m, 2H), 3.57-3.50 (m, 2H), 2.49-2.33 (m, 2H), 2.17-2.12 (m, 1H), 2.01-1.79 (m, 4H), 1.72-1.57 (m, 1H), 1.45-1.32 (m, 2H). $^{13}$CNMR (125 MHz, DMSO-d$_6$) □□ 174.4, 174.1, 173.7, 157.2, 143.7, 126.5, 123.7, 121.6, 117.4, 114.9, 69.7, 68.8, 65.9, 63.5, 55.4, 52.1, 51.6, 49.1, 48.4, 31.5, 29.9, 29.4, 27.5, 22.11 HRMS (ES+) calc'd for C$_{26}$H$_{38}$N$_6$O$_{10}$ (M+H) m/z 595.2683 Found 595.2722.

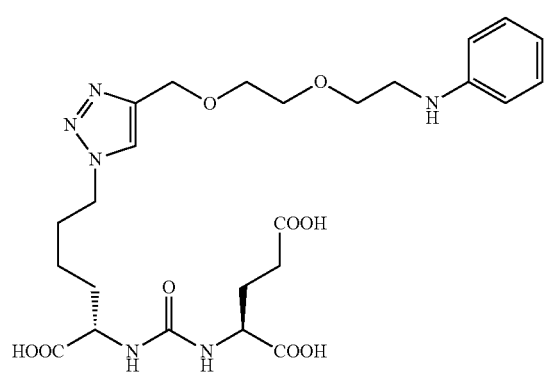 [SMILES: O=C(O)CC[C@H](NC(=O)N[C@@H](CCCCn1cc(COCCOCCNc2ccccc2)nn1)C(=O)O)C(=O)O]

(S)-2-(3-((S)-1-carboxy-5-(4-((2-(2-(phenylamino)ethoxy)ethoxy)methyl)-1H-1,2,3-triazol-1-yl)pentyl)ureido)pentanedioic acid (15)

N-(2-(2-(prop-2-ynyloxy)ethoxy)ethyl)aniline (s-9) (35 mg, 0.160 mmol, 1 equiv.) and azide 31 (82 mg, 0.160 mmol, 1 equiv.) were added to a mixture of water (1 mL) and t-BuOH (1 mL). This slurry was placed in a microwave reaction tube, to which a 0.1 M solution of sodium ascorbate in water (7.8 mg, 0.04 mmol, 0.25 equiv.) and a 0.1 M solution of copper (II) sulfate in water (0.080 mL, 0.008 mmol, 0.05 equiv.) were added. The tube was capped and subjected to microwave irradiation at 110° C. for 20 minutes. The crude mixture was concentrated under reduced pressure, and taken up in 67% trifluoroacetic acid in CH$_2$Cl$_2$ (3 mL). The tube was capped and subjected to microwave irradiation at 70° C. for 2 minutes. The crude mixture was concentrated under reduced pressure, purified via HPLC, and the pure fractions were collected and concentrated under reduced pressure to yield 15 (13.7 mg, 15.3% over two steps) as a light brown oil. IR (thin film) 3369 (br), 2939 (m), 1664 (s), 1563 (m), 1497 (w), 1438 (w), 1188 (s), 1134 (s), 837 (w), 798 (w), 753 (w), 721 (w); $^1$H NMR (400 MHz, MeOD) δ 8.02 (s, 1H), 7.58-7.49 (m, 5H), 4.64 (s, 2H), 4.37 (t, J=7.0 Hz, 2H), 4.33-4.24 (m, 2H), 3.70-3.63 (m, 6H),

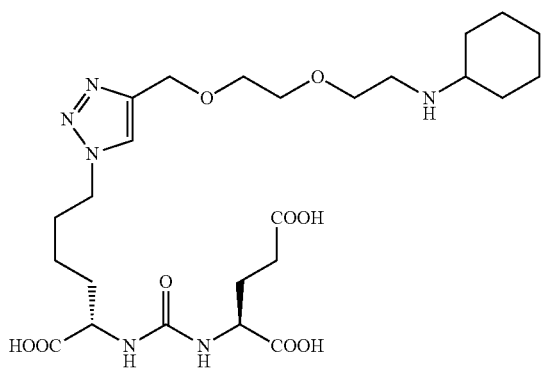 [SMILES: O=C(O)CC[C@H](NC(=O)N[C@@H](CCCCn1cc(COCCOCCNC2CCCCC2)nn1)C(=O)O)C(=O)O]

(S)-2-(3-((S)-1-carboxy-5-(4-((2-(2-(cyclohexy-
lamino)ethoxy)ethoxy)methyl)-1H-1,2,3-triazol-1-
yl)pentyl)ureido)pentanedioic acid (17)

N-(2-(2-(prop-2-ynyloxy)ethoxy)ethyl)cyclohexanamine (s-11) (16 mg, 0.071 mmol, 1 equiv.) and azide s-12 (16 mg, 0.071 mmol, 1 equiv.) were added to a mixture of water (0.500 mL) and t-BuOH (0.500 mL). This slurry was placed in a microwave reaction tube, to which a 0.1 M solution of sodium ascorbate in water (3.4 mg, 0.018 mol, 0.25 equiv.) and a 0.1 M solution of copper (II) sulfate in water (0.0355 mL, 0.00355 mmol, 0.05 equiv.) were added. The tube was capped and subjected to microwave irradiation at 110° C. for 20 minutes. The crude mixture was concentrated, and taken up in 67% trifluoroacetic acid in $CH_2Cl_2$ (3 mL). The tube was capped and subjected to microwave irradiation at 70° C. for 2 minutes. The crude mixture was concentrated under reduced pressure, purified via HPLC, and the pure fractions were collected and concentrated under reduced pressure to yield 17 (7.9 mg, 19.7% over two steps) as a clear oil. IR (thin film) 3344 (w), 2939 (m), 2865 (w), 1732 (m), 1670 (s), 1453 (w), 1201 (s), 1136 (m), 1088 (w), 799 (w); $^1$H NMR (400 MHz, MeOD) δ 8.02 (s, 1H), 4.65 (s, 2H), 4.43 (t, J=7.0 Hz, 2H), 4.34-4.21 (m, 3H), 3.76-3.64 (m, 7H), 3.26-3.19 (m, 2H), 3.08 (s, 1H), 2.50-2.34 (m, 2H), 2.16-2.10 (m, 3H), 2.03-1.81 (m, 6H), 1.70-1.63 (m, 2H), 1.46-1.28 (m, 7H), 1.28-1.14 (m, 1H). $^{13}$CNMR (125 MHz, DMSO-$d_6$) □□ 174.2, 173.9, 173.5, 157.1, 143.7, 123.7, 69.7, 69.5, 68.7, 68.3, 65.8, 63.4, 56.0, 49.1, 43.1, 31.4, 29.8, 29.3, 28.3, 27.4, 24.6, 23.8, 22.1. HRMS (ES+) calc'd for $C_{25}H_{42}N_6O_9$ (M+H) m/z 571.3047 Found 571.3091.

Biological Assays and Crystallographic Data
Measurement of PSMA $K_m$:

A 10 mM solution of N-acetyl-aspartylglutamate (NAAG) in 40 mM NaOH, and was then diluted in Reaction Buffer (100 mM Tris-HCl, pH 7.5) to a final NAAG concentration of 40 □M. The solution was added to a 384 well plate (20 □L per well). For Km measurements and controls the NAAG solution was serially diluted 2-fold in Reaction Buffer to obtain final NAAG concentrations ranging from 40 □M-312.5 nM. rhPSMA (20 ng/mL in Reaction Buffer, 20 □L, R&D Research) was then added to each well. Reaction Buffer (20 □L) was added to the $K_m$ control series. The plate was incubated at room temperature for 15 min, and then heated to 95° C. for 3 minutes. The plate was allowed to cool to room temperature, and glutamic acid levels were measured using a commercially available Amplex®—Red Glutamic Acid/Glutamate Oxidase Assay Kit (Invitrogen). Fluorescence intensities were measured using a Synergy 2 multiwell plate reader (Biotek), fitted with excitation and emission filters of 545 nm and 590 nm, respectively. The $K_m$ was calculated using nonlinear least-squares regression algorithms contained in the GraphPad Prism software package to provide an average $K_m$ value for this enzymatic reaction of 0.925 μM. This value is consistent with that reported in the literature[7] and was employed in subsequent $K_i$ calculations (see below).

PSMA Inhibition Assay:

For $IC_{50}$ measurements, inhibitors were dissolved in Reaction Buffer containing μM NAAG to a final volume of 100 μL. Then, 25 μL of this solution was transferred to each of three wells in a microtiter plate, and 5 μL aliquots were serially diluted into 20 μL of solution containing 40 μM NAAG over 10 wells (5-fold dilutions). Inhibitor concentration therefore ranged over 6 orders of magnitude in these experiments. rhPSMA (20 ng/mL in Reaction Buffer, 20 μL, R&D Research) was then added to each well. The plate was incubated at room temperature for 15 min, and then heated to 95° C. for 3 minutes. The plate was allowed to cool to room temperature, and glutamic acid levels were measured using a commercially available Amplex®-Red Glutamic Acid/Glutamate Oxidase Assay Kit (Invitrogen). Fluorescence intensities were measured using a Synergy 2 multiwell plate reader (Biotek), fitted with excitation and emission filters of 545 nm and 590 nm, respectively. The concentration of inhibitors giving 50% inhibition of enzyme activity ($IC_{50}$) was calculated from the least-squares regression line of the residual enzymatic activity plotted as a function of logarithmic inhibitor concentrations using algorithms contained in the GraphPad Prism software package. $K_i$ values were obtained from $IC_{50}$ values using the Cheng-Prusoff equation, a substrate concentration of 20 μM, and a $K_m$ value of 0.925 μM. All reported values in Tables 1 and 2 represent the average of at least three replicates±standard deviation.

rhPSMA Expression and Purification

The extracellular domain of human PSMA (amino acids 44-750) was expressed and purified as described previously and we designate this construct rhPSMA[8]. For crystallization experiments, rhPSMA was dialyzed against 20 mM MOPS, 20 mM NaCl, pH 7.4, and concentrated to 10 mg/mL.

Crystallization, Data Collection and Processing

The stock solutions of individual inhibitors at 50 mM were prepared in 25% (v/v) acetonitrile in water. Diffraction quality crystals of rhPSMA/ARMs complexes were grown at 293 K by vapor diffusion in hanging drops. The stock solution of rhPSMA was mixed in a 10:1 ratio with an ARM and hanging drops formed by mixing equal volumes of the protein and reservoir solutions (33% (v/v) pentaerythritol propoxylate PO/OH 5/4 (Hampton Research), 0.5% (w/v) PEG 3350, and 100 mM Tris-HCl, pH 8.0). Prior to the data collection, the crystals were flash-frozen in liquid nitrogen directly from the hanging drop. Each of the four datasets was collected from a single crystal at 100 K using synchrotron radiation at the SER-CAT sector 22 beamlines of the Advanced Photon Source (Argonne, Ill., USA) equipped with MAR225 or MAR300 CCD detectors. Data were integrated and scaled with the HKL2000 package[9].

Electron Map Density Fit

Individual compounds were fit into the positive electron density in the final stages of the refinement. For all four inhibitors, clear interpretable densities were observed for the C-terminal part encompassing the P1' glutarate, the urea linkage, the lysine linker, and the triazole ring Structure Solution and Refinement Structure determination of rhPSMA/ARMs complexes was carried out using difference Fourier methods with the ligand-free rhPSMA (PDB code 2OOT;[10]) as a starting model. Calculations were performed with the program Refmac 5.1[11], and the refinement protocol was interspersed with manual corrections to the model employing the program Coot[12]. Library and PDB-format files of individual inhibitors were prepared using the PRODRG server[13] and the inhibitors were fitted into the positive electron density map in the final stages of the refinement. During the refinement process, ~1% of the randomly selected reflections were kept aside for cross-validation (Rfree). The quality of the final model was evaluated using the MOLPROBITY server[14]. The data collection and refinement statistics are summarized in Table S1.

PDB Accession Numbers

Atomic coordinates of the present structures together with the experimental structure factor amplitudes will be deposited in the RCSB Protein Data Bank.

TABLE S1

Data calculations and refinement statistics

| | GCPII/ARM-P2 | GCPII/ARM-P4 | GCPII/ARM-P8 | GCPII/ARM-M4 |
|---|---|---|---|---|
| PDB code | TBD | TBD | TBD | TBD |
| Data Collection Statistics | | | | |
| Wavelength (Å) | 1.0000 | 1.0000 | 1.0000 | 1.0000 |
| Temperature (K) | 100 | | | |
| Space group | I222 | | | |
| Unit-cell parameters: a, b, c (Å) | a = 101.5; b = 130.0; c = 158.6 | a = 101.7; b = 130.0; c = 159.0 | a = 101.8; b = 130.0; c = 158.8 | a = 101.5; b = 130.0; c = 159.2 |
| Resolution limits (Å) | 30.0-1.69 (1.75-1.69)* | 30.0-1.59 (1.65-1.59)* | 30.0-1.59 (1.63-1.59)* | 30.0-1.78 (1.84-1.78)* |
| Number of unique reflections | 114,649 (9,759) | 137,271 (11,088) | 137,748 (10,972) | 100,565 (9,717) |
| Redundancy | 5.8 (2.5) | 7.0 (5.0) | 6.6 (3.8) | 7.1 (5.6) |
| Completeness (%) | 97.8 (84.1) | 97.6 (79.9) | 96.9 (77.9) | 99.7 (97.3) |
| I/σ (I) | 18.4 (2.1) | 27.8 (2.0) | 15.4 (2.6) | 21.3 (2.5) |
| $R_{merge}$ | 0.086 (0.492) | 0.058 (0.501) | 0.078 (0.438) | 0.086 (0.520) |
| Refinement Statistics | | | | |
| Resolution limits (Å) | 30.0-1.69 (1.73-1.69)* | 30.0-1.59 (1.63-1.59)* | 30.0-1.59 (1.63-1.59)* | 20.0-1.78 (1.82-1.78)* |
| Total number of reflections | 112,878 (6,994) | 135,823 (7,887) | 135,631 (7,827) | 99,006 (6,972) |
| Number of reflections in working set | 111,178 (6,872) | 134,450 (7,815) | 133,594 (7,726) | 97,519 (6,871) |
| Number of reflections in test set | 1,700 (122) | 1,373 (72) | 2,037 (101) | 1,487 (101) |
| R factor | 16.0 (23.6) | 16.8 (25.3) | 16.1 (24.6) | 15.7 (26.6) |
| Free-R | 18.5 (29.3) | 19.1 (33.0) | 18.3 (28.7) | 18.5 (29.1) |
| Total number of non-H atoms | 6,491 | 6,618 | 6,687 | 6,546 |
| Number of inhibitor atoms | 92# | 52 | 128# | 41 |
| Number of ions | 4 | 4 | 4 | 4 |
| Number of water molecules | 505 | 612 | 581 | 563 |
| Average B factor (Å$^2$) | | | | |
| Protein atoms | 28.0 | 25.9 | 24.5 | 18.7 |
| Water molecules | 38.4 | 36.3 | 37.4 | 27.4 |
| Ligand atoms | 40.3 | 48.5 | 51.8 | 48.8 |
| r.m.s.d. | | | | |
| Bond lengths (Å) | 0.021 | 0.018 | 0.017 | 0.021 |
| Bond angles (°) | 1.85 | 1.71 | 1.69 | 1.72 |
| Planarity (Å) | 0.011 | 0.010 | 0.011 | 0.010 |
| Chiral centers (Å$^3$) | 0.14 | 0.13 | 0.12 | 0.14 |
| Ramachandran plot (%) | | | | |
| Most favored | 97.7 | 97.7 | 97.7 | 97.8 |
| Allowed | 2.3 | 2.3 | 2.3 | 2.2 |
| Disallowed | 0 | 0 | 0 | 0 |
| Missing residues | 44-54; 654-655 | 44-54; 654-655 | 44-54; 654-655 | 44-54; 654-655 |

*Values in parentheses correspond to the highest resolution shells
**Calculated with MOLPROBITY[14]
inhibitor modeled in two conformations Computational Studies
Quantum Chemical Computations Models of substituted methyl-amino-phenyls were constructed using the software Maestro.[15] All calculations were carried out using the Jaguar suite of electronic structure programs.[16] Geometry optimization was performed using Density functional theory with a 6-41G*+ basis set and the hybrid B3LYP functional.[17]

Molecular Dynamics Simulations

The crystal structure of ARM-P2-DNP in complex with PSMA (695 residues) was used to setup all the protein-ligand complexes. MeO-P0, ARM-P0, ARM-P2, ARM-P4 and ARM-P8 were modeled in the same protein structure on the basis of available experimental data. The LigPrep module of the software Maestro was used to add missing hydrogen atoms, choose the protonation state of protein side chains, and minimize the energy of the protein-ligand complex.[18] The 2005 update of the OPLS force field was used throughout.[19] The resulting structure was then embedded in a triclinic box of circa 13300 TIP3P water molecules,[20] the dimension of the box was circa 96×87×94 Å. The net charge of the system was neutralized by addition of one sodium ion to the solvent box. The total number of atoms was circa 53,000 atoms. The simulations were performed with the Desmond molecular dynamics package[21]. All bond lengths to hydrogen atoms were constrained using MM-SHAKE.[22] Van der Waals and short range electrostatic interactions were cut off at 9 Å. Long range electrostatic interactions were computed using the particle mesh Ewald method using a 32×32×32 grid with σ=2.18 Å and fifth-order B-splines for interpolation.[23] A RESPA integrator was used with a time-step of 2 fs, and the long range electrostatic interactions were computed every 6 fs.[24] Each system was initially energy minimized with steepest decent and then subjected to the following equilibration protocol: 12 ps of dynamics at 10 K in the NVT ensemble (Berendsen thermostat)[25] and harmonic restraints (50 kcal/mol/A²) on the solutes heavy atoms, followed by 12 ps in the NPT ensemble (Berendsen thermostat and barostat) at 10 K and retaining harmonic restraints on the solutes heavy atoms, followed by 24 ps in the NPT ensemble (Berendsen thermostat and barostat) at 300 K and retaining harmonic restraints on the solutes heavy atoms, followed by 24 ps in the NPT ensemble (Berendsen thermostat and barostat) at 300 K without harmonic restraints on the solutes heavy atoms, followed by 100 ps of dynamics at 300 K in the NPT ensemble (Martyna-Tobias-Klein barostat and Nose-Hoover thermostat).[26,27] The production simulations were run for 50 nanoseconds in the NPT ensemble (300 K, 1 bar, Martyna-Tobias-Klein barostat and Nose-Hoover thermostat). Coordinates were saved every 10 ps and analyzed using the software Visual Molecular Dynamics.[28]

Results and Discussion
Dependence of Linker Length on Binding Affinity

TABLE 1

Linker length dependence on PSMA inhibitory potency.

| Compound | X | n | $IC_{50}$ (nM)[b] | $K_i$ (nM)[c] |
|---|---|---|---|---|
| 1, ARM-P0 | DNP[a] | 0 | 1.76 ± 0.41 | 0.078 ± 0.018 |
| 2, ARM-P1 | DNP | 1 | 1.05 ± 0.11 | 0.047 ± 0.005 |
| 3, ARM-P2 | DNP | 2 | 0.54 ± 0.18 | 0.024 ± 0.008 |
| 4, ARM-P4 | DNP | 4 | 0.46 ± 0.18 | 0.020 ± 0.008 |
| 5, ARM-P6 | DNP | 6 | 2.29 ± 0.60 | 0.101 ± 0.027 |
| 6, ARM-P8 | DNP | 8 | 3.29 ± 1.14 | 0.145 ± 0.050 |
| 7, ARM-P12 | DNP | 12 | 37.3 ± 16.2 | 1.65 ± 0.72 |
| 8, MeO-P0 | OMe | 0 | 30.5 ± 12.1 | 1.35 ± 0.54 |
| 9, MeO-P2 | OMe | 2 | 40.8 ± 9.4 | 1.81 ± 0.42 |
| 10, MeO-P4 | OMe | 4 | 30.2 ± 14.4 | 1.34 ± 0.64 |
| 11, MeO-P8 | OMe | 8 | 131.0 ± 57.6 | 5.79 ± 2.54 |
| 12, MeO-P12 | OMe | 12 | 165.2 ± 58.9 | 7.30 ± 2.60 |

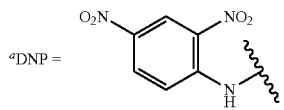

[a]DNP =

[b]$IC_{50}$ values represent the mean of triplicate experiments.
[c]$K_i$ values were calculated from $IC_{50}$ and $K_m$ values using the Cheng-Prusoff equation as described in the supporting information.

To evaluate in detail the effect of linker length on PSMA binding affinity, we prepared various derivatives of ARM-P (Table 1, 1-12). These compounds consist of glutamate ureas linked to DNP or methoxy groups by oxyethylene moieties of varying lengths. They are named ARM-Px and MeO-Px, respectively, wherein "x" corresponds to the number of oxyethylene units in the linker. Evaluation of these compounds for their ability to inhibit PSMA activity proved quite revealing. In all cases, ARM-P derivatives were found to possess Ki values lower in magnitude than their counterparts lacking DNP (compounds 1-7 versus 8-12). In some cases, the affinity difference was up to two orders of magnitude (compound 3 versus 9). This result indicated to us that perhaps the DNP function itself might be playing a role in binding PSMA. Such a hydrophobic interaction involving an aromatic ring and PSMA was not completely unexpected given the proximity of the glutamate-urea binding site to a known hydrophobic pocket in PSMA.[17,18] Indeed, inhibitors containing hydrophobic functionality distal to the glutamic acid moiety have exhibited high potency against PSMA.[12,19,20]

A model involving binding of the DNP moiety to the hydrophobic pocket adjacent to the S1 site did not explain the decrease in affinity between ARM-P2 and derivatives with shorter oxyethylene linkers (i.e., ARM-P0 and ARM-P1). Indeed, one would expect ARM-P0 and ARM-P1 to exhibit enhanced potency versus ARM-P2 because of the close proximity of the accessory hydrophobic pocket to the P1 glutamate binding cavity. The opposite trend suggested perhaps the presence of an alternative hydrophobic binding site, situated at a substantial distance away from this cavity. This hypothesis is supported by observations in related systems in which bifunctional ligands bind proteins at two remote sites. In such systems, an ideal linker length between binding poles is required for maximum affinity; linkers that are too short to access secondary binding sites experience suboptimal enthalpic benefit from bivalent binding, while linkers that are too long experience high entropic costs upon bivalent binding.[21-23]

Notably, compounds within the MeO-P series (8-12) containing relatively short linkers all bind PSMA with comparable affinity. The presence of linkers consisting of 8 oxyethylene groups or longer appears to inhibit compound binding, a trend that can be explained on steric grounds.[24] The increased sensitivity of ARM-P derivatives to changes in linker length versus MeO-P compounds suggests that factors other than simple steric bulk are operating for the ARM-Ps.

Structure-Activity Studies: Effect of Varying Aromatic Groups on Binding Affinity To test further our model for bidentate binding, we set out to probe the impact of the phenyl ring substituent on inhibitor potency. We therefore synthesized analogues of ARM-P2 replacing the DNP moiety with a range of electronically distinct aromatic species (3, 13-17, Table 2). As shown, these analogues included nitrophenyl (ortho and para to the linker), p-methoxyphenyl, phenyl, and cyclohexyl derivatives. Consistent with the hypothesis for multisite interaction, profound changes in affinity were observed in this series. Interestingly, the parent dinitrophenyl-containing compound (ARM-P2) possessed the highest potency of all the analogues tested (Ki=24 pM), and removal of nitro groups led to three-fold decreases in affinity in the p-nitrophenyl (13) and o-nitrophenyl (14) analogues (Ki=60 and 78 pM, respectively). The similarities between these analogues suggests that inhibitor potency is dictated by electronic rather than steric effects. Phenyl (15) and methoxyphenyl (16) analogues proved an additional order of magnitude less potent than mononitrated derivatives (Ki=730 and 970 pM, respectively), and the cyclohexyl-substituted derivative (17) proved yet another order of magnitude worse than the least potent aryl compounds (Ki=15.1 nM). This may result from the enhanced steric bulk of the cyclohexyl substituent versus planar arenes.

Figure 15:
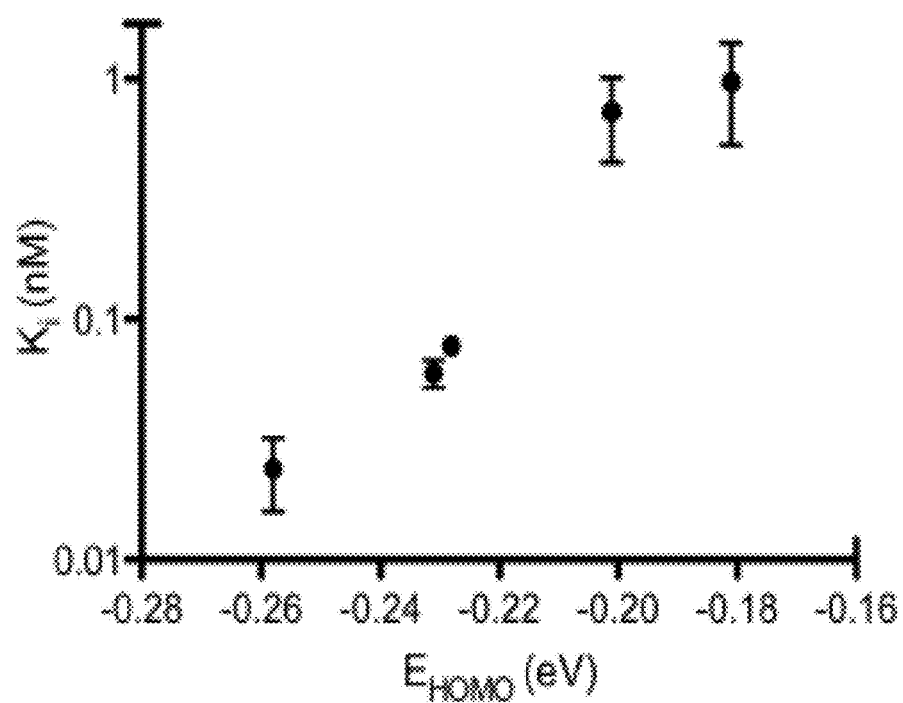
FIG. 15 shows the correlation between $K_i$ values and $E_{HOMO}$ of aromatic ring component of ARM-P analogues. Measured $K_i$ values (mean of triplicate experiments±standard deviation) are plotted versus HOMO energies calculated using density functional theory (DFT). The hybrid functional B3LYP with a 6-31G*+ basis set was used.

To quantify electronic effects in this system, we performed density functional theory (DFT) calculations to relate the electron density of the aromatic ring to PSMA inhibitory potency.[25] For substituted arenes this can be conveniently quantified by calculating the arene HOMO energy. An excellent correlation was observed between the HOMO energies of aromatic substituents and experimentally determined $K_i$ values (FIG. 15). Electron poor aromatic rings are expected to experience strong n-stacking interactions with electron-rich arenes,[26,27] suggesting perhaps that such interactions may be dominant in dictating binding affinity in this system. These results are strongly indicative of multisite binding in the ARM-P series, and led us to test this hypothesis further using X-ray crystallography.

Crystallographic Studies

Initial Refinement and Analysis.

Crystal structures were determined for PSMA in complex with ARM-P ligands containing 2, 4, and 8 oxyethylene units in the linker region (3, 4, and 6) and with MeO-P4 (10), which lacks the DNP moiety, and were refined at the

TABLE 2

Dependence of $K_i$ on substituents and electronics of aromatic ring.

| Compound | X | $E_{Homo}$ (eV)[a] | $IC_{50}$ (nM)[b] | $K_i$ (nM)[c] |
|---|---|---|---|---|
| 3, ARM-P2 | DNP | −0.251 | 0.54 ± 0.18 | 0.024 ± 0.008 |
| 13 | o-NO$_2$—Ph | −0.228 | 1.78 ± 0.15 | 0.078 ± 0.007 |
| 14 | p-NO$_2$—Ph | −0.231 | 1.36 ± 0.18 | 0.060 ± 0.008 |
| 15 | Ph | −0.201 | 16.6 ± 6.3 | 0.73 ± 0.28 |
| 16 | p-MeO—Ph | −0.181 | 21.9 ± 9.9 | 0.97 ± 0.44 |
| 17 | Cyclohexyl | N/A | 342.3 ± 170.5 | 15.1 ± 7.5 |

[a]$E_{HOMO}$ of the aryl ring (X) was calculated using Density Functional Theory, and reported in electron-volts. The hybrid functional B3LYP with a 6-31G*† basis set was used.
[b]$IC_{50}$ values represent the mean of triplicate experiments.
[c]$K_i$ values were calculated using $IC_{50}$ and $K_m$ values via the Cheng-Prusoff equation as outlined in the supporting information. A $K_m$ value of 925 nM was using in these calculations.

resolution of 1.69 Å, 1.59 Å, 1.59 Å, and 1.78 Å, respectively. Individual compounds were fit into the positive peaks on the difference $F_o$-Fc electron density map in the final stages of refinement. For all four inhibitors, clear interpretable densities were observed for the C-terminal part encompassing the P1' glutarate, the urea linkage, the lysine linker and the triazole ring. Although density corresponding to the DNP phenyl ring is defined in all ARM-P complexes, density corresponding to the nitro groups is absent suggesting that the DNP moiety is present in at least two different conformations. Also, electron density peaks corresponding to the poly-oxyethylene linker were absent from all complexes, consistent with a lack of intermolecular contacts between this flexible element and the protein.

Figure 16:
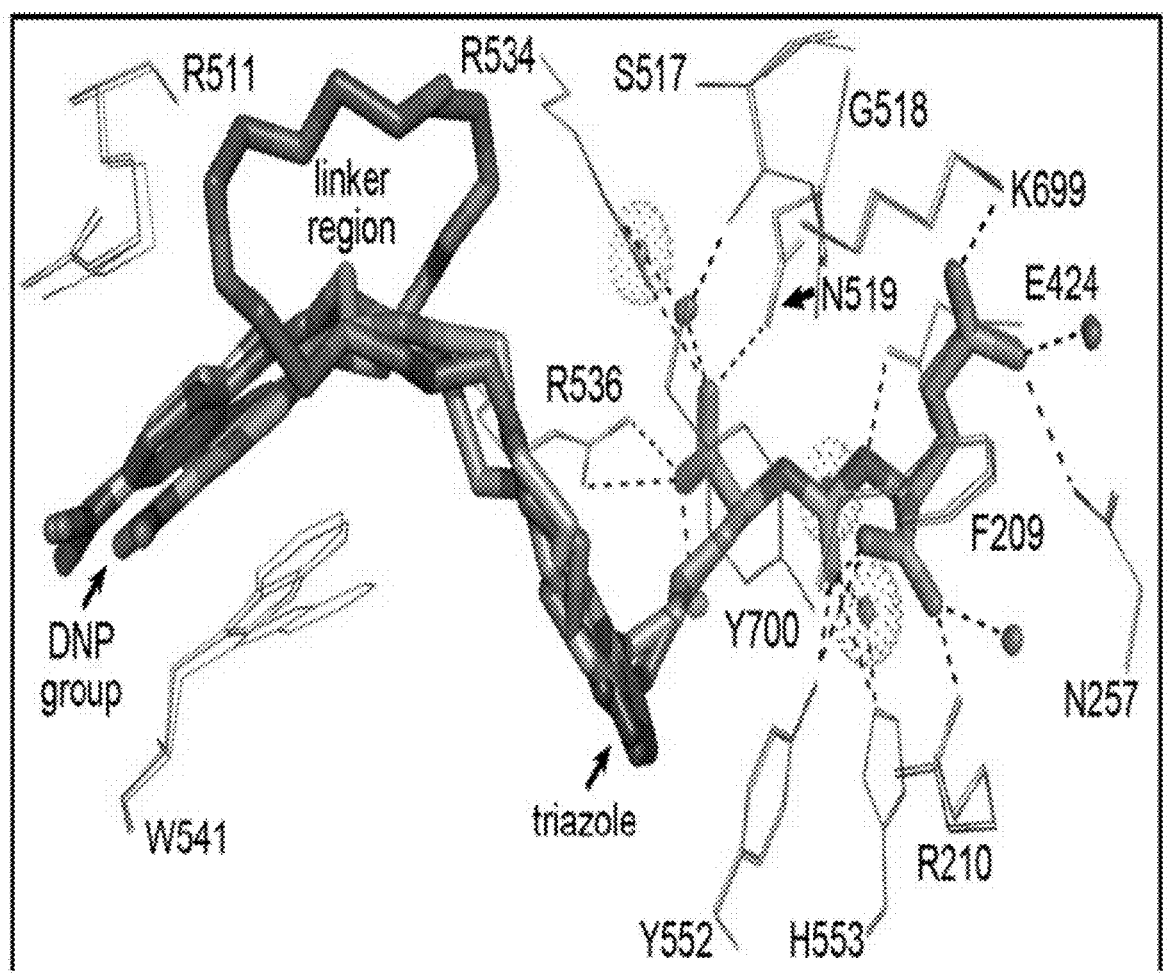
FIG. 16 provides a close-up of PSMA active site bound to bifunctional glutamate urea inhibitors ARM-P2 (gold), ARM-P4 (grey), and ARM-P8 (blue). Structures were superimposed on with corresponding (or equivalent) Cα atoms. Inhibitors are shown in stick representation and protein residues are shown as lines. Hydrogen bonding interactions are indicated by dashed lines. The zinc ions and chloride ion in the active site are labeled as grey and green dotted spheres, respectively, and water molecules are depicted as red spheres. In both protein and inhibitor structures, carbon atoms are colored as indicated above, and other atoms are colored red (oxygen), and blue (nitrogen).

Structures of ARM-P2, ARM-P4, and ARM-P8 in complex with PSMA are depicted in FIG. 16. Despite the attachment of large oxyethylene linkers, the glutamate urea portions of all inhibitors interact with the protein active site in a fashion reminiscent of previously reported complexes with urea12,13,17 and phosphonate28 inhibitors, and the substrate N-acetyl-aspartyl-glutamate (NAAG).29 In all structures, positioning of the P1' glutarate is enforced by H-bonds (indicated as dashed lines) with Arg210, Asn257, Tyr552, Lys699, Tyr700, and active-site water molecules, and hydrophobic interactions with the side chains of Phe209 and Leu428. The ureido nitrogen atoms serve as H-bond donors in interactions with Glu424 and the Gly518 main chain carbonyl, and the carbonyl oxygen makes contacts with both the catalytic zinc atom and Tyr552, and His553. The P1 α-carboxylate in all inhibitors structurally overlaps with the equivalent groups of previously reported complexes, and is held in place by interactions with an arginine-rich patch (Arg463, Arg534, Arg536) along with H-bonding contacts to Asn519, the Ser517 main-chain carbonyl, and water molecules.[17,18]

Figure 17A:
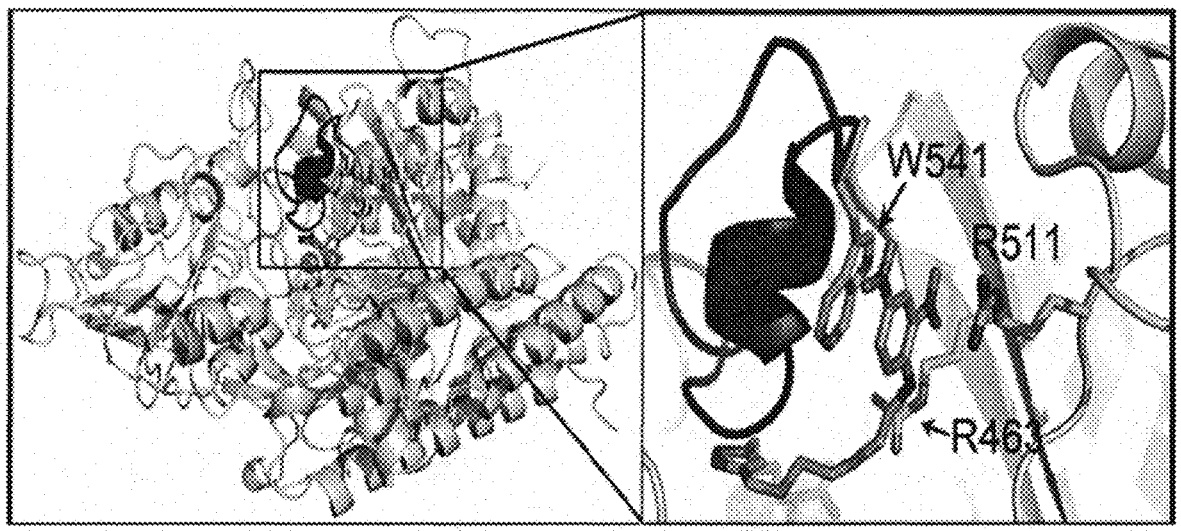
FIG. 17A-C shows that the PSMA/ARM-P2 complex reveals a previously unreported arene-binding cleft. (17A) Global view of PSMA with a close-up of arene-binding site. Residues making up the arene-binding cleft are labeled in cyan. The entrance lid (residues 542-548), which resides in an open conformation in the ARM-P2 complex, is indicated as a red loop. Overlaid on this complex is the entrance lid in its closed conformation (colored blue), which would come into steric conflict with the linker region of the inhibitor. (17B and 17C) Close-up images of the urea binding sites in structures containing both open and closed entrance loops. In all panels, structural data for PSMA with a the closed entrance lid comes from the complex with the small urea-based inhibitor DCIBzL (PDB ID-3IWW).30 The zinc ions in the active site are labeled as orange spheres and the ARM-P2 carbons are colored gold. The DCIBzL carbons in B and C are colored purple FIG. 18 provides a close-up view of the active site of PSMA bound to MeO-P4. Hydrogen bonding interactions are indicated by dashed lines. The zinc ions in the active site and adjacent chloride ion are labeled as grey and green dotted spheres, respectively, and water molecules are depicted as red/darker spheres. In both protein and inhibitor structures, carbon atoms are colored in olive, and other atoms are colored red (oxygen), and blue (nitrogen).

Discovery of an arene-binding cleft. A key site of interaction between PSMA and all ARM-P derivatives is the triazole ring, which was observed to pack against the side chains of Tyr552 and Tyr700 in all complexes (FIG. 16). The steric hindrance caused by the oxyethylene linker emanating from the triazole ring prevents closure of the enzyme's entrance lid (amino acids Trp541-Gly548), as observed for PSMA complexes with smaller ligands.[18] A key consequence of the entrance lid's open conformation is the revelation of a previously unreported binding cleft for the DNP ring (FIG. 17).[18]

Figures 17B, 17C:
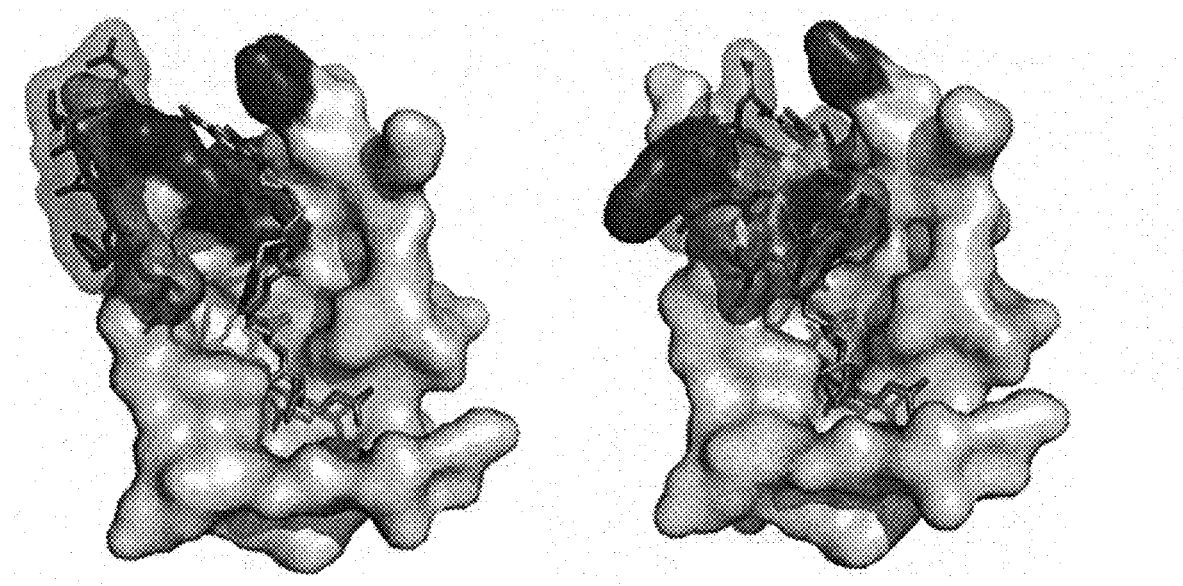

The arene-binding region, formed from the indole group of Trp541 and the guanidinium group of Arg511 holds the DNP ring in close contact with these groups at distances of 3.1 Å and 3.9 Å, respectively. The bottom of the cleft is lined by the Arg463 side chain. Positioning of the phenyl ring creates a plane virtually parallel to both indole and guanidinium functionalities, suggesting that simultaneous π-cation (DNP-Arg511) and n-stacking (DNP-Trp541) interactions may both contribute to inhibitor binding.31,32 Critically, the arene-binding region is only revealed upon opening of the entrance lid (FIG. 17B); closure of the entrance lid, as in the overlaid complex between PSMA and the small urea-based inhibitor DCIBzL,30 would lead to significant steric overlap with the triazole moiety as well as closure of the arene-binding site (FIG. 17C). Thus, the protein is capable of adopting two separate conformations, each suited to accommodate high-affinity binding interactions with distinct classes of glutamate-urea inhibitors.

Figure 18:
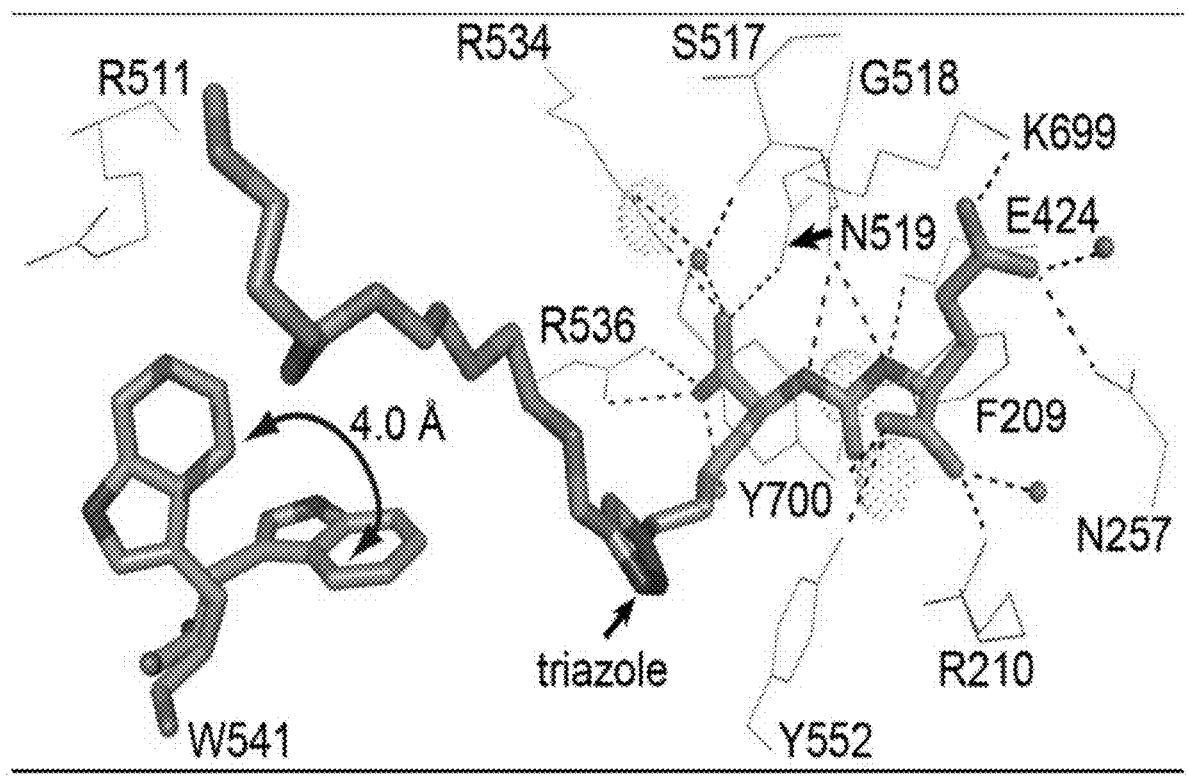

A key structural feature was observed in the MeO-P4 complex (FIG. 18). Here, unlike in the ARMP complexes, Trp541 exists in two distinct conformations. The non-stacking conformation is rotated approximately 4 Å from what is seen in ARM-P complexes, and blocks the arene-binding groove. The conformational flexibility exhibited by Trp541 in the PSMA/MeO-P4 complex suggests that when present, the dinitroarene stabilizes the side chain indole moiety via nt-stacking, as implied by the ARMP structures depicted above. Taken together, these data provide strong support for a model in which ARM-Ps bind PSMA through interactions at both the enzyme active site and at a newly reported arenebinding cleft. Notably, the complex between PSMA and MPE,33 a methotrexate-derived phosphonate, was also shown to possess an open entrance lid like the complexes disclosed herein.[18] It was concluded from the PSMA/MPE complex that the protein's ability to adopt an open conformation serves to enable its binding to relatively large substrates, such as folyl-poly-γ-glutamates. One might imagine that the revelation of an arene-binding site upon opening of the entrance lid might serve to enhance affinity for these arene-containing enzyme substrates. Interestingly, however, the pendant pteroyl ring in the MTE complex was not observed to interact with the PSMA arene-binding cleft, perhaps due to its relatively short linkage to the zinc-binding phosphonate region. The observations reported herein suggest that perhaps larger natural poly-γ-glutamate substrates are able to make use of the arene-binding site, however further studies are necessary to test this possibility.

Molecular Dynamics (MD) Simulations

Figure 19:
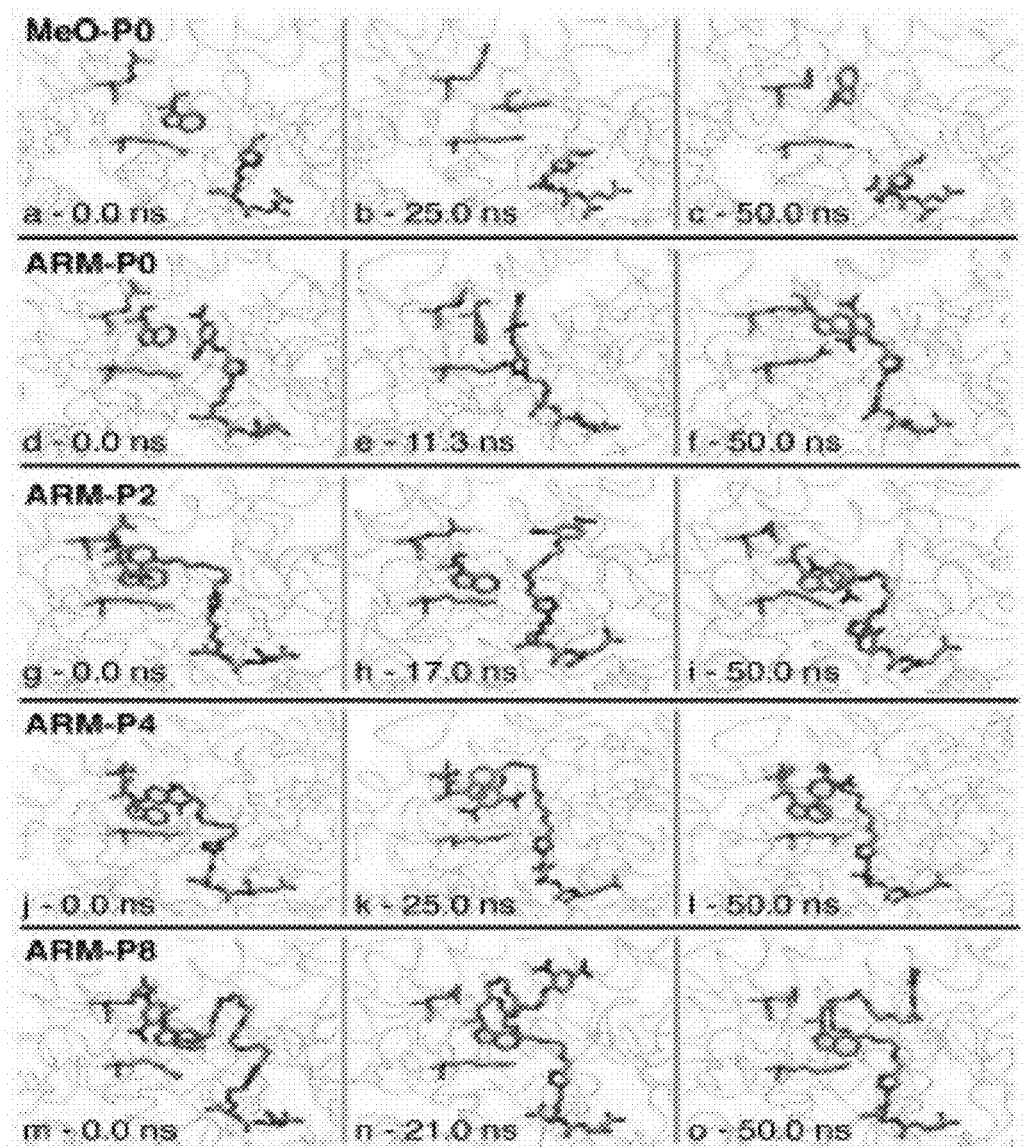
FIG. 19 provides selected snapshots from the MD simulations of PSMA/ARM-P complexes. The ligands are represented in varying shaded sticks, Arg463, Arg511 and Trp541 are represented in lighter gray sticks. Figure created with the program VMD.[37]

To clarify the nature of the protein-ligand interactions in the ARM-P complexes, explicit solvent molecular dynamics (MD) simulations were carried out using crystallographic data for PSMA complexes with ARM-P0, ARMP-P2, ARM-P4, ARM-P8 and MeO-P0. Each protein-ligand complex was modeled with the OPLS-AA force field,34 embedded in a triclinic box of TIP3P water molecules.35 Dynamics were simulated for 50 ns using the Desmond software package.[36] These simulations revealed a number of noteworthy features (see Supporting Information for video files for all simulations). Although the PSMA active site and glutamate urea moieties are fairly rigid throughout the timescale of MD simulations, distal protein-ligand interactions exhibit highly dynamic behavior. For example, the simulation of the MeO-P0-PSMA complex revealed that the arene-binding site is unstable in the absence of DNP; Trp541 tends to rotate toward Arg511, thus obscuring the arenebinding site (FIG. 19, panels a-c). This observation directly correlates with the disorder in Trp541 observed in the MeO-P4-PSMA crystal structure (FIG. 16). Furthermore, the PEG moieties in all complexes are highly dynamic and do not seem to form specific interactions with PSMA, suggesting that these make minimal enthalpic contributions to binding affinity. These observations also explain the absence of electron density corresponding to linker regions in all crystal structures.

By far the most stable intermolecular contact in the arene-binding site in ARM-P-PSMA complexes is the stacking interaction between DNP and Trp541. For all ARMs, the DNP moieties participate in face-to-face interactions with Trp541 side chain indole moieties for significant time periods throughout MD simulations. Simulations of the ARM-P0-PSMA complex revealed a remarkable level of flexibility in the triazole-alkyl region, which enables π-stacking contacts in the arene-binding site to remain intact even in the absence of an oxyethylene linker (FIG. 19, panels d-f). When stacked with the Trp541 side chain indole, the DNP ring is observed to rotate in-plane, supporting the hypothesis that the lack of well defined electron density corresponding to nitro groups in crystal structures is due to the presence of multiple arene conformations. However, in all ARM-P complexes, the nitro groups in the DNP ring are frequently observed pointing toward the Arg463 side chain guanidinium group, suggesting possible hydrogen bonding or electrostatic interactions between these groups. Furthermore, although crystallographic data support a role for π-cation interactions with Arg511 in the arene-binding site, this residue is highly disordered in MD simulations, and does not form long-lived contacts with the ligand. This observation is consistent with the data presented in Table 2 and FIG. 15, which suggest that cation-π interactions play a relatively minor role versus it-stacking interactions in stabilizing these systems. Notably, during the course of MD simulations for both ARM-P2 (panels g-i) and ARM-P8 (panels m-o), the DNP ring dissociates from the arene-binding cleft, whereas this interaction remains intact in the ARM-P4 simulation (panels j-l). Taken together, these data suggest that the DNP-Trp541 interactions are relatively weak. Interestingly, the contact with Trp541 reforms rapidly during the simulations of ARM-P2, but not ARM-P8; this likely reflects both the high entropic penalty associated with bivalent binding in ARM-P8 as well as the tendency for the molecule's lengthy PEG linker to occupy the arene-binding site, thus preventing the DNP group's return to Trp541. From a functional standpoint, the propensity of ARM-P8 to disengage from the PSMA arene-binding site enables it to form ternary complexes with prostate cancer cells and antibodies, which is critical to its cytotoxic activity.[3] However, this functionality comes at the expense of PSMA binding affinity. This model suggests the possibility of ultra high-affinity ARM-P analogues capable of interacting simultaneously with the PSMA arene-binding site and anti-DNP antibodies.

CONCLUSION

In the present application we have detailed the discovery of an arene-binding site on prostate-specific membrane antigen (PSMA), which gives rise to unusually high affinity binding interactions with designed bifunctional antibody-recruiting small molecules (ARMs). The conclusions presented herein are supported by extensive crystallographic, biochemical, and computational data, which, taken together, strongly suggests a model in which bidentate binding of ARM-Ps to PSMA leads to substantial increases in inhibitor potency. The serendipitous nature of the discovery reported herein along with the relative simplicity of the PSMA arene-binding site—which consists merely of three amino acids only one of which (Trp541) is responsible for affinity enhancement—suggest that low-affinity binding sites for arenes could be quite prevalent among proteins. Along these lines, it is well-documented that a large proportion of circulating immunoglobulin possess high-affinity binding activity against nitroarene ligands,38 and between 1 and 10% of myeloma proteins bind nitrophenyl ligands.[39] The possibility that such binding sites arise from conserved folds within immunoglobulin domains has been suggested,[40] however, this trend may also result from the unique immunogenicity of nitroarenes,[41,42] a property that has also been attributed to their propensity to form hydrophobic contacts with proteins.[41] In either case, although structural data exists demonstrating the unique propensity of nitroarenes to engage in n-stacking interactions with aromatic amino acid side chains,[43,44] the proteomic prevalence of nitroarene-binding motifs has not been systematically explored. The widespread existence of such binding sites could enable facile optimization of small molecule ligands for proteins identified through high-throughput screening, and could find ready utility in fragment-based approaches to inhibitor design.[45]

Although underexplored, strategies that utilize small molecules to enhance recognition of pathogens by the human immune system promise to leverage the strengths of both antibody- and small-moleculebased therapeutic approaches. The results reported herein suggest the possibility for improving such technologies for treating prostate cancer. For example, ultra-high-affinity ARM-Ps could be constructed by exploiting the presence of the arene-binding site in PSMA and converting the highly flexible first generation ARM-Ps into more rigid scaffolds. More broadly, the high-level expression of PSMA (GCPII) on prostate cancer cell surfaces and on tumor neovasculature,[46] as well as its putative role in the pathophysiology of schizophrenia,[47] have rendered it an extremely useful and popular target for inhibitor design. The results presented herein therefore could substantially impact the development of effective diagnostic and therapeutic approaches for patients suffering from cancer and other diseases.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. Any inconsistency between the material incorporated by reference and the material set for in the specification as originally filed shall be resolved in favor of the specification as originally filed. The foregoing detailed description and examples have been given for clarity of understanding only. No unnecessary limitations are to be understood therefrom. The invention is not limited to the exact details shown and described, for variations obvious to one skilled in the art will be included within the invention defined by the following claims.

All headings are for the convenience of the reader and should not be used to limit the meaning of the text that follows the heading, unless so specified.

The invention claimed is:

1. A compound for use in the treatment of prostate cancer in a patient according to the chemical structure:

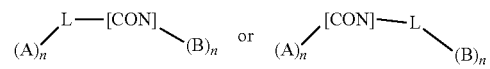

Wherein n is independently 1 or 2;

A is an antibody binding moiety according to the chemical structure:

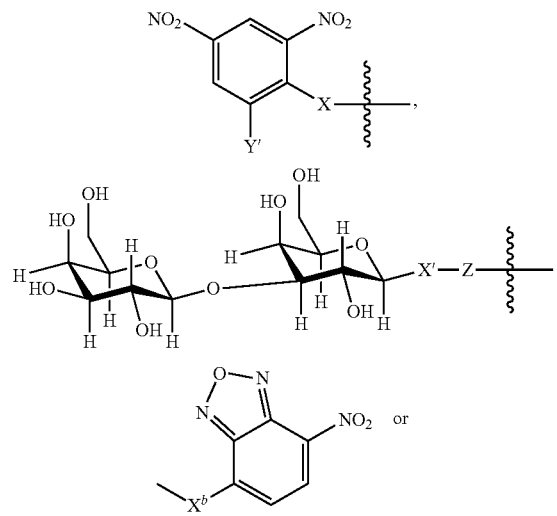

-continued

Where Y' is H or $NO_2$;

X is O, $CH_2$, $NR^1$, S(O), $S(O)_2$, —$S(O)_2O$, —$OS(O)_2$, or $OS(O)_2O$;

$R^1$ is H, a $C_1$-$C_3$ alkyl group, or a —$C(O)(C_1$-$C_3)$ group;

X' is $CH_2$, O, N—$R^{1'}$ or S;

$R^{1'}$ is H or a $C_1$-$C_3$ alkyl;

Z is a bond, a monosaccharide, disaccharide, oligosaccharide, glycoprotein or glycolipid;

$X^b$ is a bond, O, $CH_2$, $NR^1$ or S;

B is a cell binding moiety according to the chemical formula:

Where $X_1$ and $X_2$ are each independently $CH_2$, O, NH or S;

$X_3$ is O, $CH_2$, $NR^1$, S(O), $S(O)_2$, —$S(O)_2O$, —$OS(O)_2$, or $OS(O)_2O$;

$R^1$ is H, a $C_1$-$C_3$ alkyl group, or a —$C(O)(C_1$-$C_3)$ group;

k is an integer from 1 to 15;

L is a linker according to the chemical formula:

Or L is a polyethylene glycol, polypropylene glycol or polypropylene-co-polyethylene glycol linker having between 1 and 20 glycol units;

Where $R_a$ is H, $C_1$-$C_3$ alkyl or alkanol or forms a proline side chain with $R^3$;

$R^3$ forms a proline side chain with $R_a$ or is a side chain derived from an amino acid selected from the group consisting of alanine, arginine, asparagine, aspartic acid, cysteine, glutamine, glutamic acid, glycine, histidine, isoleucine, leucine, lysine, methionine, phenylalanine, serine, threonine, tryptophan and valine; and Each m is independently an integer from 1 to 30; or L is a linker according to the chemical formula:

Where Z and Z' are each independently a bond, —$(CH_2)_i$—O, —$(CH_2)_i$—S, —$(CH_2)_i$—N—R, wherein said —$(CH_2)_i$ group, if present in Z or Z', is bonded to [CON], antibody binding terminus (ABT) or cell binding terminus (CBT);

Each R is independently H, or a $C_1$-$C_3$ alkyl or alkanol group;

Each $R^2$ is independently H or a $C_1$-$C_3$ alkyl group;

Each Y is independently a bond, O, S or N—R;

Each i is independently an integer from 0 to 100;

D is $$—(CH_2)_i—Y—\overset{\overset{O}{\|}}{C}—Y—(CH_2)_i—\ ;\quad —(CH_2)_{m'}—\ ;$$
$$—\!\!+\!\!(CH_2)_{n'}\!—X''\!\!+\!\!_j$$

or a bond, with the proviso that Z, Z' and D are not each simultaneously bonds;

j is an integer from 1 to 100;

m' is an integer from 1 to 100;

n' is an integer from 1 to 100; and

X'' is O, S or N—R,
R is as defined above; and
[CON] is a bond or a moiety according to the chemical structure:

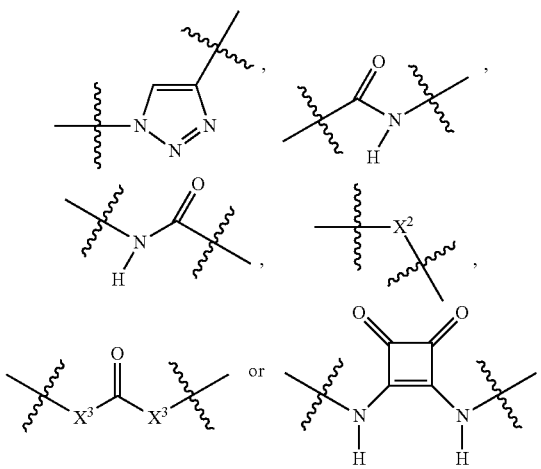

Where $X^2$ is O, S, $NR^4$, S(O), $S(O)_2$, —$S(O)_2$, —$OS(O)_2$, or $OS(O)_2O$;
$X^3$ is $NR^4$, O or S; and $R^4$ is H, a $C_1$-$C_3$ alkyl or alkanol group, or a —$C(O)(C_1$-$C_3)$ group; or
a pharmaceutically acceptable salt thereof.

2. The compound according to claim 1 wherein A is

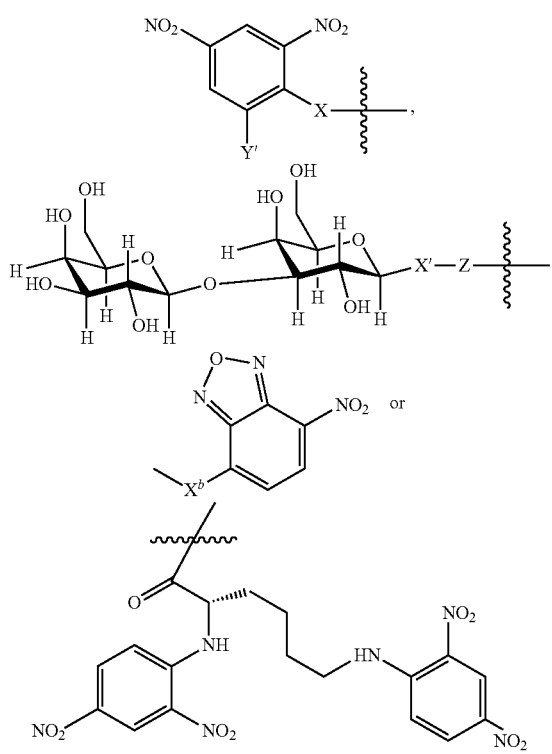

Where Y' is H;
X is O, $CH_2$ or $NR^1$;
$R^1$ is H, a $C_1$-$C_3$ alkyl group, or a —$C(O)(C_1$-$C_3)$ group;
X' is $CH_2$, O, N—$R^{1'}$ or S;
$R^{1'}$ is H or $C_1$-$C_3$ alkyl;

Z is a bond, a monosaccharide, disaccharide or oligosaccharide;
$X^b$ is a bond, O, $CH_2$, $NR^1$ or S; and
Each n is 1, or
a pharmaceutically acceptable salt thereof.

3. The compound according to claim 2 wherein A is

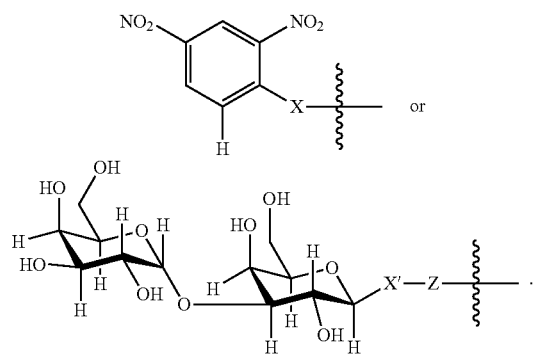

4. The compound according to claim 2 wherein X' is O or N—$R^{1'}$ and $R^{1'}$ is H.

5. The compound according to claim 2 wherein X' is O.

6. The compound according to claim 3 wherein A is

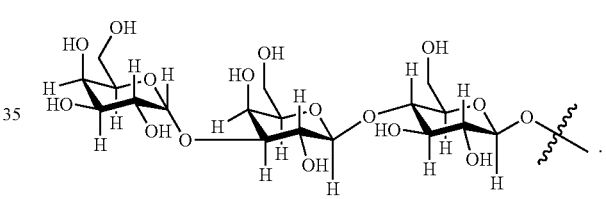

7. The compound according to claim 3 wherein Z is a monosaccharide selected from the group consisting of aldoses, ketoses and aminosugars.

8. The compound according to claim 3 wherein Z is a monosaccharide selected from the group consisting of D-glyceraldehdye, D-erythrose, D-Threose, D-ribose, D-arabinose, D-xylose, D-lyxose, D-allose, D-altrose, D-Glucose, D-Mannose, D-gulose, D-idose, D-galactose, dihydroxyacetone, D-erythrulose, D-ribulose, D-xylulose, D-Psicose, D-Fructose, D-Sorbose, D-Tagatose, galactoseamine, sialic acid and N-acetylglucosamine.

9. The compound according to claim 1 wherein Z is a disaccharide selected from the group consisting of sucrose, lactose, maltose, trehalose, cellobiose, kojibiose, isomaltose, β,β-trehalose, sophorose, laminaribiose, gentiobiose, turanose, maltulose, palatinose, mannobiose, melibiose, melibiulose, rutinose, rutinulose, and xylobiose.

10. The compound according to claim 1 wherein said linker is group according to the chemical formula:

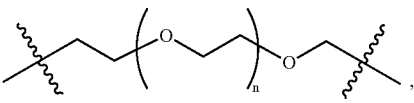

-continued

[chemical structures]

Where $R_a$ is H or forms a proline side chain with $R^3$ and $R^3$ forms a proline side chain with $R_a$ or is a side chain derived from an amino acid selected from the group consisting of alanine, arginine, asparagine, aspartic acied, cysteine, glutamine, glutamic acid, glycine, histidine, isoleucine, leucine, lysine, methionine, phenylalanine, serine, threonine, tryptophan and valine; and Each m is independently an integer from 1 to 15.

11. The compound according to claim 1 wherein [CON] is a

[chemical structures]

group, where $X^2$ is O, S or $NR^4$; and $R^4$ is H or a $C_1$-$C_3$ alkyl or alkanol group.

12. The compound according to claim 1 wherein said linker is a group according to the formula:

[chemical structure]

Wherein m is an integer from 1 to 10.

13. A compound according to claim 1 wherein A is

[chemical structure]

where X is O or NH;

L is a

[chemical structure]

group;

where m is an integer from 2 to 15; and

[CON] is attached to A or B through linker L.

14. A compound according to claim 1 according to the chemical structure:

[chemical structure]

Where n is an integer from 2 to 15; and

X is

[chemical structure]

Where $Y^N$, $Y^{N1}$ and Y' is H or $NO_2$; with the proviso that at least one of $Y^N$, $Y^{N1}$ and Y' is $NO_2$, or a pharmaceutically acceptable salt thereof.

15. The compound according to claim 14 wherein X is

[chemical structure]

and Y' is H or $NO_2$.

16. The compound according to claim 15 wherein Y' is H.

17. The compound according to claim 14 wherein n is an integer from 1-8.

18. The compound according to claim 14 wherein n is an integer from 1-4.

19. A pharmaceutical composition comprising an anticancer effective amount of a chimeric compound according to claim 1 in combination with a pharmaceutically acceptable carrier, additive or excipient, optionally in combination with an anticancer effective amount of an additional anticancer agent.

20. The composition according to claim 19 wherein said composition further comprises an anticancer effective amount of an additional anticancer agent.

21. The composition according to claim 20 wherein said additional anticancer agent is an antimetabolite, an inhibitor of topoisomerase I and II, an alkylating agent, a microtubule inhibitor or mixtures thereof.

22. The composition according to claim 19 in parenteral dosage form.

23. The composition according to claim 22 wherein said parenteral dosage form is an intravenous dosage form.

24. A method of treating prostate cancer in a patient in need thereof comprising administering to said patient an effective amount of a composition according to claim 19.

25. The method according to claim 24 wherein said prostate cancer is metastatic prostate cancer.

26. A method of treating prostate cancer in a patient in need thereof comprising administering to said patient an effective amount of a composition according to claim 20.

* * * * *

UNITED STATES PATENT AND TRADEMARK OFFICE
CERTIFICATE OF CORRECTION

PATENT NO. : 10,703,823 B2
APPLICATION NO. : 16/045855
DATED : July 7, 2020
INVENTOR(S) : David Spiegel, Ryan Murelli and Andrew Zhang Page 1 of 1

It is certified that error appears in the above-identified patent and that said Letters Patent is hereby corrected as shown below:

In the Specification

Column 1, Line 29 Under Grant Support, the current paragraph currently reads:
This invention was supported by a grant from the National Institutes of Health, grant no. 1DP2OD002913-01. Consequently, the government retains certain rights in the invention.

Replace with the following:
This invention was made with government support under OD002913 awarded by National Institutes of Health. The government has certain rights in the invention.

Signed and Sealed this
Twenty-fifth Day of August, 2020

Andrei Iancu
*Director of the United States Patent and Trademark Office*